(12) United States Patent
Narimatsu et al.

(10) Patent No.: US 10,539,576 B2
(45) Date of Patent: Jan. 21, 2020

(54) LUNG CANCER DIFFERENTIAL MARKER

(71) Applicants: National Institute of Advanced Industrial Science and Technology, Tokyo (JP); Tokyo Medical University, Tokyo (JP)

(72) Inventors: Hisashi Narimatsu, Tsukuba (JP); Akira Togayachi, Tsukuba (JP); Yuzuru Ikehara, Tsukuba (JP); Hiroyuki Kaji, Tsukuba (JP); Atsushi Kuno, Tsukuba (JP); Takashi Ohkura, Tsukuba (JP); Hideki Matsuzaki, Tsukuba (JP); Yoshitoshi Hirao, Tsukuba (JP); Jun Iwaki, Tsukuba (JP); Minako Abe, Tsukuba (JP); Masaharu Nomura, Tokyo (JP); Masayuki Noguchi, Tsukuba (JP)

(73) Assignees: National Institute of Advanced Industrial Science and Technology, Tokyo (JP); Tokyo Medical University, Tokyo (JP)

( * ) Notice: Subject to any disclaimer, the term of this patent is extended or adjusted under 35 U.S.C. 154(b) by 0 days.

(21) Appl. No.: 15/620,214

(22) Filed: Jun. 12, 2017

(65) Prior Publication Data

US 2017/0283506 A1    Oct. 5, 2017

Related U.S. Application Data

(62) Division of application No. 13/823,922, filed as application No. PCT/JP2011/070635 on Sep. 9, 2011, now Pat. No. 9,696,320.

(30) Foreign Application Priority Data

Sep. 17, 2010   (JP) ................. 2010-209932

(51) Int. Cl.
| | | |
|---|---|---|
| G01N 33/574 | (2006.01) | |
| G01N 33/68 | (2006.01) | |
| C07K 14/47 | (2006.01) | |
| C07K 16/28 | (2006.01) | |
| C07K 16/30 | (2006.01) | |

(52) U.S. Cl.
CPC ..... *G01N 33/6893* (2013.01); *C07K 14/4748* (2013.01); *C07K 16/28* (2013.01); *C07K 16/3023* (2013.01); *G01N 33/57423* (2013.01); *G01N 33/574* (2013.01); *G01N 2440/38* (2013.01)

(58) Field of Classification Search
CPC .................................................. G01N 33/574
See application file for complete search history.

(56) References Cited

U.S. PATENT DOCUMENTS 9,696,320 B2   7/2017   Narimatsu et al.

OTHER PUBLICATIONS

Hirao et al. (J. Proteome Res. Nov. 7, 2014; 13 (11) :4705-16).*
Liang et al. (Glycobiology. Mar. 2015; 25 (3): 331-40).*
Richter et al. (J. Cancer Res. Clin. Oncol. Oct. 2008; 134 (10): 1059-65).*
Auricchio et al. (Biochem J. Oct. 1967; 105 (1): 35-8).
Liedtke et al. (Glycobiology. May 2001; 11 (5): 373-84).
Patriarca et al. (Virchows Arch. Jun. 1997; 430 (6): 455-60).
Ahn et al. (Mol. Cell. Proteomics. Jan. 2014; 13 (1): 30-48).
Gronberg et al. (Regul. Pept. Feb. 25, 2010; 160 (1-3): 68-74).
Stridsberg et al. (J. Anat. Mar. 2008; 212 (3): 229-34).
Portela-Gomes et al. (Regul. Pept. Nov. 30, 2010; 165 (1): 30-5).
Wang et al. (Cancer Lett. Oct. 1, 2014; 352 (2): 169-78).
Dai et al. (Electrophoresis. Sep. 2009; 30 (17): 2957-66).
He et al. (Clin. Chim. Acta. Apr. 2009; 402 (1-2): 102-6).
Rozek et al. (Tumour Biol. Jun. 2013; 34 (3): 1773-1781).
European Search Report relating to foreign counterpart of European Patent Application No. 11825097.6, dated Dec. 2, 2013.
Del Rio, Maguy, et al., "JLP5B9: new monoclonal antibody against polysialylated neural cell adhesion molecule is of value in phenotyping lung cancer", Journal of Immunological Methods, Jan. 1, 2000, vol. 233, No. 1-2, pp. 21-31.
Campodonico, Paola B., et al., "The Neural Cell Adhesion Molecule is Involved in the Metastatic Capacity in a Murine Model of Lung Cancer", Molecular Carcinogenesis, Jan. 1, 2010, vol. 49, pp. 385-397.
Aletsee-Ufrecht, Maria C., et al., "NCAM: a surface marker for human small cell lung cancer cells", FEBS Letters, Jul. 16, 1990, vol. 267, No. 2, pp. 295-300.
Vangsted, Annette, et al., "New Serum Markers for Small-Cell Lung Cancer. II. The Neural Cell Adhesion Molecule NCAM", Cancer Detection and Prevention, Jan. 1, 1994, vol. 18, No. 4, pp. 291-298.
Michalides, Rob, et al., "NCAM and Lung Cancer". International Journal of Cancer, Jan. 1, 1994, vol. 57, No. S8, pp. 34-37.
Lantuejout,S., et al., "668 Differential expression and prognosis value of neural cell adhesion molecules (NCAM) and polysialylated-NCAM (NCAM-PSA) in neuroendocrine lung tumors", Lung Cancer, Aug. 1, 1997, vol. 18, p. 171.
Office Action dated Feb. 6, 2015 to Chinese counterpart; Chinese Patent Application No. 201180054286.6; 2 Pages.
Yi-Ping, Rong et al., "Cloning and Characterization of a Novel Human Secretory Protein: Secretogranin III", Acta Biochimica et Biophysica Sinica. 2002, vol. 34, No. 4, pp. 411-417.
Hermans, Monique M.P., et al., "Human lysosomal .alpha.-glucosidase: functional characterization of the glycosylation sites", Biochemical Journal, vol. 289, Part 3, 1993, pp. 681-686.

(Continued)

*Primary Examiner* — Stephen L Rawlings
(74) *Attorney, Agent, or Firm* — McCarter & English, LLP

(57) ABSTRACT

An object of the present invention is to develop and provide a lung cancer differential marker with which lung cancer can be diagnosed conveniently and highly sensitively without depending only on increase or decrease in protein expression level between cancer patients and healthy persons. Another object of the present invention is to develop and provide a glycan marker capable of distinguishing histological types of lung cancer. Of serum glycoproteins, glycopeptide and glycoprotein groups whose glycan structures were altered specifically in lung cancer cell culture supernatants were identified, and they are provided as lung cancer differential markers.

4 Claims, 10 Drawing Sheets

Specification includes a Sequence Listing.

(56) References Cited

OTHER PUBLICATIONS

Ueda, Koji, et al., "Search for Sugar Chain-Targeting Tumor Marker for Lung Cancer", Experimental Medicine, 2007, vol. 25, No. 17, pp. 2747-2753.
Narimatsu, Hisashi, et al., "A strategy for discovery of cancer glyco-biomarkers in serum using newly developed technologies for glycoproteomics", FEBS Journal, 2010, vol. 277, No. 1, pp. 95-105.
Kishnani, Priya Sunil, et al., "Chinese Hamster Ovary Cell-Derived Recombinant Human Acid .alpha.-Glucosidase in Infantile-Onset Pompe Disease", The Journal of Pediatrics, 2006, vol. 149, No. 1, pp. 89-97.
Iwaki, Jun, et al., "Identification of glyco-biomarker candidates from non-small/small lung cancer cancer cell lines with advanced glycoproteomics", Annual Meeting of the Japanese Biochemical Society, 2012, 3 Pages—English translation of portion of abstract provided.
International Search Report—5 Pages.
Moss, Adrian C , el al., "SCG3 Transcript in Peripheral Blood is a Prognostic Biomarker for REST-Deficient Small Cell Lung Cancer", Clinical Cancer Research, Jan. 1, 2009, vol. 15, pp. 274-283.
European Search Report for co-pending European Patent Application No. 11825097.6, dated Oct. 19, 2016—6 Pages.
Regan, Ciaran M, "Regulation of Neural Cell Adhesion Molecule Sialylation State", international Journal of Biochemistry, 1991, vol. 23, No. 5/6, pp. 513-523.
European Search Report, dated Dec. 13, 2018 based on European co-pending Application No. 18194507.2—6 Pages.
Tajiri, Michiko, et al. "Differential Analysis of Site-Specific Glycans on Plasma and Cellular Fibronectins: Application of a Hydrophilic Affinity Method for Glycopeptide Enrichment", Glycobiology, 2005, vol. 15, No. 12, pp. 1332-1340.
Iwaki, Jun, et al., "Identification of glyco-biomarker candidates from non-small/small lung cancer cell lines with advanced glycoproteomics", Annual Meeting of the Japanese Biochemical Society, 2010, 3 Pages—English translation of portion of abstract provided.

* cited by examiner

AAL lectin blot

Sc   Ad

Anti-secretogranin III antibody

NHS  Sc  Ad

SEQUENCE LISTING

<160> NUMBER OF SEQ ID NOS: 235

<210> SEQ ID NO 1
<211> LENGTH: 8
<212> TYPE: PRT
<213> ORGANISM: Homo sapiens

<400> SEQUENCE: 1

Gln Val Val Glu Asn Met Thr Arg
1               5

<210> SEQ ID NO 2
<211> LENGTH: 15
<212> TYPE: PRT
<213> ORGANISM: Homo sapiens

<400> SEQUENCE: 2

Gly Val Phe Ile Thr Asn Glu Thr Gly Gln Pro Leu Ile Gly Lys
1               5                   10                  15

<210> SEQ ID NO 3
<211> LENGTH: 21
<212> TYPE: PRT
<213> ORGANISM: Homo sapiens

<400> SEQUENCE: 3

Gly Ala Tyr Thr Gln Val Ile Phe Leu Ala Arg Asn Asn Thr Ile Val
1               5                   10                  15

Asn Glu Leu Val Arg
            20

<210> SEQ ID NO 4
<211> LENGTH: 19
<212> TYPE: PRT
<213> ORGANISM: Homo sapiens

<400> SEQUENCE: 4

Asp Val Gln Ile Ile Val Phe Pro Glu Asp Gly Ile His Gly Phe Asn
1               5                   10                  15

Phe Thr Arg

<210> SEQ ID NO 5
<211> LENGTH: 9
<212> TYPE: PRT
<213> ORGANISM: Homo sapiens

<400> SEQUENCE: 5

Phe Asn Asp Thr Glu Val Leu Gln Arg
1               5

<210> SEQ ID NO 6
<211> LENGTH: 31
<212> TYPE: PRT
<213> ORGANISM: Homo sapiens

<400> SEQUENCE: 6

Ser His Leu Ile Ile Ala Gln Val Ala Lys Asn Pro Val Gly Leu Ile
1               5                   10                  15

Gly Ala Glu Asn Ala Thr Gly Glu Thr Asp Pro Ser His Ser Lys
            20                  25                  30

<210> SEQ ID NO 7
<211> LENGTH: 24

```
<212> TYPE: PRT
<213> ORGANISM: Homo sapiens

<400> SEQUENCE: 7

Asn Pro Val Gly Leu Ile Gly Ala Glu Asn Ala Thr Gly Glu Thr Asp
1               5                   10                  15

Pro Ser His Ser Lys Phe Leu Lys
            20

<210> SEQ ID NO 8
<211> LENGTH: 13
<212> TYPE: PRT
<213> ORGANISM: Homo sapiens

<400> SEQUENCE: 8

Tyr Tyr Lys Gly Ser Leu Ser Tyr Leu Asn Val Thr Arg
1               5                   10

<210> SEQ ID NO 9
<211> LENGTH: 21
<212> TYPE: PRT
<213> ORGANISM: Homo sapiens

<400> SEQUENCE: 9

Tyr Asn Pro Lys Tyr Ser Val Ala Asn Asp Thr Gly Phe Val Asp Ile
1               5                   10                  15

Pro Lys Gln Glu Lys
            20

<210> SEQ ID NO 10
<211> LENGTH: 14
<212> TYPE: PRT
<213> ORGANISM: Homo sapiens

<400> SEQUENCE: 10

Tyr Ser Val Ala Asn Asp Thr Gly Phe Val Asp Ile Pro Lys
1               5                   10

<210> SEQ ID NO 11
<211> LENGTH: 22
<212> TYPE: PRT
<213> ORGANISM: Homo sapiens

<400> SEQUENCE: 11

Tyr Arg Pro Glu Asn Ser Val Ala Asn Asp Thr Gly Phe Thr Val Val
1               5                   10                  15

Ala Pro Gly Lys Glu Lys
            20

<210> SEQ ID NO 12
<211> LENGTH: 22
<212> TYPE: PRT
<213> ORGANISM: Homo sapiens

<400> SEQUENCE: 12

Asn Leu Asp His Gly Val Leu Val Val Gly Tyr Gly Phe Glu Gly Ala
1               5                   10                  15

Asn Ser Asn Asn Ser Lys
            20

<210> SEQ ID NO 13
<211> LENGTH: 9
<212> TYPE: PRT
```

```
<213> ORGANISM: Homo sapiens

<400> SEQUENCE: 13

Gln Thr Leu Phe Phe Asn Gly Thr Arg
1               5

<210> SEQ ID NO 14
<211> LENGTH: 20
<212> TYPE: PRT
<213> ORGANISM: Homo sapiens

<400> SEQUENCE: 14

Ser Asn Thr Ser Gln Leu Ala Phe Leu Leu Tyr Asn Asp Gln Pro Pro
1               5                   10                  15

Gln Pro Ser Lys
            20

<210> SEQ ID NO 15
<211> LENGTH: 28
<212> TYPE: PRT
<213> ORGANISM: Homo sapiens

<400> SEQUENCE: 15

Gly Gly Asn Ser Asn Gly Ala Leu Cys His Phe Pro Phe Leu Tyr Asn
1               5                   10                  15

Asn His Asn Tyr Thr Asp Cys Thr Ser Glu Gly Arg
            20                  25

<210> SEQ ID NO 16
<211> LENGTH: 18
<212> TYPE: PRT
<213> ORGANISM: Homo sapiens

<400> SEQUENCE: 16

Asp Gln Cys Ile Val Asp Asp Ile Thr Tyr Asn Val Asn Asp Thr Phe
1               5                   10                  15

His Lys

<210> SEQ ID NO 17
<211> LENGTH: 17
<212> TYPE: PRT
<213> ORGANISM: Homo sapiens

<400> SEQUENCE: 17

Arg His Glu Glu Gly His Met Leu Asn Cys Thr Cys Phe Gly Gln Gly
1               5                   10                  15

Arg

<210> SEQ ID NO 18
<211> LENGTH: 16
<212> TYPE: PRT
<213> ORGANISM: Homo sapiens

<400> SEQUENCE: 18

His Glu Glu Gly His Met Leu Asn Cys Thr Cys Phe Gly Gln Gly Arg
1               5                   10                  15

<210> SEQ ID NO 19
<211> LENGTH: 32
<212> TYPE: PRT
<213> ORGANISM: Homo sapiens

<400> SEQUENCE: 19
```

```
Glu Ser Lys Pro Leu Thr Ala Gln Gln Thr Thr Lys Leu Asp Ala Pro
 1               5                  10                  15

Thr Asn Leu Gln Phe Val Asn Glu Thr Asp Ser Thr Val Leu Val Arg
                20                  25                  30
```

<210> SEQ ID NO 20
<211> LENGTH: 20
<212> TYPE: PRT
<213> ORGANISM: Homo sapiens

<400> SEQUENCE: 20

```
Leu Asp Ala Pro Thr Asn Leu Gln Phe Val Asn Glu Thr Asp Ser Thr
 1               5                  10                  15

Val Leu Val Arg
                20
```

<210> SEQ ID NO 21
<211> LENGTH: 13
<212> TYPE: PRT
<213> ORGANISM: Homo sapiens

<400> SEQUENCE: 21

```
Trp Thr Pro Leu Asn Ser Ser Thr Ile Ile Gly Tyr Arg
 1               5                  10
```

<210> SEQ ID NO 22
<211> LENGTH: 21
<212> TYPE: PRT
<213> ORGANISM: Homo sapiens

<400> SEQUENCE: 22

```
Ala Asp Val Gly Gly Glu Ala Ala Gly Thr Ser Ile Asn His Ser Gln
 1               5                  10                  15

Ala Val Leu Gln Arg
                20
```

<210> SEQ ID NO 23
<211> LENGTH: 10
<212> TYPE: PRT
<213> ORGANISM: Homo sapiens

<400> SEQUENCE: 23

```
Gln Gly Asn Ala Ser Asp Val Val Leu Arg
 1               5                  10
```

<210> SEQ ID NO 24
<211> LENGTH: 12
<212> TYPE: PRT
<213> ORGANISM: Homo sapiens

<400> SEQUENCE: 24

```
Phe Phe Asp Val Asn Gly Ser Ala Phe Leu Pro Arg
 1               5                  10
```

<210> SEQ ID NO 25
<211> LENGTH: 19
<212> TYPE: PRT
<213> ORGANISM: Homo sapiens

<400> SEQUENCE: 25

```
Ser Leu Leu Glu Phe Asn Thr Thr Val Ser Cys Asp Gln Gln Gly Thr
 1               5                  10                  15
```

Asn His Arg

<210> SEQ ID NO 26
<211> LENGTH: 17
<212> TYPE: PRT
<213> ORGANISM: Homo sapiens

<400> SEQUENCE: 26

Met Ser Val Ile Asn Phe Glu Cys Asn Lys Thr Ala Gly Asn Asp Gly
1               5                   10                  15

Lys

<210> SEQ ID NO 27
<211> LENGTH: 19
<212> TYPE: PRT
<213> ORGANISM: Homo sapiens

<400> SEQUENCE: 27

Thr Asn Ile Thr Leu Val Cys Lys Pro Gly Asp Leu Glu Ser Ala Pro
1               5                   10                  15

Val Leu Arg

<210> SEQ ID NO 28
<211> LENGTH: 20
<212> TYPE: PRT
<213> ORGANISM: Homo sapiens

<400> SEQUENCE: 28

Gly Tyr Pro Cys Gly Gly Asn Lys Thr Ala Ser Ser Val Ile Glu Leu
1               5                   10                  15

Thr Cys Thr Lys
            20

<210> SEQ ID NO 29
<211> LENGTH: 11
<212> TYPE: PRT
<213> ORGANISM: Homo sapiens

<400> SEQUENCE: 29

Gly Leu Cys Val Asn Ala Ser Ala Val Ser Arg
1               5                   10

<210> SEQ ID NO 30
<211> LENGTH: 21
<212> TYPE: PRT
<213> ORGANISM: Homo sapiens

<400> SEQUENCE: 30

Tyr Lys Val Asp Tyr Glu Ser Gln Ser Thr Asp Thr Gln Asn Phe Ser
1               5                   10                  15

Ser Glu Ser Lys Arg
            20

<210> SEQ ID NO 31
<211> LENGTH: 32
<212> TYPE: PRT
<213> ORGANISM: Homo sapiens

<400> SEQUENCE: 31

Asp Gly Pro Cys Glu Phe Ala Pro Val Val Val Pro Pro Arg Ser
1               5                   10                  15

Val His Asn Val Thr Gly Ala Gln Val Gly Leu Ser Cys Glu Val Arg

-continued

<210> SEQ ID NO 32
<211> LENGTH: 17
<212> TYPE: PRT
<213> ORGANISM: Homo sapiens

<400> SEQUENCE: 32

Ser Val His Asn Val Thr Gly Ala Gln Val Gly Leu Ser Cys Glu Val
1               5                   10                  15
Arg

<210> SEQ ID NO 33
<211> LENGTH: 16
<212> TYPE: PRT
<213> ORGANISM: Homo sapiens

<400> SEQUENCE: 33

Thr Ile Leu Val Asp Asn Asn Thr Trp Asn Asn Thr His Ile Ser Arg
1               5                   10                  15

<210> SEQ ID NO 34
<211> LENGTH: 22
<212> TYPE: PRT
<213> ORGANISM: Homo sapiens

<400> SEQUENCE: 34

Ile Leu Thr Ala Asp Asn Gln Thr Tyr Met Ala Val Gln Gly Ser Thr
1               5                   10                  15
Ala Tyr Leu Leu Cys Lys
            20

<210> SEQ ID NO 35
<211> LENGTH: 17
<212> TYPE: PRT
<213> ORGANISM: Homo sapiens

<400> SEQUENCE: 35

Trp Tyr Ser Leu Gly Lys Val Pro Gly Asn Gln Thr Ser Thr Thr Leu
1               5                   10                  15
Lys

<210> SEQ ID NO 36
<211> LENGTH: 36
<212> TYPE: PRT
<213> ORGANISM: Homo sapiens

<400> SEQUENCE: 36

Val Gln Trp Arg Pro Gln Gly Thr Arg Gly Pro Trp Gln Glu Gln Ile
1               5                   10                  15
Val Ser Asp Pro Phe Leu Val Val Ser Asn Thr Ser Thr Phe Val Pro
            20                  25                  30
Tyr Glu Ile Lys
        35

<210> SEQ ID NO 37
<211> LENGTH: 12
<212> TYPE: PRT
<213> ORGANISM: Homo sapiens

<400> SEQUENCE: 37

Thr His Asn Leu Thr Asp Leu Ser Pro His Leu Arg

```
1               5                   10
```

<210> SEQ ID NO 38
<211> LENGTH: 21
<212> TYPE: PRT
<213> ORGANISM: Homo sapiens

<400> SEQUENCE: 38

```
Phe Asn Pro Asn Ile Ser Trp Gln Pro Ile Pro Val His Thr Val Pro
1               5                   10                  15

Ile Thr Glu Asp Arg
            20
```

<210> SEQ ID NO 39
<211> LENGTH: 20
<212> TYPE: PRT
<213> ORGANISM: Homo sapiens

<400> SEQUENCE: 39

```
Tyr Glu Gln Leu Gln Asn Glu Thr Arg Gln Thr Pro Glu Tyr Gln Asn
1               5                   10                  15

Glu Ser Ser Arg
            20
```

<210> SEQ ID NO 40
<211> LENGTH: 11
<212> TYPE: PRT
<213> ORGANISM: Homo sapiens

<400> SEQUENCE: 40

```
Gln Thr Pro Glu Tyr Gln Asn Glu Ser Ser Arg
1               5                   10
```

<210> SEQ ID NO 41
<211> LENGTH: 20
<212> TYPE: PRT
<213> ORGANISM: Homo sapiens

<400> SEQUENCE: 41

```
Cys Gly Leu Ser Gln Ser Gln Gly Asn Leu Ser His Val Asp Trp Phe
1               5                   10                  15

Ser Val His Lys
            20
```

<210> SEQ ID NO 42
<211> LENGTH: 13
<212> TYPE: PRT
<213> ORGANISM: Homo sapiens

<400> SEQUENCE: 42

```
Cys Val Ala Ser Val Pro Ser Ile Pro Gly Leu Asn Arg
1               5                   10
```

<210> SEQ ID NO 43
<211> LENGTH: 20
<212> TYPE: PRT
<213> ORGANISM: Homo sapiens

<400> SEQUENCE: 43

```
Trp Cys Ala Thr Ser Asp Pro Glu Gln His Lys Cys Gly Asn Met Ser
1               5                   10                  15

Glu Ala Phe Arg
            20
```

```
<210> SEQ ID NO 44
<211> LENGTH: 23
<212> TYPE: PRT
<213> ORGANISM: Homo sapiens

<400> SEQUENCE: 44

Asp Cys Asp Val Leu Thr Ala Val Ser Glu Phe Phe Asn Ala Ser Cys
1               5                   10                  15

Val Pro Val Asn Asn Pro Lys
            20

<210> SEQ ID NO 45
<211> LENGTH: 17
<212> TYPE: PRT
<213> ORGANISM: Homo sapiens

<400> SEQUENCE: 45

Gly Ser Ser Val Ile Leu Asn Cys Ser Ala Tyr Ser Glu Pro Ser Pro
1               5                   10                  15

Lys

<210> SEQ ID NO 46
<211> LENGTH: 23
<212> TYPE: PRT
<213> ORGANISM: Homo sapiens

<400> SEQUENCE: 46

Val Ile Lys Leu Pro Ser Gly Met Leu Val Ile Ser Asn Ala Thr Glu
1               5                   10                  15

Gly Asp Gly Gly Leu Tyr Arg
            20

<210> SEQ ID NO 47
<211> LENGTH: 19
<212> TYPE: PRT
<213> ORGANISM: Homo sapiens

<400> SEQUENCE: 47

Thr Pro Ala Ser Asp Pro His Gly Asp Asn Leu Thr Tyr Ser Val Phe
1               5                   10                  15

Tyr Thr Lys

<210> SEQ ID NO 48
<211> LENGTH: 11
<212> TYPE: PRT
<213> ORGANISM: Homo sapiens

<400> SEQUENCE: 48

Thr Ser Thr Arg Asn Ile Ser Ser Glu Glu Lys
1               5                   10

<210> SEQ ID NO 49
<211> LENGTH: 14
<212> TYPE: PRT
<213> ORGANISM: Homo sapiens

<400> SEQUENCE: 49

Asp Gly Gln Leu Leu Pro Ser Ser Asn Tyr Ser Asn Ile Lys
1               5                   10

<210> SEQ ID NO 50
```

```
<211> LENGTH: 30
<212> TYPE: PRT
<213> ORGANISM: Homo sapiens

<400> SEQUENCE: 50

Ile Tyr Asn Thr Pro Ser Ala Ser Tyr Leu Glu Val Thr Pro Asp Ser
1               5                   10                  15

Glu Asn Asp Phe Gly Asn Tyr Asn Cys Thr Ala Val Asn Arg
            20                  25                  30

<210> SEQ ID NO 51
<211> LENGTH: 13
<212> TYPE: PRT
<213> ORGANISM: Homo sapiens

<400> SEQUENCE: 51

Ala Asn Val Ser Asn Ala Gly Leu Pro Gly Asp Phe Arg
1               5                   10

<210> SEQ ID NO 52
<211> LENGTH: 19
<212> TYPE: PRT
<213> ORGANISM: Homo sapiens

<400> SEQUENCE: 52

Val Ala Glu Leu Glu Asp Glu Lys Ser Leu Leu His Asn Glu Thr Ser
1               5                   10                  15

Ala His Arg

<210> SEQ ID NO 53
<211> LENGTH: 23
<212> TYPE: PRT
<213> ORGANISM: Homo sapiens

<400> SEQUENCE: 53

Ala Leu Pro Gly Gly Ala Asp Asn Ala Ser Val Ala Ser Gly Ala Ala
1               5                   10                  15

Ala Ser Pro Gly Pro Gln Arg
            20

<210> SEQ ID NO 54
<211> LENGTH: 13
<212> TYPE: PRT
<213> ORGANISM: Homo sapiens

<400> SEQUENCE: 54

Ala Tyr Trp Pro Asp Val Ile His Ser Phe Pro Asn Arg
1               5                   10

<210> SEQ ID NO 55
<211> LENGTH: 18
<212> TYPE: PRT
<213> ORGANISM: Homo sapiens

<400> SEQUENCE: 55

Gln Asp Gln Gln Leu Gln Asn Cys Thr Glu Pro Gly Glu Gln Pro Ser
1               5                   10                  15

Pro Lys

<210> SEQ ID NO 56
<211> LENGTH: 24
<212> TYPE: PRT
<213> ORGANISM: Homo sapiens
```

<400> SEQUENCE: 56

Lys Thr Tyr Pro Pro Glu Asn Lys Pro Gly Gln Ser Asn Tyr Ser Phe
1               5                   10                  15

Val Asp Asn Leu Asn Leu Leu Lys
            20

<210> SEQ ID NO 57
<211> LENGTH: 13
<212> TYPE: PRT
<213> ORGANISM: Homo sapiens

<400> SEQUENCE: 57

Asn Lys Leu Glu Lys Asn Ala Thr Asp Asn Ile Ser Lys
1               5                   10

<210> SEQ ID NO 58
<211> LENGTH: 13
<212> TYPE: PRT
<213> ORGANISM: Homo sapiens

<400> SEQUENCE: 58

Glu Ala Ser Ile Val Gly Glu Asn Glu Thr Tyr Pro Arg
1               5                   10

<210> SEQ ID NO 59
<211> LENGTH: 30
<212> TYPE: PRT
<213> ORGANISM: Homo sapiens

<400> SEQUENCE: 59

Leu Arg Asp Trp Phe Gln Leu Leu His Glu Asn Ser Lys Gln Asn Gly
1               5                   10                  15

Ser Ala Ser Ser Val Ala Gly Pro Ala Ser Gly Leu Asp Lys
            20                  25                  30

<210> SEQ ID NO 60
<211> LENGTH: 17
<212> TYPE: PRT
<213> ORGANISM: Homo sapiens

<400> SEQUENCE: 60

Gln Asn Gly Ser Ala Ser Ser Val Ala Gly Pro Ala Ser Gly Leu Asp
1               5                   10                  15

Lys

<210> SEQ ID NO 61
<211> LENGTH: 21
<212> TYPE: PRT
<213> ORGANISM: Homo sapiens

<400> SEQUENCE: 61

Leu Asp Cys Arg His Glu Asn Thr Ser Ser Pro Ile Gln Tyr Glu
1               5                   10                  15

Phe Ser Leu Thr Arg
            20

<210> SEQ ID NO 62
<211> LENGTH: 23
<212> TYPE: PRT
<213> ORGANISM: Homo sapiens

<400> SEQUENCE: 62

```
Gly Arg Ala Asp Asp Cys Ala Leu Pro Tyr Leu Gly Ala Ile Cys Tyr
1               5                   10                  15

Cys Asp Leu Phe Cys Asn Arg
            20
```

<210> SEQ ID NO 63
<211> LENGTH: 27
<212> TYPE: PRT
<213> ORGANISM: Homo sapiens

<400> SEQUENCE: 63

```
Ala Ile Asn Gln Gly Asn Tyr Gly Trp Gln Ala Gly Asn His Ser Ala
1               5                   10                  15

Phe Trp Gly Met Thr Leu Asp Glu Gly Ile Arg
            20                  25
```

<210> SEQ ID NO 64
<211> LENGTH: 13
<212> TYPE: PRT
<213> ORGANISM: Homo sapiens

<400> SEQUENCE: 64

```
Ser Leu Tyr Gly Lys Glu Asp Asn Asp Thr Leu Val Arg
1               5                   10
```

<210> SEQ ID NO 65
<211> LENGTH: 19
<212> TYPE: PRT
<213> ORGANISM: Homo sapiens

<400> SEQUENCE: 65

```
Thr Phe Thr Asp Lys Trp Glu Asp Tyr Pro Lys Ser Glu Asn Glu Ser
1               5                   10                  15

Asn Ile Arg
```

<210> SEQ ID NO 66
<211> LENGTH: 22
<212> TYPE: PRT
<213> ORGANISM: Homo sapiens

<400> SEQUENCE: 66

```
Cys Ser Ala Ser Val Leu Pro Val Asp Val Gln Thr Leu Asn Ser Ser
1               5                   10                  15

Gly Pro Pro Phe Gly Lys
            20
```

<210> SEQ ID NO 67
<211> LENGTH: 21
<212> TYPE: PRT
<213> ORGANISM: Homo sapiens

<400> SEQUENCE: 67

```
Leu Val Val Gln Ser Ser Ile Asp Ser Ser Ala Phe Lys His Asn Gly
1               5                   10                  15

Thr Val Glu Cys Lys
            20
```

<210> SEQ ID NO 68
<211> LENGTH: 16
<212> TYPE: PRT
<213> ORGANISM: Homo sapiens

```
<400> SEQUENCE: 68

Leu Val Gly Gly Pro Val Ala Gly Gly Asp Pro Asn Gln Thr Ile Arg
1               5                   10                  15

<210> SEQ ID NO 69
<211> LENGTH: 14
<212> TYPE: PRT
<213> ORGANISM: Homo sapiens

<400> SEQUENCE: 69

Leu Asn Leu Thr Ser Pro Asp Leu Phe Trp Leu Val Phe Arg
1               5                   10

<210> SEQ ID NO 70
<211> LENGTH: 18
<212> TYPE: PRT
<213> ORGANISM: Homo sapiens

<400> SEQUENCE: 70

Val Trp Gln Gly His Ala Asn Ala Ser Phe Cys Pro His Gly Tyr Gly
1               5                   10                  15

Cys Arg

<210> SEQ ID NO 71
<211> LENGTH: 48
<212> TYPE: PRT
<213> ORGANISM: Homo sapiens

<400> SEQUENCE: 71

Thr Ile Pro Pro Asp Cys Leu Leu Cys Gln Pro Gln Thr Phe Gly Cys
1               5                   10                  15

His Pro Leu Val Gly Cys Glu Glu Cys Asn Cys Ser Gly Pro Gly Ile
            20                  25                  30

Gln Glu Leu Thr Asp Pro Thr Cys Asp Thr Asp Ser Gly Gln Cys Lys
        35                  40                  45

<210> SEQ ID NO 72
<211> LENGTH: 20
<212> TYPE: PRT
<213> ORGANISM: Homo sapiens

<400> SEQUENCE: 72

Cys Glu Ile Cys Ala Pro Gly Phe Tyr Gly Asn Ala Leu Leu Pro Gly
1               5                   10                  15

Asn Cys Thr Arg
            20

<210> SEQ ID NO 73
<211> LENGTH: 11
<212> TYPE: PRT
<213> ORGANISM: Homo sapiens

<400> SEQUENCE: 73

Gly Ile Asn Ala Ser Ser Met Ala Trp Ala Arg
1               5                   10

<210> SEQ ID NO 74
<211> LENGTH: 16
<212> TYPE: PRT
<213> ORGANISM: Homo sapiens

<400> SEQUENCE: 74
```

Leu His Arg Leu Asn Ala Ser Ile Ala Asp Leu Gln Ser Gln Leu Arg
1               5                   10                  15

<210> SEQ ID NO 75
<211> LENGTH: 27
<212> TYPE: PRT
<213> ORGANISM: Homo sapiens

<400> SEQUENCE: 75

Thr Leu Ser Glu Leu Met Ser Gln Thr Gly His Leu Gly Leu Ala Asn
1               5                   10                  15

Ala Ser Ala Pro Ser Gly Glu Gln Leu Leu Arg
            20                  25

<210> SEQ ID NO 76
<211> LENGTH: 13
<212> TYPE: PRT
<213> ORGANISM: Homo sapiens

<400> SEQUENCE: 76

Asp Asn Ala Thr Leu Gln Ala Thr Leu His Ala Ala Arg
1               5                   10

<210> SEQ ID NO 77
<211> LENGTH: 34
<212> TYPE: PRT
<213> ORGANISM: Homo sapiens

<400> SEQUENCE: 77

Leu Val Glu Ala Ala Glu Ala His Ala Gln Gln Leu Gly Gln Leu Ala
1               5                   10                  15

Leu Asn Leu Ser Ser Ile Ile Leu Asp Val Asn Gln Asp Arg Leu Thr
            20                  25                  30

Gln Arg

<210> SEQ ID NO 78
<211> LENGTH: 27
<212> TYPE: PRT
<213> ORGANISM: Homo sapiens

<400> SEQUENCE: 78

Gln Gly Leu Val Asp Arg Ala Gln Gln Leu Leu Ala Asn Ser Thr Ala
1               5                   10                  15

Leu Glu Glu Ala Met Leu Gln Glu Gln Gln Arg
            20                  25

<210> SEQ ID NO 79
<211> LENGTH: 15
<212> TYPE: PRT
<213> ORGANISM: Homo sapiens

<400> SEQUENCE: 79

Gly Val His Asn Ala Ser Leu Ala Leu Ser Ala Ser Ile Gly Arg
1               5                   10                  15

<210> SEQ ID NO 80
<211> LENGTH: 18
<212> TYPE: PRT
<213> ORGANISM: Homo sapiens

<400> SEQUENCE: 80

Leu Asn Thr Thr Gly Val Ser Ala Gly Cys Thr Ala Asp Leu Leu Val
1               5                   10                  15

Gly Arg

<210> SEQ ID NO 81
<211> LENGTH: 31
<212> TYPE: PRT
<213> ORGANISM: Homo sapiens

<400> SEQUENCE: 81

Val Phe Asp Leu Gln Gln Asn Leu Gly Ser Val Asn Val Ser Thr Gly
1               5                   10                  15

Cys Ala Pro Ala Leu Gln Ala Gln Thr Pro Gly Leu Gly Pro Arg
            20                  25                  30

<210> SEQ ID NO 82
<211> LENGTH: 23
<212> TYPE: PRT
<213> ORGANISM: Homo sapiens

<400> SEQUENCE: 82

Lys Cys Val Cys Asn Tyr Leu Gly Thr Val Gln Glu His Cys Asn Gly
1               5                   10                  15

Ser Asp Cys Gln Cys Asp Lys
            20

<210> SEQ ID NO 83
<211> LENGTH: 13
<212> TYPE: PRT
<213> ORGANISM: Homo sapiens

<400> SEQUENCE: 83

Leu Ser Asp Thr Thr Ser Gln Ser Asn Ser Thr Ala Lys
1               5                   10

<210> SEQ ID NO 84
<211> LENGTH: 14
<212> TYPE: PRT
<213> ORGANISM: Homo sapiens

<400> SEQUENCE: 84

Gln Ser Ala Glu Asp Ile Leu Leu Lys Thr Asn Ala Thr Lys
1               5                   10

<210> SEQ ID NO 85
<211> LENGTH: 36
<212> TYPE: PRT
<213> ORGANISM: Homo sapiens

<400> SEQUENCE: 85

Ala Ile Lys Gln Ala Asp Glu Asp Ile Gln Gly Thr Gln Asn Leu Leu
1               5                   10                  15

Thr Ser Ile Glu Ser Glu Thr Ala Ala Ser Glu Glu Thr Leu Phe Asn
            20                  25                  30

Ala Ser Gln Arg
            35

<210> SEQ ID NO 86
<211> LENGTH: 14
<212> TYPE: PRT
<213> ORGANISM: Homo sapiens

<400> SEQUENCE: 86

Gly Lys Glu Gly His Phe Tyr Tyr Asn Ile Ser Glu Val Lys

-continued

<210> SEQ ID NO 87
<211> LENGTH: 14
<212> TYPE: PRT
<213> ORGANISM: Homo sapiens

<400> SEQUENCE: 87

Met Lys Val Ser Asn Val Ser Cys Gln Ala Ser Val Ser Arg
1               5                   10

<210> SEQ ID NO 88
<211> LENGTH: 12
<212> TYPE: PRT
<213> ORGANISM: Homo sapiens

<400> SEQUENCE: 88

Val Ser Asn Val Ser Cys Gln Ala Ser Val Ser Arg
1               5                   10

<210> SEQ ID NO 89
<211> LENGTH: 16
<212> TYPE: PRT
<213> ORGANISM: Homo sapiens

<400> SEQUENCE: 89

Gly Ala Phe Phe Pro Leu Thr Glu Arg Asn Trp Ser Leu Pro Asn Arg
1               5                   10                  15

<210> SEQ ID NO 90
<211> LENGTH: 23
<212> TYPE: PRT
<213> ORGANISM: Homo sapiens

<400> SEQUENCE: 90

Phe Arg Ile Tyr Ser Asn His Ser Ala Leu Glu Ser Leu Ala Leu Ile
1               5                   10                  15

Pro Leu Gln Ala Pro Leu Lys
            20

<210> SEQ ID NO 91
<211> LENGTH: 16
<212> TYPE: PRT
<213> ORGANISM: Homo sapiens

<400> SEQUENCE: 91

Gly Ala Phe Phe Pro Leu Thr Glu Arg Asn Trp Ser Leu Pro Asn Arg
1               5                   10                  15

<210> SEQ ID NO 92
<211> LENGTH: 20
<212> TYPE: PRT
<213> ORGANISM: Homo sapiens

<400> SEQUENCE: 92

Lys Leu Gly Asp Cys Ile Ser Glu Asp Ser Tyr Pro Asp Gly Asn Ile
1               5                   10                  15

Thr Trp Tyr Arg
            20

<210> SEQ ID NO 93
<211> LENGTH: 12
<212> TYPE: PRT
<213> ORGANISM: Homo sapiens

<400> SEQUENCE: 93

Asn Ala Ile Lys Glu Gly Asp Asn Ile Thr Leu Lys
1               5                   10

<210> SEQ ID NO 94
<211> LENGTH: 8
<212> TYPE: PRT
<213> ORGANISM: Homo sapiens

<400> SEQUENCE: 94

Glu Gly Asp Asn Ile Thr Leu Lys
1               5

<210> SEQ ID NO 95
<211> LENGTH: 12
<212> TYPE: PRT
<213> ORGANISM: Homo sapiens

<400> SEQUENCE: 95

Asn Ala Thr Val Val Trp Met Lys Asp Asn Ile Arg
1               5                   10

<210> SEQ ID NO 96
<211> LENGTH: 25
<212> TYPE: PRT
<213> ORGANISM: Homo sapiens

<400> SEQUENCE: 96

Tyr Tyr Ser Lys Ile Ile Ile Ser Pro Glu Glu Asn Val Thr Leu Thr
1               5                   10                  15

Cys Thr Ala Glu Asn Gln Leu Glu Arg
            20                  25

<210> SEQ ID NO 97
<211> LENGTH: 11
<212> TYPE: PRT
<213> ORGANISM: Homo sapiens

<400> SEQUENCE: 97

Glu Ala Ser Gln Asn Ile Thr Tyr Ile Cys Lys
1               5                   10

<210> SEQ ID NO 98
<211> LENGTH: 11
<212> TYPE: PRT
<213> ORGANISM: Homo sapiens

<400> SEQUENCE: 98

Leu Glu Asn Ile Thr Asn Pro Trp Ser Pro Arg
1               5                   10

<210> SEQ ID NO 99
<211> LENGTH: 30
<212> TYPE: PRT
<213> ORGANISM: Homo sapiens

<400> SEQUENCE: 99

Leu Val Gln Leu Phe Pro Asn Asp Thr Ser Leu Lys Asn Asp Leu Gly
1               5                   10                  15

Val Gly Tyr Leu Leu Ile Gly Asp Asn Asp Asn Ala Lys Lys
            20                  25                  30

<210> SEQ ID NO 100
<211> LENGTH: 13
<212> TYPE: PRT
<213> ORGANISM: Homo sapiens

<400> SEQUENCE: 100

Asp Phe Arg Tyr Asn Leu Ser Glu Val Leu Gln Gly Lys
1               5                   10

<210> SEQ ID NO 101
<211> LENGTH: 17
<212> TYPE: PRT
<213> ORGANISM: Homo sapiens

<400> SEQUENCE: 101

His Leu Glu Leu Ala Gly Glu Asn Pro Ser Ser Asp Ile Asn Cys Thr
1               5                   10                  15

Lys

<210> SEQ ID NO 102
<211> LENGTH: 18
<212> TYPE: PRT
<213> ORGANISM: Homo sapiens

<400> SEQUENCE: 102

Trp Thr Pro Asp Asp Tyr Ile Asn Met Thr Ser Asp Cys Ser Ser Phe
1               5                   10                  15

Ile Lys

<210> SEQ ID NO 103
<211> LENGTH: 28
<212> TYPE: PRT
<213> ORGANISM: Homo sapiens

<400> SEQUENCE: 103

Ala Ala Thr Ser Arg Pro Glu Arg Val Trp Pro Asp Gly Val Ile Pro
1               5                   10                  15

Phe Val Ile Gly Gly Asn Phe Thr Gly Ser Gln Arg
            20                  25

<210> SEQ ID NO 104
<211> LENGTH: 20
<212> TYPE: PRT
<213> ORGANISM: Homo sapiens

<400> SEQUENCE: 104

Ile Ser Val Thr Pro Gly Glu Lys Ile Ile Leu Asn Phe Thr Ser Leu
1               5                   10                  15

Asp Leu Tyr Arg
            20

<210> SEQ ID NO 105
<211> LENGTH: 12
<212> TYPE: PRT
<213> ORGANISM: Homo sapiens

<400> SEQUENCE: 105

Leu Asn Gly Ser Ile Thr Ser Pro Gly Trp Pro Lys
1               5                   10

<210> SEQ ID NO 106
<211> LENGTH: 21
<212> TYPE: PRT

```
<213> ORGANISM: Homo sapiens

<400> SEQUENCE: 106

Ile His Gly Gln Glu Leu Pro Phe Glu Ala Val Val Leu Asn Lys Thr
1               5                   10                  15

Ser Gly Glu Gly Arg
            20

<210> SEQ ID NO 107
<211> LENGTH: 13
<212> TYPE: PRT
<213> ORGANISM: Homo sapiens

<400> SEQUENCE: 107

Asn Leu Thr Asp Gln Phe Thr Ile Thr Met Trp Met Lys
1               5                   10

<210> SEQ ID NO 108
<211> LENGTH: 14
<212> TYPE: PRT
<213> ORGANISM: Homo sapiens

<400> SEQUENCE: 108

Gln Glu Cys Leu Glu Leu Asn His Ser Glu Leu His Gln Arg
1               5                   10

<210> SEQ ID NO 109
<211> LENGTH: 21
<212> TYPE: PRT
<213> ORGANISM: Homo sapiens

<400> SEQUENCE: 109

His Leu Asp Ala Thr Asn Ser Thr Ala Gly Tyr Ser Ile Tyr Gly Val
1               5                   10                  15

Gly Ser Met Ser Arg
            20

<210> SEQ ID NO 110
<211> LENGTH: 22
<212> TYPE: PRT
<213> ORGANISM: Homo sapiens

<400> SEQUENCE: 110

Leu Leu Asn Thr Thr Asp Val Tyr Leu Leu Pro Ser Leu Asn Pro Asp
1               5                   10                  15

Gly Phe Glu Arg Ala Arg
            20

<210> SEQ ID NO 111
<211> LENGTH: 11
<212> TYPE: PRT
<213> ORGANISM: Homo sapiens

<400> SEQUENCE: 111

Arg Phe Ala Asn Glu Tyr Pro Asn Ile Thr Arg
1               5                   10

<210> SEQ ID NO 112
<211> LENGTH: 22
<212> TYPE: PRT
<213> ORGANISM: Homo sapiens

<400> SEQUENCE: 112
```

```
His Ile Trp Ser Leu Glu Ile Ser Asn Lys Pro Asn Val Ser Glu Pro
1               5                   10                  15

Glu Glu Pro Lys Ile Arg
            20

<210> SEQ ID NO 113
<211> LENGTH: 18
<212> TYPE: PRT
<213> ORGANISM: Homo sapiens

<400> SEQUENCE: 113

Gly Lys Asp Leu Asp Thr Asp Phe Thr Asn Asn Ala Ser Gln Pro Glu
1               5                   10                  15

Thr Lys

<210> SEQ ID NO 114
<211> LENGTH: 13
<212> TYPE: PRT
<213> ORGANISM: Homo sapiens

<400> SEQUENCE: 114

Gly Arg Asp Ile Tyr Thr Phe Asp Gly Ala Leu Asn Lys
1               5                   10

<210> SEQ ID NO 115
<211> LENGTH: 22
<212> TYPE: PRT
<213> ORGANISM: Homo sapiens

<400> SEQUENCE: 115

Asp Ile Tyr Thr Phe Asp Gly Ala Leu Asn Lys Ser Thr Val Pro Thr
1               5                   10                  15

Asp Phe Ser Ser Ala Lys
            20

<210> SEQ ID NO 116
<211> LENGTH: 22
<212> TYPE: PRT
<213> ORGANISM: Homo sapiens

<400> SEQUENCE: 116

Met Asp Lys Ser Asp Ala Val Ser His Thr Gly Asn Tyr Thr Cys Glu
1               5                   10                  15

Val Thr Glu Leu Thr Arg
            20

<210> SEQ ID NO 117
<211> LENGTH: 18
<212> TYPE: PRT
<213> ORGANISM: Homo sapiens

<400> SEQUENCE: 117

Gln Gln Met Glu Asn Tyr Pro Lys Asn Asn His Thr Ala Ser Ile Leu
1               5                   10                  15

Asp Arg

<210> SEQ ID NO 118
<211> LENGTH: 10
<212> TYPE: PRT
<213> ORGANISM: Homo sapiens

<400> SEQUENCE: 118
```

```
Asn Asn His Thr Ala Ser Ile Leu Asp Arg
1               5                  10
```

<210> SEQ ID NO 119
<211> LENGTH: 22
<212> TYPE: PRT
<213> ORGANISM: Homo sapiens

<400> SEQUENCE: 119

```
Asn Arg Val Pro Asp Ser Cys Cys Ile Asn Val Thr Val Gly Cys Gly
1               5                   10                  15

Ile Asn Phe Asn Glu Lys
            20
```

<210> SEQ ID NO 120
<211> LENGTH: 21
<212> TYPE: PRT
<213> ORGANISM: Homo sapiens

<400> SEQUENCE: 120

```
Thr Phe Lys Asn Glu Ser Glu Asn Thr Cys Gln Asp Val Asp Glu Cys
1               5                   10                  15

Gln Gln Asn Pro Arg
            20
```

<210> SEQ ID NO 121
<211> LENGTH: 16
<212> TYPE: PRT
<213> ORGANISM: Homo sapiens

<400> SEQUENCE: 121

```
Arg Leu Ser Ala Val Asn Ser Ile Phe Leu Ser His Asn Asn Thr Lys
1               5                   10                  15
```

<210> SEQ ID NO 122
<211> LENGTH: 16
<212> TYPE: PRT
<213> ORGANISM: Homo sapiens

<400> SEQUENCE: 122

```
Arg Leu Ser Ala Val Asn Ser Ile Phe Leu Ser His Asn Asn Thr Lys
1               5                   10                  15
```

<210> SEQ ID NO 123
<211> LENGTH: 21
<212> TYPE: PRT
<213> ORGANISM: Homo sapiens

<400> SEQUENCE: 123

```
Thr Phe Lys Asn Glu Ser Glu Asn Thr Cys Gln Asp Val Asp Glu Cys
1               5                   10                  15

Gln Gln Asn Pro Arg
            20
```

<210> SEQ ID NO 124
<211> LENGTH: 16
<212> TYPE: PRT
<213> ORGANISM: Homo sapiens

<400> SEQUENCE: 124

```
Arg Leu Ser Ala Val Asn Ser Ile Phe Leu Ser His Asn Asn Thr Lys
1               5                   10                  15
```

```
<210> SEQ ID NO 125
<211> LENGTH: 12
<212> TYPE: PRT
<213> ORGANISM: Homo sapiens

<400> SEQUENCE: 125

Phe Leu Asn Asn Gly Thr Cys Thr Ala Glu Gly Lys
1               5                   10

<210> SEQ ID NO 126
<211> LENGTH: 19
<212> TYPE: PRT
<213> ORGANISM: Homo sapiens

<400> SEQUENCE: 126

Phe Lys Leu Ser Asp Leu Ser Ile Asn Ser Thr Glu Cys Leu His Val
1               5                   10                  15

His Cys Arg

<210> SEQ ID NO 127
<211> LENGTH: 17
<212> TYPE: PRT
<213> ORGANISM: Homo sapiens

<400> SEQUENCE: 127

Leu Ser Asp Leu Ser Ile Asn Ser Thr Glu Cys Leu His Val His Cys
1               5                   10                  15

Arg

<210> SEQ ID NO 128
<211> LENGTH: 26
<212> TYPE: PRT
<213> ORGANISM: Homo sapiens

<400> SEQUENCE: 128

Ser Ile Pro Ala Cys Val Pro Trp Ser Pro Tyr Leu Phe Gln Pro Asn
1               5                   10                  15

Asp Thr Cys Ile Val Ser Gly Trp Gly Arg
            20                  25

<210> SEQ ID NO 129
<211> LENGTH: 12
<212> TYPE: PRT
<213> ORGANISM: Homo sapiens

<400> SEQUENCE: 129

Leu Ile Ser Asn Cys Ser Lys Phe Tyr Gly Asn Arg
1               5                   10

<210> SEQ ID NO 130
<211> LENGTH: 17
<212> TYPE: PRT
<213> ORGANISM: Homo sapiens

<400> SEQUENCE: 130

Tyr Ser Val Glu Lys Phe Asn Asn Cys Thr Asn Asp Met Phe Leu Phe
1               5                   10                  15

Lys

<210> SEQ ID NO 131
<211> LENGTH: 15
<212> TYPE: PRT
<213> ORGANISM: Homo sapiens
```

<400> SEQUENCE: 131

Phe Asn Asn Cys Thr Asn Asp Met Phe Leu Phe Lys Glu Ser Arg
1               5                   10                  15

<210> SEQ ID NO 132
<211> LENGTH: 13
<212> TYPE: PRT
<213> ORGANISM: Homo sapiens

<400> SEQUENCE: 132

Leu Asp Asp Cys Asp Phe Gln Thr Asn His Thr Leu Lys
1               5                   10

<210> SEQ ID NO 133
<211> LENGTH: 26
<212> TYPE: PRT
<213> ORGANISM: Homo sapiens

<400> SEQUENCE: 133

Ser Leu Asp Arg Glu Ala Glu Thr Ile Lys Asn Gly Ile Tyr Asn Ile
1               5                   10                  15

Thr Val Leu Ala Ser Asp Gln Gly Gly Arg
            20                  25

<210> SEQ ID NO 134
<211> LENGTH: 8
<212> TYPE: PRT
<213> ORGANISM: Homo sapiens

<400> SEQUENCE: 134

Ala Ile Asn Asp Thr Ala Ala Arg
1               5

<210> SEQ ID NO 135
<211> LENGTH: 11
<212> TYPE: PRT
<213> ORGANISM: Homo sapiens

<400> SEQUENCE: 135

Val Leu Glu Ala Val Asn Gly Thr Asp Ala Arg
1               5                   10

<210> SEQ ID NO 136
<211> LENGTH: 14
<212> TYPE: PRT
<213> ORGANISM: Homo sapiens

<400> SEQUENCE: 136

Leu Gln Phe Asp Asp Asn Gly Thr Tyr Thr Cys Gln Val Lys
1               5                   10

<210> SEQ ID NO 137
<211> LENGTH: 21
<212> TYPE: PRT
<213> ORGANISM: Homo sapiens

<400> SEQUENCE: 137

Ala Ile Gly Gly Ile Asp Trp Asp Ser His Pro Phe Gly Tyr Asn Leu
1               5                   10                  15

Thr Leu Gln Ala Lys
            20

```
<210> SEQ ID NO 138
<211> LENGTH: 8
<212> TYPE: PRT
<213> ORGANISM: Homo sapiens

<400> SEQUENCE: 138

Gln Val Tyr Asn Leu Thr Val Arg
1               5

<210> SEQ ID NO 139
<211> LENGTH: 21
<212> TYPE: PRT
<213> ORGANISM: Homo sapiens

<400> SEQUENCE: 139

Ile Val Val Asn Val Ser Asp Thr Asn Asp His Ala Pro Trp Phe Thr
1               5                   10                  15

Ala Ser Ser Tyr Lys
            20

<210> SEQ ID NO 140
<211> LENGTH: 20
<212> TYPE: PRT
<213> ORGANISM: Homo sapiens

<400> SEQUENCE: 140

Gln Leu Leu His Lys Ile Asn Ser Ser Val Thr Asp Ile Glu Glu Ile
1               5                   10                  15

Ile Gly Val Arg
            20

<210> SEQ ID NO 141
<211> LENGTH: 9
<212> TYPE: PRT
<213> ORGANISM: Homo sapiens

<400> SEQUENCE: 141

Leu Asp Gly Ser Thr Asn Phe Thr Arg
1               5

<210> SEQ ID NO 142
<211> LENGTH: 15
<212> TYPE: PRT
<213> ORGANISM: Homo sapiens

<400> SEQUENCE: 142

Leu His Val Gly Asn Tyr Asn Gly Thr Ala Gly Asp Ala Leu Arg
1               5                   10                  15

<210> SEQ ID NO 143
<211> LENGTH: 35
<212> TYPE: PRT
<213> ORGANISM: Homo sapiens

<400> SEQUENCE: 143

Ile His Thr Pro Ser Leu His Val Asn Gly Ser Leu Ile Leu Pro Ile
1               5                   10                  15

Gly Ser Ile Lys Pro Leu Asp Phe Ser Leu Leu Asn Val Gln Asp Gln
            20                  25                  30

Glu Gly Arg
        35

<210> SEQ ID NO 144
```

<211> LENGTH: 19
<212> TYPE: PRT
<213> ORGANISM: Homo sapiens

<400> SEQUENCE: 144

Ile Val Tyr Asn Ile Thr Leu Pro Leu His Pro Asn Gln Gly Ile Ile
1               5                   10                  15
Glu His Arg

<210> SEQ ID NO 145
<211> LENGTH: 24
<212> TYPE: PRT
<213> ORGANISM: Homo sapiens

<400> SEQUENCE: 145

Ile Ser Gly Ser Glu Val Glu Leu Ser Glu Val Ser Asn Phe Thr
1               5                   10                  15
Met Glu Asp Ile Asn Asn Lys Lys
            20

<210> SEQ ID NO 146
<211> LENGTH: 9
<212> TYPE: PRT
<213> ORGANISM: Homo sapiens

<400> SEQUENCE: 146

Tyr Thr Ser Tyr Asn Val Ser Glu Lys
1               5

<210> SEQ ID NO 147
<211> LENGTH: 17
<212> TYPE: PRT
<213> ORGANISM: Homo sapiens

<400> SEQUENCE: 147

Val Ile Ile Asn Asp Thr Glu Asp Glu Pro Thr Leu Glu Phe Asp Lys
1               5                   10                  15
Lys

<210> SEQ ID NO 148
<211> LENGTH: 21
<212> TYPE: PRT
<213> ORGANISM: Homo sapiens

<400> SEQUENCE: 148

Leu Arg Ala Asn Gln Ser Trp Glu Asp Ser Asn Thr Asp Leu Val Pro
1               5                   10                  15
Ala Pro Ala Val Arg
            20

<210> SEQ ID NO 149
<211> LENGTH: 26
<212> TYPE: PRT
<213> ORGANISM: Homo sapiens

<400> SEQUENCE: 149

Ala Asn Gln Ser Trp Glu Asp Ser Asn Thr Asp Leu Val Pro Ala Pro
1               5                   10                  15
Ala Val Arg Ile Leu Thr Pro Glu Val Arg
            20                  25

<210> SEQ ID NO 150

```
<211> LENGTH: 12
<212> TYPE: PRT
<213> ORGANISM: Homo sapiens

<400> SEQUENCE: 150

Phe Gln Leu Leu Asn Phe Ser Ser Ser Glu Leu Lys
1               5                   10

<210> SEQ ID NO 151
<211> LENGTH: 13
<212> TYPE: PRT
<213> ORGANISM: Homo sapiens

<400> SEQUENCE: 151

Val Ser Leu Thr Asn Val Ser Ile Ser Asp Glu Gly Arg
1               5                   10

<210> SEQ ID NO 152
<211> LENGTH: 10
<212> TYPE: PRT
<213> ORGANISM: Homo sapiens

<400> SEQUENCE: 152

Asn Thr Thr Phe Asn Val Glu Ser Thr Lys
1               5                   10

<210> SEQ ID NO 153
<211> LENGTH: 12
<212> TYPE: PRT
<213> ORGANISM: Homo sapiens

<400> SEQUENCE: 153

Asp Ser Cys Glu Ser Asn His Asn Ile Thr Cys Lys
1               5                   10

<210> SEQ ID NO 154
<211> LENGTH: 14
<212> TYPE: PRT
<213> ORGANISM: Homo sapiens

<400> SEQUENCE: 154

Ser Glu Asn Ala Ser Leu Val Leu Ser Ser Ser Asn Gln Lys
1               5                   10

<210> SEQ ID NO 155
<211> LENGTH: 38
<212> TYPE: PRT
<213> ORGANISM: Homo sapiens

<400> SEQUENCE: 155

Thr Glu Leu Asp Leu Arg Pro Gln Gly Leu Glu Leu Phe Glu Asn Thr
1               5                   10                  15

Ser Ala Pro Tyr Gln Leu Gln Thr Phe Val Leu Pro Ala Thr Pro Pro
            20                  25                  30

Gln Leu Val Ser Pro Arg
        35

<210> SEQ ID NO 156
<211> LENGTH: 15
<212> TYPE: PRT
<213> ORGANISM: Homo sapiens

<400> SEQUENCE: 156

Leu Asn Pro Thr Val Thr Tyr Gly Asn Asp Ser Phe Ser Ala Lys
```

```
1               5                   10                  15
```

<210> SEQ ID NO 157
<211> LENGTH: 14
<212> TYPE: PRT
<213> ORGANISM: Homo sapiens

<400> SEQUENCE: 157

```
Ser Val Gln Leu His Asp Ser Gly Asn Tyr Ser Cys Tyr Arg
1               5                   10
```

<210> SEQ ID NO 158
<211> LENGTH: 28
<212> TYPE: PRT
<213> ORGANISM: Homo sapiens

<400> SEQUENCE: 158

```
Asp Ser Cys Gln Gln Gly Ser Asn Met Thr Leu Ile Gly Glu Asn Gly
1               5                   10                  15

His Ser Thr Asp Thr Leu Thr Gly Ser Gly Phe Arg
            20                  25
```

<210> SEQ ID NO 159
<211> LENGTH: 20
<212> TYPE: PRT
<213> ORGANISM: Homo sapiens

<400> SEQUENCE: 159

```
Arg Leu Asn Ser Thr His Cys Gln Asp Ile Asn Glu Cys Ala Met Pro
1               5                   10                  15

Gly Val Cys Arg
            20
```

<210> SEQ ID NO 160
<211> LENGTH: 30
<212> TYPE: PRT
<213> ORGANISM: Homo sapiens

<400> SEQUENCE: 160

```
Asp Arg Ser His Cys Glu Asp Ile Asp Glu Cys Asp Phe Pro Ala Ala
1               5                   10                  15

Cys Ile Gly Gly Asp Cys Ile Asn Thr Asn Gly Ser Tyr Arg
            20                  25                  30
```

<210> SEQ ID NO 161
<211> LENGTH: 12
<212> TYPE: PRT
<213> ORGANISM: Homo sapiens

<400> SEQUENCE: 161

```
Asn Thr Ser Val Gly Leu Leu Tyr Ser Gly Cys Arg
1               5                   10
```

<210> SEQ ID NO 162
<211> LENGTH: 18
<212> TYPE: PRT
<213> ORGANISM: Homo sapiens

<400> SEQUENCE: 162

```
Lys Phe Asn Ile Thr Glu Ser Val Leu Gln Gly Leu Leu Lys Pro Leu
1               5                   10                  15

Phe Lys
```

<210> SEQ ID NO 163
<211> LENGTH: 16
<212> TYPE: PRT
<213> ORGANISM: Homo sapiens

<400> SEQUENCE: 163

Asn Ile Glu Asp Ala Leu Asn Gln Leu Phe Arg Asn Ser Ser Ile Lys
1               5                   10                  15

<210> SEQ ID NO 164
<211> LENGTH: 12
<212> TYPE: PRT
<213> ORGANISM: Homo sapiens

<400> SEQUENCE: 164

Asn Gly Thr Gln Leu Gln Asn Phe Thr Leu Asp Arg
1               5                   10

<210> SEQ ID NO 165
<211> LENGTH: 31
<212> TYPE: PRT
<213> ORGANISM: Homo sapiens

<400> SEQUENCE: 165

Lys Leu Trp Ala Asp Thr Thr Cys Gly Gln Asn Ala Thr Glu Leu Tyr
1               5                   10                  15

Cys Phe Tyr Ser Glu Asn Thr Asp Leu Thr Cys Arg Gln Pro Lys
            20                  25                  30

<210> SEQ ID NO 166
<211> LENGTH: 19
<212> TYPE: PRT
<213> ORGANISM: Homo sapiens

<400> SEQUENCE: 166

Tyr Phe Ala Thr Asn Cys Ser Ala Thr Phe Gly Leu Glu Asp Asp Val
1               5                   10                  15

Val Lys Lys

<210> SEQ ID NO 167
<211> LENGTH: 10
<212> TYPE: PRT
<213> ORGANISM: Homo sapiens

<400> SEQUENCE: 167

Phe Asn His Thr Gln Thr Ile Gln Gln Lys
1               5                   10

<210> SEQ ID NO 168
<211> LENGTH: 24
<212> TYPE: PRT
<213> ORGANISM: Homo sapiens

<400> SEQUENCE: 168

Val Ile Ser Val Asp Glu Leu Asn Asp Thr Ile Ala Ala Asn Leu Ser
1               5                   10                  15

Asp Thr Glu Phe Tyr Gly Ala Lys
            20

<210> SEQ ID NO 169
<211> LENGTH: 20
<212> TYPE: PRT
<213> ORGANISM: Homo sapiens

<400> SEQUENCE: 169

Glu Arg Pro Pro Thr Phe Leu Thr Pro Glu Gly Asn Ala Ser Asn Lys
1               5                   10                  15

Glu Glu Leu Arg
            20

<210> SEQ ID NO 170
<211> LENGTH: 9
<212> TYPE: PRT
<213> ORGANISM: Homo sapiens

<400> SEQUENCE: 170

Glu Asp Gly Met Leu Pro Lys Asn Arg
1               5

<210> SEQ ID NO 171
<211> LENGTH: 35
<212> TYPE: PRT
<213> ORGANISM: Homo sapiens

<400> SEQUENCE: 171

Gly Ser Ala Leu His Glu Asp Ile Tyr Val Leu His Glu Asn Gly Thr
1               5                   10                  15

Leu Glu Ile Pro Val Ala Gln Lys Asp Ser Thr Gly Thr Tyr Thr Cys
            20                  25                  30

Val Ala Arg
        35

<210> SEQ ID NO 172
<211> LENGTH: 19
<212> TYPE: PRT
<213> ORGANISM: Homo sapiens

<400> SEQUENCE: 172

Val Asn Val Val Asn Ser Thr Leu Ala Glu Val His Trp Asp Pro Val
1               5                   10                  15

Pro Leu Lys

<210> SEQ ID NO 173
<211> LENGTH: 18
<212> TYPE: PRT
<213> ORGANISM: Homo sapiens

<400> SEQUENCE: 173

Gln Leu Leu Glu Lys Val Gln Asn Met Ser Gln Ser Ile Glu Val Leu
1               5                   10                  15

Asp Arg

<210> SEQ ID NO 174
<211> LENGTH: 14
<212> TYPE: PRT
<213> ORGANISM: Homo sapiens

<400> SEQUENCE: 174

Val Gln Asn Met Ser Gln Ser Ile Glu Val Leu Asp Arg Arg
1               5                   10

<210> SEQ ID NO 175
<211> LENGTH: 15
<212> TYPE: PRT
<213> ORGANISM: Homo sapiens

<400> SEQUENCE: 175

Ser Met Val Asp Phe Met Asn Thr Asp Asn Phe Thr Ser His Arg
1               5                   10                  15

<210> SEQ ID NO 176
<211> LENGTH: 19
<212> TYPE: PRT
<213> ORGANISM: Homo sapiens

<400> SEQUENCE: 176

Leu Asp Pro Val Ser Leu Gln Thr Leu Gln Thr Trp Asn Thr Ser Tyr
1               5                   10                  15

Pro Lys Arg

<210> SEQ ID NO 177
<211> LENGTH: 18
<212> TYPE: PRT
<213> ORGANISM: Homo sapiens

<400> SEQUENCE: 177

Gln Leu Leu Glu Lys Val Gln Asn Met Ser Gln Ser Ile Glu Val Leu
1               5                   10                  15

Asp Arg

<210> SEQ ID NO 178
<211> LENGTH: 11
<212> TYPE: PRT
<213> ORGANISM: Homo sapiens

<400> SEQUENCE: 178

Glu Leu Gln Tyr Val Lys Gln Glu Cys Asn Arg
1               5                   10

<210> SEQ ID NO 179
<211> LENGTH: 17
<212> TYPE: PRT
<213> ORGANISM: Homo sapiens

<400> SEQUENCE: 179

Cys Pro Asp Gly Phe Phe Ser Asn Glu Thr Ser Ser Lys Ala Pro Cys
1               5                   10                  15

Arg

<210> SEQ ID NO 180
<211> LENGTH: 18
<212> TYPE: PRT
<213> ORGANISM: Homo sapiens

<400> SEQUENCE: 180

Gly Asn Ala Thr His Asp Asn Ile Cys Ser Gly Asn Ser Glu Ser Thr
1               5                   10                  15

Gln Lys

<210> SEQ ID NO 181
<211> LENGTH: 13
<212> TYPE: PRT
<213> ORGANISM: Homo sapiens

<400> SEQUENCE: 181

His Ile Gly His Ala Asn Leu Thr Phe Glu Gln Leu Arg
1               5                   10

<210> SEQ ID NO 182
<211> LENGTH: 8
<212> TYPE: PRT
<213> ORGANISM: Homo sapiens

<400> SEQUENCE: 182

Gly Ile Asn Glu Ser Tyr Lys Lys
1               5

<210> SEQ ID NO 183
<211> LENGTH: 19
<212> TYPE: PRT
<213> ORGANISM: Homo sapiens

<400> SEQUENCE: 183

Phe Leu Asn Asp Ser Ile Val Asp Pro Val Asp Ser Glu Trp Phe Gly
1               5                   10                  15

Phe Tyr Arg

<210> SEQ ID NO 184
<211> LENGTH: 27
<212> TYPE: PRT
<213> ORGANISM: Homo sapiens

<400> SEQUENCE: 184

His Tyr Gly Pro Gly Trp Val Ser Met Ala Asn Ala Gly Lys Asp Thr
1               5                   10                  15

Asn Gly Ser Gln Phe Phe Ile Thr Thr Val Lys
            20                  25

<210> SEQ ID NO 185
<211> LENGTH: 28
<212> TYPE: PRT
<213> ORGANISM: Homo sapiens

<400> SEQUENCE: 185

Gly Thr Trp Ser Thr Ala Glu Ser Gly Ala Glu Cys Thr Asn Trp Asn
1               5                   10                  15

Ser Ser Ala Leu Ala Gln Lys Pro Tyr Ser Gly Arg
            20                  25

<210> SEQ ID NO 186
<211> LENGTH: 30
<212> TYPE: PRT
<213> ORGANISM: Homo sapiens

<400> SEQUENCE: 186

Ala Gly Lys Tyr Ser Ser Glu Phe Cys Ser Thr Pro Ala Cys Ser Glu
1               5                   10                  15

Gly Asn Ser Asp Cys Tyr Phe Gly Asn Gly Ser Ala Tyr Arg
            20                  25                  30

<210> SEQ ID NO 187
<211> LENGTH: 27
<212> TYPE: PRT
<213> ORGANISM: Homo sapiens

<400> SEQUENCE: 187

Tyr Ser Ser Glu Phe Cys Ser Thr Pro Ala Cys Ser Glu Gly Asn Ser
1               5                   10                  15

Asp Cys Tyr Phe Gly Asn Gly Ser Ala Tyr Arg

-continued

```
<210> SEQ ID NO 188
<211> LENGTH: 22
<212> TYPE: PRT
<213> ORGANISM: Homo sapiens

<400> SEQUENCE: 188

Cys Thr Ser Gln His Leu Leu Asn Arg Thr Val Thr Asp Asn Met Leu
1               5                   10                  15

Cys Ala Gly Asp Thr Arg
            20

<210> SEQ ID NO 189
<211> LENGTH: 19
<212> TYPE: PRT
<213> ORGANISM: Homo sapiens

<400> SEQUENCE: 189

Gln His Thr Val Thr Thr Thr Thr Lys Gly Glu Asn Phe Thr Glu
1               5                   10                  15

Asp Val Lys

<210> SEQ ID NO 190
<211> LENGTH: 10
<212> TYPE: PRT
<213> ORGANISM: Homo sapiens

<400> SEQUENCE: 190

Gly Glu Asn Phe Thr Glu Thr Asp Val Lys
1               5                   10

<210> SEQ ID NO 191
<211> LENGTH: 14
<212> TYPE: PRT
<213> ORGANISM: Homo sapiens

<400> SEQUENCE: 191

Trp Phe Ser Ala Gly Leu Ala Ser Asn Ser Ser Trp Leu Arg
1               5                   10

<210> SEQ ID NO 192
<211> LENGTH: 19
<212> TYPE: PRT
<213> ORGANISM: Homo sapiens

<400> SEQUENCE: 192

Ser Val Val Ala Pro Ala Thr Asp Gly Gly Leu Asn Leu Thr Ser Thr
1               5                   10                  15

Phe Leu Arg

<210> SEQ ID NO 193
<211> LENGTH: 17
<212> TYPE: PRT
<213> ORGANISM: Homo sapiens

<400> SEQUENCE: 193

Lys Val Glu Val Glu Pro Leu Asn Ser Thr Ala Val His Val Tyr Trp
1               5                   10                  15

Lys

<210> SEQ ID NO 194
```

```
<211> LENGTH: 31
<212> TYPE: PRT
<213> ORGANISM: Homo sapiens

<400> SEQUENCE: 194

Asp Ile Asn Ser Gln Gln Glu Leu Gln Asn Ile Thr Thr Asp Thr Arg
1               5                   10                  15

Phe Thr Leu Thr Gly Leu Lys Pro Asp Thr Thr Tyr Asp Ile Lys
            20                  25                  30

<210> SEQ ID NO 195
<211> LENGTH: 17
<212> TYPE: PRT
<213> ORGANISM: Homo sapiens

<400> SEQUENCE: 195

Lys Val Glu Val Glu Pro Leu Asn Ser Thr Ala Val His Val Tyr Trp
1               5                   10                  15

Lys

<210> SEQ ID NO 196
<211> LENGTH: 31
<212> TYPE: PRT
<213> ORGANISM: Homo sapiens

<400> SEQUENCE: 196

Asp Ile Asn Ser Gln Gln Glu Leu Gln Asn Ile Thr Thr Asp Thr Arg
1               5                   10                  15

Phe Thr Leu Thr Gly Leu Lys Pro Asp Thr Thr Tyr Asp Ile Lys
            20                  25                  30

<210> SEQ ID NO 197
<211> LENGTH: 15
<212> TYPE: PRT
<213> ORGANISM: Homo sapiens

<400> SEQUENCE: 197

Gln Leu Thr Leu Gln Trp Glu Pro Leu Gly Tyr Asn Val Thr Arg
1               5                   10                  15

<210> SEQ ID NO 198
<211> LENGTH: 15
<212> TYPE: PRT
<213> ORGANISM: Homo sapiens

<400> SEQUENCE: 198

Leu Leu Ala Asn Ser Ser Met Leu Gly Glu Gly Gln Val Leu Arg
1               5                   10                  15

<210> SEQ ID NO 199
<211> LENGTH: 17
<212> TYPE: PRT
<213> ORGANISM: Homo sapiens

<400> SEQUENCE: 199

Ile Val Ser Pro Glu Pro Gly Gly Ala Val Gly Pro Asn Leu Thr Cys
1               5                   10                  15

Arg

<210> SEQ ID NO 200
<211> LENGTH: 15
<212> TYPE: PRT
```

```
<400> SEQUENCE: 200

Leu Leu Ala Asn Ser Ser Met Leu Gly Glu Gly Gln Val Leu Arg
1               5                   10                  15

<210> SEQ ID NO 201
<211> LENGTH: 17
<212> TYPE: PRT
<213> ORGANISM: Homo sapiens

<400> SEQUENCE: 201

Ile Val Ser Pro Glu Pro Gly Gly Ala Val Gly Pro Asn Leu Thr Cys
1               5                   10                  15

Arg

<210> SEQ ID NO 202
<211> LENGTH: 13
<212> TYPE: PRT
<213> ORGANISM: Homo sapiens

<400> SEQUENCE: 202

Ser Val Asn Leu Ser Asp Gly Glu Leu Leu Ser Ile Arg
1               5                   10

<210> SEQ ID NO 203
<211> LENGTH: 34
<212> TYPE: PRT
<213> ORGANISM: Homo sapiens

<400> SEQUENCE: 203

His Leu Thr Cys Leu Asn Ala Thr Gln Pro Phe Trp Asp Ser Lys Glu
1               5                   10                  15

Pro Val Cys Ile Ala Ala Cys Gly Gly Val Ile Arg Asn Ala Thr Thr
            20                  25                  30

Gly Arg

<210> SEQ ID NO 204
<211> LENGTH: 27
<212> TYPE: PRT
<213> ORGANISM: Homo sapiens

<400> SEQUENCE: 204

Ile Val Ser Pro Gly Phe Pro Gly Asn Tyr Ser Asn Asn Leu Thr Cys
1               5                   10                  15

His Trp Leu Leu Glu Ala Pro Gly Gly Gln Arg
            20                  25

<210> SEQ ID NO 205
<211> LENGTH: 18
<212> TYPE: PRT
<213> ORGANISM: Homo sapiens

<400> SEQUENCE: 205

Gln Ala Ile His Val Gly Asn Gln Thr Phe Asn Asp Gly Thr Ile Val
1               5                   10                  15

Glu Lys

<210> SEQ ID NO 206
<211> LENGTH: 23
<212> TYPE: PRT
<213> ORGANISM: Homo sapiens
```

<400> SEQUENCE: 206

Leu His His His Leu Asp His Asn Asn Thr His His Phe His Asn Asp
1               5                   10                  15

Ser Ile Thr Pro Ser Glu Arg
            20

<210> SEQ ID NO 207
<211> LENGTH: 24
<212> TYPE: PRT
<213> ORGANISM: Homo sapiens

<400> SEQUENCE: 207

Gly Glu Pro Ser Asn Glu Pro Ser Thr Glu Thr Asn Lys Thr Gln Glu
1               5                   10                  15

Gln Ser Asp Val Lys Leu Pro Lys
            20

<210> SEQ ID NO 208
<211> LENGTH: 20
<212> TYPE: PRT
<213> ORGANISM: Homo sapiens

<400> SEQUENCE: 208

Lys Asp Leu Asn Glu Asp Asp His His His Glu Cys Leu Asn Val Thr
1               5                   10                  15

Gln Leu Leu Lys
            20

<210> SEQ ID NO 209
<211> LENGTH: 24
<212> TYPE: PRT
<213> ORGANISM: Homo sapiens

<400> SEQUENCE: 209

Gln Ser Gly Val Asn Ala Thr Leu Pro Glu Glu Asn Gln Pro Val Val
1               5                   10                  15

Phe Asn His Val Tyr Asn Ile Lys
            20

<210> SEQ ID NO 210
<211> LENGTH: 31
<212> TYPE: PRT
<213> ORGANISM: Homo sapiens

<400> SEQUENCE: 210

Cys Ile Asn Gly Thr Cys Tyr Cys Glu Glu Gly Phe Thr Gly Glu Asp
1               5                   10                  15

Cys Gly Lys Pro Thr Cys Pro His Ala Cys His Thr Gln Gly Arg
            20                  25                  30

<210> SEQ ID NO 211
<211> LENGTH: 27
<212> TYPE: PRT
<213> ORGANISM: Homo sapiens

<400> SEQUENCE: 211

Gln Thr Gly Leu Ala Pro Gly Gln Glu Tyr Glu Ile Ser Leu His Ile
1               5                   10                  15

Val Lys Asn Asn Thr Arg Gly Pro Gly Leu Lys
            20                  25

-continued

```
<210> SEQ ID NO 212
<211> LENGTH: 17
<212> TYPE: PRT
<213> ORGANISM: Homo sapiens

<400> SEQUENCE: 212

Leu Asn Tyr Ser Leu Pro Thr Gly Gln Trp Val Gly Val Gln Leu Pro
1               5                   10                  15

Arg

<210> SEQ ID NO 213
<211> LENGTH: 24
<212> TYPE: PRT
<213> ORGANISM: Homo sapiens

<400> SEQUENCE: 213

Asn Thr Thr Ser Tyr Val Leu Arg Gly Leu Glu Pro Gly Gln Glu Tyr
1               5                   10                  15

Asn Val Leu Leu Thr Ala Glu Lys
            20

<210> SEQ ID NO 214
<211> LENGTH: 25
<212> TYPE: PRT
<213> ORGANISM: Homo sapiens

<400> SEQUENCE: 214

Val Lys Ala Ser Thr Glu Gln Ala Pro Glu Leu Glu Asn Leu Thr Val
1               5                   10                  15

Thr Glu Val Gly Trp Asp Gly Leu Arg
            20                  25

<210> SEQ ID NO 215
<211> LENGTH: 27
<212> TYPE: PRT
<213> ORGANISM: Homo sapiens

<400> SEQUENCE: 215

Leu Asn Trp Thr Ala Ala Asp Gln Ala Tyr Glu His Phe Ile Ile Gln
1               5                   10                  15

Val Gln Glu Ala Asn Lys Val Glu Ala Ala Arg
            20                  25

<210> SEQ ID NO 216
<211> LENGTH: 14
<212> TYPE: PRT
<213> ORGANISM: Homo sapiens

<400> SEQUENCE: 216

Leu Leu Glu Thr Val Glu Tyr Asn Ile Ser Gly Ala Glu Arg
1               5                   10

<210> SEQ ID NO 217
<211> LENGTH: 8
<212> TYPE: PRT
<213> ORGANISM: Homo sapiens

<400> SEQUENCE: 217

Tyr Phe Tyr Asn Asn Gln Thr Lys
1               5

<210> SEQ ID NO 218
<211> LENGTH: 29
```

<212> TYPE: PRT
<213> ORGANISM: Homo sapiens

<400> SEQUENCE: 218

Leu Arg Leu Ala Ser Pro Pro Ser Gln Gly Glu Val Pro Pro Gly Pro
1               5                   10                  15

Leu Pro Glu Ala Val Leu Ala Leu Tyr Asn Ser Thr Arg
            20                  25

<210> SEQ ID NO 219
<211> LENGTH: 17
<212> TYPE: PRT
<213> ORGANISM: Homo sapiens

<400> SEQUENCE: 219

Gln Cys Asn Gly Thr Ser Thr Cys Trp Cys Val Asn Thr Ala Gly Val
1               5                   10                  15

Arg

<210> SEQ ID NO 220
<211> LENGTH: 18
<212> TYPE: PRT
<213> ORGANISM: Homo sapiens

<400> SEQUENCE: 220

His Arg Pro Thr Ala Gly Ala Phe Asn His Ser Asp Leu Asp Ala Glu
1               5                   10                  15

Leu Arg

<210> SEQ ID NO 221
<211> LENGTH: 15
<212> TYPE: PRT
<213> ORGANISM: Homo sapiens

<400> SEQUENCE: 221

Leu Ser Asn Ile Ser His Leu Asn Tyr Cys Glu Pro Asp Leu Arg
1               5                   10                  15

<210> SEQ ID NO 222
<211> LENGTH: 16
<212> TYPE: PRT
<213> ORGANISM: Homo sapiens

<400> SEQUENCE: 222

Glu Ser Trp Gly Gln Glu Ser Asn Ala Gly Asn Gln Thr Val Val Arg
1               5                   10                  15

<210> SEQ ID NO 223
<211> LENGTH: 15
<212> TYPE: PRT
<213> ORGANISM: Homo sapiens

<400> SEQUENCE: 223

Asn Ala Ser Val Pro Gln Ile Leu Ile Ile Val Thr Asp Gly Lys
1               5                   10                  15

<210> SEQ ID NO 224
<211> LENGTH: 468
<212> TYPE: PRT
<213> ORGANISM: Homo sapiens
<220> FEATURE:
<223> OTHER INFORMATION: secretogranin III

<400> SEQUENCE: 224

```
Met Gly Phe Leu Gly Thr Gly Thr Trp Ile Leu Val Leu Val Leu Pro
1               5                   10                  15

Ile Gln Ala Phe Pro Lys Pro Gly Gly Ser Gln Asp Lys Ser Leu His
                20                  25                  30

Asn Arg Glu Leu Ser Ala Glu Arg Pro Leu Asn Glu Gln Ile Ala Glu
            35                  40                  45

Ala Glu Glu Asp Lys Ile Lys Lys Thr Tyr Pro Pro Glu Asn Lys Pro
50                  55                  60

Gly Gln Ser Asn Tyr Ser Phe Val Asp Asn Leu Asn Leu Leu Lys Ala
65                  70                  75                  80

Ile Thr Glu Lys Glu Lys Ile Glu Lys Glu Arg Gln Ser Ile Arg Ser
                85                  90                  95

Ser Pro Leu Asp Asn Lys Leu Asn Val Glu Asp Val Asp Ser Thr Lys
            100                 105                 110

Asn Arg Lys Leu Ile Asp Asp Tyr Asp Ser Thr Lys Ser Gly Leu Asp
            115                 120                 125

His Lys Phe Gln Asp Asp Pro Asp Gly Leu His Gln Leu Asp Gly Thr
130                 135                 140

Pro Leu Thr Ala Glu Asp Ile Val His Lys Ile Ala Ala Arg Ile Tyr
145                 150                 155                 160

Glu Glu Asn Asp Arg Ala Val Phe Asp Lys Ile Val Ser Lys Leu Leu
            165                 170                 175

Asn Leu Gly Leu Ile Thr Glu Ser Gln Ala His Thr Leu Glu Asp Glu
            180                 185                 190

Val Ala Glu Val Leu Gln Lys Leu Ile Ser Lys Glu Ala Asn Asn Tyr
            195                 200                 205

Glu Glu Asp Pro Asn Lys Pro Thr Ser Trp Thr Glu Asn Gln Ala Gly
210                 215                 220

Lys Ile Pro Glu Lys Val Thr Pro Met Ala Ala Ile Gln Asp Gly Leu
225                 230                 235                 240

Ala Lys Gly Glu Asn Asp Glu Thr Val Ser Asn Thr Leu Thr Leu Thr
            245                 250                 255

Asn Gly Leu Glu Arg Arg Thr Lys Thr Tyr Ser Glu Asp Asn Phe Glu
            260                 265                 270

Glu Leu Gln Tyr Phe Pro Asn Phe Tyr Ala Leu Leu Lys Ser Ile Asp
            275                 280                 285

Ser Glu Lys Glu Ala Lys Glu Lys Glu Thr Leu Ile Thr Ile Met Lys
            290                 295                 300

Thr Leu Ile Asp Phe Val Lys Met Met Val Lys Tyr Gly Thr Ile Ser
305                 310                 315                 320

Pro Glu Glu Gly Val Ser Tyr Leu Glu Asn Leu Asp Glu Met Ile Ala
            325                 330                 335

Leu Gln Thr Lys Asn Lys Leu Glu Lys Asn Ala Thr Asp Asn Ile Ser
            340                 345                 350

Lys Leu Phe Pro Ala Pro Ser Glu Lys Ser His Glu Glu Thr Asp Ser
            355                 360                 365

Thr Lys Glu Glu Ala Ala Lys Met Glu Lys Tyr Gly Ser Leu Lys
370                 375                 380

Asp Ser Thr Lys Asp Asp Asn Ser Asn Pro Gly Gly Lys Thr Asp Glu
385                 390                 395                 400

Pro Lys Gly Lys Thr Glu Ala Tyr Leu Glu Ala Ile Arg Lys Asn Ile
            405                 410                 415
```

```
Glu Trp Leu Lys Lys His Asp Lys Lys Gly Asn Lys Glu Asp Tyr Asp
                420                 425                 430

Leu Ser Lys Met Arg Asp Phe Ile Asn Lys Gln Ala Asp Ala Tyr Val
            435                 440                 445

Glu Lys Gly Ile Leu Asp Lys Glu Glu Ala Glu Ala Ile Lys Arg Ile
        450                 455                 460

Tyr Ser Ser Leu
465

<210> SEQ ID NO 225
<211> LENGTH: 2477
<212> TYPE: PRT
<213> ORGANISM: Homo sapiens
<220> FEATURE:
<223> OTHER INFORMATION: Fibronectin 1 isoform 1

<400> SEQUENCE: 225

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro
    290                 295                 300
```

```
Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
            325                 330                 335

Gly Asn Gly Val Ser Cys Gln Glu Thr Ala Val Thr Gln Thr Tyr Gly
                340                 345                 350

Gly Asn Ser Asn Gly Glu Pro Cys Val Leu Pro Phe Thr Tyr Asn Gly
            355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
            405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
        500                 505                 510

Gln Leu Arg Asp Gln Cys Ile Val Asp Asp Ile Thr Tyr Asn Val Asn
    515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
            565                 570                 575

Glu Lys Tyr Val His Gly Val Arg Tyr Gln Cys Tyr Cys Tyr Gly Arg
        580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
            645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
```

```
                725                 730                 735
Val Val Ser Trp Val Ser Ala Ser Asp Thr Val Ser Gly Phe Arg Val
            740                 745                 750
Glu Tyr Glu Leu Ser Glu Gly Asp Glu Pro Gln Tyr Leu Asp Leu
            755                 760                 765
Pro Ser Thr Ala Thr Ser Val Asn Ile Pro Asp Leu Leu Pro Gly Arg
            770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
                805                 810                 815
Pro Thr Val Asp Gln Val Asp Asp Thr Ser Ile Val Val Arg Trp Ser
                820                 825                 830
Arg Pro Gln Ala Pro Ile Thr Gly Tyr Arg Ile Val Tyr Ser Pro Ser
                835                 840                 845
Val Glu Gly Ser Ser Thr Glu Leu Asn Leu Pro Glu Thr Ala Asn Ser
            850                 855                 860
Val Thr Leu Ser Asp Leu Gln Pro Gly Val Gln Tyr Asn Ile Thr Ile
865                 870                 875                 880
Tyr Ala Val Glu Glu Asn Gln Glu Ser Thr Pro Val Val Ile Gln Gln
                885                 890                 895
Glu Thr Thr Gly Thr Pro Arg Ser Asp Thr Val Pro Ser Pro Arg Asp
                900                 905                 910
Leu Gln Phe Val Glu Val Thr Asp Val Lys Val Thr Ile Met Trp Thr
                915                 920                 925
Pro Pro Glu Ser Ala Val Thr Gly Tyr Arg Val Asp Val Ile Pro Val
            930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
                965                 970                 975
Val Phe Ala Val Ser His Gly Arg Glu Ser Lys Pro Leu Thr Ala Gln
                980                 985                 990
Gln Thr Thr Lys Leu Asp Ala Pro  Thr Asn Leu Gln Phe Val Asn Glu
            995                 1000                1005
Thr Asp Ser Thr Val Leu Val Arg Trp Thr Pro Arg Ala Gln
            1010                1015                1020
Ile Thr Gly Tyr Arg Leu Thr Val Gly Leu Thr Arg Arg Gly Gln
            1025                1030                1035
Pro Arg Gln Tyr Asn Val Gly Pro Ser Val Ser Lys Tyr Pro Leu
            1040                1045                1050
Arg Asn Leu Gln Pro Ala Ser Glu Tyr Thr Val Ser Leu Val Ala
            1055                1060                1065
Ile Lys Gly Asn Gln Glu Ser Pro Lys Ala Thr Gly Val Phe Thr
            1070                1075                1080
Thr Leu Gln Pro Gly Ser Ser  Ile Pro Pro Tyr Asn Thr Glu Val
            1085                1090                1095
Thr Glu Thr Thr Ile Val Ile Thr Trp Thr Pro Ala Pro Arg Ile
            1100                1105                1110
Gly Phe Lys Leu Gly Val Arg Pro Ser Gln Gly Gly Glu Ala Pro
            1115                1120                1125
Arg Glu Val Thr Ser Asp Ser Gly Ser Ile Val Val Ser Gly Leu
            1130                1135                1140
```

```
Thr Pro Gly Val Glu Tyr Val Tyr Thr Ile Gln Val Leu Arg Asp
1145                1150                1155

Gly Gln Glu Arg Asp Ala Pro Ile Val Asn Lys Val Val Thr Pro
1160                1165                1170

Leu Ser Pro Pro Thr Asn Leu His Leu Glu Ala Asn Pro Asp Thr
1175                1180                1185

Gly Val Leu Thr Val Ser Trp Glu Arg Ser Thr Thr Pro Asp Ile
1190                1195                1200

Thr Gly Tyr Arg Ile Thr Thr Pro Thr Asn Gly Gln Gln Gly
1205                1210                1215

Asn Ser Leu Glu Glu Val Val His Ala Asp Gln Ser Ser Cys Thr
1220                1225                1230

Phe Asp Asn Leu Ser Pro Gly Leu Glu Tyr Asn Val Ser Val Tyr
1235                1240                1245

Thr Val Lys Asp Asp Lys Glu Ser Val Pro Ile Ser Asp Thr Ile
1250                1255                1260

Ile Pro Glu Val Pro Gln Leu Thr Asp Leu Ser Phe Val Asp Ile
1265                1270                1275

Thr Asp Ser Ser Ile Gly Leu Arg Trp Thr Pro Leu Asn Ser Ser
1280                1285                1290

Thr Ile Ile Gly Tyr Arg Ile Thr Val Val Ala Ala Gly Glu Gly
1295                1300                1305

Ile Pro Ile Phe Glu Asp Phe Val Asp Ser Ser Val Gly Tyr Tyr
1310                1315                1320

Thr Val Thr Gly Leu Glu Pro Gly Ile Asp Tyr Asp Ile Ser Val
1325                1330                1335

Ile Thr Leu Ile Asn Gly Gly Glu Ser Ala Pro Thr Thr Leu Thr
1340                1345                1350

Gln Gln Thr Ala Val Pro Pro Pro Thr Asp Leu Arg Phe Thr Asn
1355                1360                1365

Ile Gly Pro Asp Thr Met Arg Val Thr Trp Ala Pro Pro Pro Ser
1370                1375                1380

Ile Asp Leu Thr Asn Phe Leu Val Arg Tyr Ser Pro Val Lys Asn
1385                1390                1395

Glu Glu Asp Val Ala Glu Leu Ser Ile Ser Pro Ser Asp Asn Ala
1400                1405                1410

Val Val Leu Thr Asn Leu Leu Pro Gly Thr Glu Tyr Val Val Ser
1415                1420                1425

Val Ser Ser Val Tyr Glu Gln His Glu Ser Thr Pro Leu Arg Gly
1430                1435                1440

Arg Gln Lys Thr Gly Leu Asp Ser Pro Thr Gly Ile Asp Phe Ser
1445                1450                1455

Asp Ile Thr Ala Asn Ser Phe Thr Val His Trp Ile Ala Pro Arg
1460                1465                1470

Ala Thr Ile Thr Gly Tyr Arg Ile Arg His His Pro Glu His Phe
1475                1480                1485

Ser Gly Arg Pro Arg Glu Asp Arg Val Pro His Ser Arg Asn Ser
1490                1495                1500

Ile Thr Leu Thr Asn Leu Thr Pro Gly Thr Glu Tyr Val Val Ser
1505                1510                1515

Ile Val Ala Leu Asn Gly Arg Glu Glu Ser Pro Leu Leu Ile Gly
1520                1525                1530
```

```
Gln Gln Ser Thr Val Ser Asp Val Pro Arg Asp Leu Glu Val Val
    1535                1540                1545

Ala Ala Thr Pro Thr Ser Leu Leu Ile Ser Trp Asp Ala Pro Ala
1550                1555                1560

Val Thr Val Arg Tyr Tyr Arg Ile Thr Tyr Gly Glu Thr Gly Gly
    1565                1570                1575

Asn Ser Pro Val Gln Glu Phe Thr Val Pro Gly Ser Lys Ser Thr
1580                1585                1590

Ala Thr Ile Ser Gly Leu Lys Pro Gly Val Asp Tyr Thr Ile Thr
    1595                1600                1605

Val Tyr Ala Val Thr Gly Arg Gly Asp Ser Pro Ala Ser Ser Lys
1610                1615                1620

Pro Ile Ser Ile Asn Tyr Arg Thr Glu Ile Asp Lys Pro Ser Gln
    1625                1630                1635

Met Gln Val Thr Asp Val Gln Asp Asn Ser Ile Ser Val Lys Trp
1640                1645                1650

Leu Pro Ser Ser Ser Pro Val Thr Gly Tyr Arg Val Thr Thr Thr
    1655                1660                1665

Pro Lys Asn Gly Pro Gly Pro Thr Lys Thr Lys Thr Ala Gly Pro
1670                1675                1680

Asp Gln Thr Glu Met Thr Ile Glu Gly Leu Gln Pro Thr Val Glu
    1685                1690                1695

Tyr Val Ser Val Tyr Ala Gln Asn Pro Ser Gly Glu Ser Gln
1700                1705                1710

Pro Leu Val Gln Thr Ala Val Thr Asn Ile Asp Arg Pro Lys Gly
    1715                1720                1725

Leu Ala Phe Thr Asp Val Asp Ser Ile Lys Ile Ala Trp
1730                1735                1740

Glu Ser Pro Gln Gly Gln Val Ser Arg Tyr Arg Val Thr Tyr Ser
    1745                1750                1755

Ser Pro Glu Asp Gly Ile His Glu Leu Phe Pro Ala Pro Asp Gly
1760                1765                1770

Glu Glu Asp Thr Ala Glu Leu Gln Gly Leu Arg Pro Gly Ser Glu
    1775                1780                1785

Tyr Thr Val Ser Val Val Ala Leu His Asp Asp Met Glu Ser Gln
1790                1795                1800

Pro Leu Ile Gly Thr Gln Ser Thr Ala Ile Pro Ala Pro Thr Asp
    1805                1810                1815

Leu Lys Phe Thr Gln Val Thr Pro Thr Ser Leu Ser Ala Gln Trp
1820                1825                1830

Thr Pro Pro Asn Val Gln Leu Thr Gly Tyr Arg Val Arg Val Thr
    1835                1840                1845

Pro Lys Glu Lys Thr Gly Pro Met Lys Glu Ile Asn Leu Ala Pro
1850                1855                1860

Asp Ser Ser Ser Val Val Val Ser Gly Leu Met Val Ala Thr Lys
    1865                1870                1875

Tyr Glu Val Ser Val Tyr Ala Leu Lys Asp Thr Leu Thr Ser Arg
1880                1885                1890

Pro Ala Gln Gly Val Val Thr Thr Leu Glu Asn Val Ser Pro Pro
    1895                1900                1905

Arg Arg Ala Arg Val Thr Asp Ala Thr Glu Thr Thr Ile Thr Ile
1910                1915                1920

Ser Trp Arg Thr Lys Thr Glu Thr Ile Thr Gly Phe Gln Val Asp
```

-continued

```
            1925                1930                1935

Ala Val Pro Ala Asn Gly Gln Thr Pro Ile Gln Arg Thr Ile Lys
            1940                1945                1950

Pro Asp Val Arg Ser Tyr Thr Ile Thr Gly Leu Gln Pro Gly Thr
            1955                1960                1965

Asp Tyr Lys Ile Tyr Leu Tyr Thr Leu Asn Asp Asn Ala Arg Ser
            1970                1975                1980

Ser Pro Val Val Ile Asp Ala Ser Thr Ala Ile Asp Ala Pro Ser
            1985                1990                1995

Asn Leu Arg Phe Leu Ala Thr Thr Pro Asn Ser Leu Leu Val Ser
            2000                2005                2010

Trp Gln Pro Pro Arg Ala Arg Ile Thr Gly Tyr Ile Ile Lys Tyr
            2015                2020                2025

Glu Lys Pro Gly Ser Pro Pro Arg Glu Val Val Pro Arg Pro Arg
            2030                2035                2040

Pro Gly Val Thr Glu Ala Thr Ile Thr Gly Leu Glu Pro Gly Thr
            2045                2050                2055

Glu Tyr Thr Ile Tyr Val Ile Ala Leu Lys Asn Asn Gln Lys Ser
            2060                2065                2070

Glu Pro Leu Ile Gly Arg Lys Lys Thr Asp Glu Leu Pro Gln Leu
            2075                2080                2085

Val Thr Leu Pro His Pro Asn Leu His Gly Pro Glu Ile Leu Asp
            2090                2095                2100

Val Pro Ser Thr Val Gln Lys Thr Pro Phe Val Thr His Pro Gly
            2105                2110                2115

Tyr Asp Thr Gly Asn Gly Ile Gln Leu Pro Gly Thr Ser Gly Gln
            2120                2125                2130

Gln Pro Ser Val Gly Gln Gln Met Ile Phe Glu Glu His Gly Phe
            2135                2140                2145

Arg Arg Thr Thr Pro Pro Thr Thr Ala Thr Pro Ile Arg His Arg
            2150                2155                2160

Pro Arg Pro Tyr Pro Pro Asn Val Gly Glu Glu Ile Gln Ile Gly
            2165                2170                2175

His Ile Pro Arg Glu Asp Val Asp Tyr His Leu Tyr Pro His Gly
            2180                2185                2190

Pro Gly Leu Asn Pro Asn Ala Ser Thr Gly Gln Glu Ala Leu Ser
            2195                2200                2205

Gln Thr Thr Ile Ser Trp Ala Pro Phe Gln Asp Thr Ser Glu Tyr
            2210                2215                2220

Ile Ile Ser Cys His Pro Val Gly Thr Asp Glu Glu Pro Leu Gln
            2225                2230                2235

Phe Arg Val Pro Gly Thr Ser Thr Ser Ala Thr Leu Thr Gly Leu
            2240                2245                2250

Thr Arg Gly Ala Thr Tyr Asn Ile Ile Val Glu Ala Leu Lys Asp
            2255                2260                2265

Gln Gln Arg His Lys Val Arg Glu Glu Val Val Thr Val Gly Asn
            2270                2275                2280

Ser Val Asn Glu Gly Leu Asn Gln Pro Thr Asp Asp Ser Cys Phe
            2285                2290                2295

Asp Pro Tyr Thr Val Ser His Tyr Ala Val Gly Asp Glu Trp Glu
            2300                2305                2310

Arg Met Ser Glu Ser Gly Phe Lys Leu Leu Cys Gln Cys Leu Gly
            2315                2320                2325
```

```
Phe Gly Ser Gly His Phe Arg Cys Asp Ser Ser Arg Trp Cys His
    2330            2335                2340

Asp Asn Gly Val Asn Tyr Lys Ile Gly Glu Lys Trp Asp Arg Gln
    2345            2350                2355

Gly Glu Asn Gly Gln Met Met Ser Cys Thr Cys Leu Gly Asn Gly
    2360            2365                2370

Lys Gly Glu Phe Lys Cys Asp Pro His Glu Ala Thr Cys Tyr Asp
    2375            2380                2385

Asp Gly Lys Thr Tyr His Val Gly Glu Gln Trp Gln Lys Glu Tyr
    2390            2395                2400

Leu Gly Ala Ile Cys Ser Cys Thr Cys Phe Gly Gly Gln Arg Gly
    2405            2410                2415

Trp Arg Cys Asp Asn Cys Arg Arg Pro Gly Gly Glu Pro Ser Pro
    2420            2425                2430

Glu Gly Thr Thr Gly Gln Ser Tyr Asn Gln Tyr Ser Gln Arg Tyr
    2435            2440                2445

His Gln Arg Thr Asn Thr Asn Val Asn Cys Pro Ile Glu Cys Phe
    2450            2455                2460

Met Pro Leu Asp Val Gln Ala Asp Arg Glu Asp Ser Arg Glu
    2465            2470                2475

<210> SEQ ID NO 226
<211> LENGTH: 2421
<212> TYPE: PRT
<213> ORGANISM: Homo sapiens
<220> FEATURE:
<223> OTHER INFORMATION: Fibronectin 1 isoform 2

<400> SEQUENCE: 226

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
        50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205
```

```
Met Met Val Asp Cys Thr Cys Leu Gly Glu Gly Ser Gly Arg Ile Thr
    210                 215                 220
Cys Thr Ser Arg Asn Arg Cys Asn Asp Gln Asp Thr Arg Thr Ser Tyr
225                 230                 235                 240
Arg Ile Gly Asp Thr Trp Ser Lys Lys Asp Asn Arg Gly Asn Leu Leu
                245                 250                 255
Gln Cys Ile Cys Thr Gly Asn Gly Arg Gly Glu Trp Lys Cys Glu Arg
            260                 265                 270
His Thr Ser Val Gln Thr Thr Ser Gly Ser Gly Pro Phe Thr Asp
        275                 280                 285
Val Arg Ala Ala Val Tyr Gln Pro Gln Pro His Pro Gln Pro Pro
290                 295                 300
Tyr Gly His Cys Val Thr Asp Ser Gly Val Val Tyr Ser Val Gly Met
305                 310                 315                 320
Gln Trp Leu Lys Thr Gln Gly Asn Lys Gln Met Leu Cys Thr Cys Leu
                325                 330                 335
Gly Asn Gly Val Ser Cys Gln Glu Thr Ala Val Thr Gln Thr Tyr Gly
            340                 345                 350
Gly Asn Ser Asn Gly Glu Pro Cys Val Leu Pro Phe Thr Tyr Asn Gly
        355                 360                 365
Arg Thr Phe Tyr Ser Cys Thr Thr Glu Gly Arg Gln Asp Gly His Leu
370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Arg Gly Gly Asn Ser Asn
                405                 410                 415
Gly Ala Leu Cys His Phe Pro Phe Leu Tyr Asn Asn His Asn Tyr Thr
            420                 425                 430
Asp Cys Thr Ser Glu Gly Arg Arg Asp Asn Met Lys Trp Cys Gly Thr
        435                 440                 445
Thr Gln Asn Tyr Asp Ala Asp Gln Lys Phe Gly Phe Cys Pro Met Ala
450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                485                 490                 495
Thr Cys Val Gly Asn Gly Arg Gly Glu Trp Thr Cys Ile Ala Tyr Ser
            500                 505                 510
Gln Leu Arg Asp Gln Cys Ile Val Asp Asp Ile Thr Tyr Asn Val Asn
        515                 520                 525
Asp Thr Phe His Lys Arg His Glu Glu Gly His Met Leu Asn Cys Thr
530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
        595                 600                 605
Ser Gly Pro Val Glu Val Phe Ile Thr Glu Thr Pro Ser Gln Pro Asn
610                 615                 620
```

```
Ser His Pro Ile Gln Trp Asn Ala Pro Gln Ser His Ile Ser Lys
625                 630                 635                 640

Tyr Ile Leu Arg Trp Arg Pro Lys Asn Ser Val Gly Arg Trp Lys Glu
            645                 650                 655

Ala Thr Ile Pro Gly His Leu Asn Ser Tyr Thr Ile Lys Gly Leu Lys
        660                 665                 670

Pro Gly Val Val Tyr Glu Gly Gln Leu Ile Ser Ile Gln Gln Tyr Gly
    675                 680                 685

His Gln Glu Val Thr Arg Phe Asp Phe Thr Thr Ser Thr Ser Thr
690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
            725                 730                 735

Val Val Ser Trp Val Ser Ala Ser Asp Thr Val Ser Gly Phe Arg Val
            740                 745                 750

Glu Tyr Glu Leu Ser Glu Gly Asp Glu Pro Gln Tyr Leu Asp Leu
            755                 760                 765

Pro Ser Thr Ala Thr Ser Val Asn Ile Pro Asp Leu Leu Pro Gly Arg
770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
            805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
            835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
            885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
            915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
            965                 970                 975

Val Phe Ala Val Ser His Gly Arg Glu Ser Lys Pro Leu Thr Ala Gln
            980                 985                 990

Gln Thr Thr Lys Leu Asp Ala Pro  Thr Asn Leu Gln Phe Val Asn Glu
    995                 1000                1005

Thr Asp Ser Thr Val Leu Val Arg Trp Thr Pro Arg Ala Gln
    1010                1015                1020

Ile Thr Gly Tyr Arg Leu Thr  Val Gly Leu Thr Arg Arg Gly Gln
    1025                1030                1035

Pro Arg Gln Tyr Asn Val Gly  Pro Ser Val Ser Lys  Tyr Pro Leu
```

```
            1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Glu Ala Pro
    1115                1120                1125

Arg Glu Val Thr Ser Asp Ser Gly Ser Ile Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260

Ile Pro Glu Val Pro Gln Leu Thr Asp Leu Ser Phe Val Asp Ile
    1265                1270                1275

Thr Asp Ser Ser Ile Gly Leu Arg Trp Thr Pro Leu Asn Ser Ser
    1280                1285                1290

Thr Ile Ile Gly Tyr Arg Ile Thr Val Val Ala Ala Gly Glu Gly
    1295                1300                1305

Ile Pro Ile Phe Glu Asp Phe Val Asp Ser Ser Val Gly Tyr Tyr
    1310                1315                1320

Thr Val Thr Gly Leu Glu Pro Gly Ile Asp Tyr Asp Ile Ser Val
    1325                1330                1335

Ile Thr Leu Ile Asn Gly Gly Glu Ser Ala Pro Thr Thr Leu Thr
    1340                1345                1350

Gln Gln Thr Ala Val Pro Pro Pro Thr Asp Leu Arg Phe Thr Asn
    1355                1360                1365

Ile Gly Pro Asp Thr Met Arg Val Thr Trp Ala Pro Pro Pro Ser
    1370                1375                1380

Ile Asp Leu Thr Asn Phe Leu Val Arg Tyr Ser Pro Val Lys Asn
    1385                1390                1395

Glu Glu Asp Val Ala Glu Leu Ser Ile Ser Pro Ser Asp Asn Ala
    1400                1405                1410

Val Val Leu Thr Asn Leu Leu Pro Gly Thr Glu Tyr Val Val Ser
    1415                1420                1425

Val Ser Ser Val Tyr Glu Gln His Glu Ser Thr Pro Leu Arg Gly
    1430                1435                1440
```

```
Arg Gln Lys Thr Gly Leu Asp Ser Pro Thr Gly Ile Asp Phe Ser
1445                1450                1455

Asp Ile Thr Ala Asn Ser Phe Thr Val His Trp Ile Ala Pro Arg
1460                1465                1470

Ala Thr Ile Thr Gly Tyr Arg Ile Arg His His Pro Glu His Phe
1475                1480                1485

Ser Gly Arg Pro Arg Glu Asp Arg Val Pro His Ser Arg Asn Ser
1490                1495                1500

Ile Thr Leu Thr Asn Leu Thr Pro Gly Thr Glu Tyr Val Val Ser
1505                1510                1515

Ile Val Ala Leu Asn Gly Arg Glu Glu Ser Pro Leu Leu Ile Gly
1520                1525                1530

Gln Gln Ser Thr Val Ser Asp Val Pro Arg Asp Leu Glu Val Val
1535                1540                1545

Ala Ala Thr Pro Thr Ser Leu Leu Ile Ser Trp Asp Ala Pro Ala
1550                1555                1560

Val Thr Val Arg Tyr Tyr Arg Ile Thr Tyr Gly Glu Thr Gly Gly
1565                1570                1575

Asn Ser Pro Val Gln Glu Phe Thr Val Pro Gly Ser Lys Ser Thr
1580                1585                1590

Ala Thr Ile Ser Gly Leu Lys Pro Gly Val Asp Tyr Thr Ile Thr
1595                1600                1605

Val Tyr Ala Val Thr Gly Arg Gly Asp Ser Pro Ala Ser Ser Lys
1610                1615                1620

Pro Ile Ser Ile Asn Tyr Arg Thr Glu Ile Asp Lys Pro Ser Gln
1625                1630                1635

Met Gln Val Thr Asp Val Gln Asp Asn Ser Ile Ser Val Lys Trp
1640                1645                1650

Leu Pro Ser Ser Ser Pro Val Thr Gly Tyr Arg Val Thr Thr Thr
1655                1660                1665

Pro Lys Asn Gly Pro Gly Pro Thr Lys Thr Lys Thr Ala Gly Pro
1670                1675                1680

Asp Gln Thr Glu Met Thr Ile Glu Gly Leu Gln Pro Thr Val Glu
1685                1690                1695

Tyr Val Val Ser Val Tyr Ala Gln Asn Pro Ser Gly Glu Ser Gln
1700                1705                1710

Pro Leu Val Gln Thr Ala Val Thr Asn Ile Asp Arg Pro Lys Gly
1715                1720                1725

Leu Ala Phe Thr Asp Val Asp Val Asp Ser Ile Lys Ile Ala Trp
1730                1735                1740

Glu Ser Pro Gln Gly Gln Val Ser Arg Tyr Arg Val Thr Tyr Ser
1745                1750                1755

Ser Pro Glu Asp Gly Ile His Glu Leu Phe Pro Ala Pro Asp Gly
1760                1765                1770

Glu Glu Asp Thr Ala Glu Leu Gln Gly Leu Arg Pro Gly Ser Glu
1775                1780                1785

Tyr Thr Val Ser Val Val Ala Leu His Asp Asp Met Glu Ser Gln
1790                1795                1800

Pro Leu Ile Gly Thr Gln Ser Thr Ala Ile Pro Ala Pro Thr Asp
1805                1810                1815

Leu Lys Phe Thr Gln Val Thr Pro Thr Ser Leu Ser Ala Gln Trp
1820                1825                1830
```

-continued

```
Thr Pro Pro Asn Val Gln Leu Thr Gly Tyr Arg Val Arg Val Thr
    1835                1840                1845

Pro Lys Glu Lys Thr Gly Pro Met Lys Glu Ile Asn Leu Ala Pro
    1850                1855                1860

Asp Ser Ser Ser Val Val Ser Gly Leu Met Val Ala Thr Lys
    1865                1870                1875

Tyr Glu Val Ser Val Tyr Ala Leu Lys Asp Thr Leu Thr Ser Arg
    1880                1885                1890

Pro Ala Gln Gly Val Val Thr Leu Glu Asn Val Ser Pro Pro
    1895                1900                1905

Arg Arg Ala Arg Val Thr Asp Ala Thr Glu Thr Ile Thr Ile
    1910                1915                1920

Ser Trp Arg Thr Lys Thr Glu Thr Ile Thr Gly Phe Gln Val Asp
    1925                1930                1935

Ala Val Pro Ala Asn Gly Gln Thr Pro Ile Gln Arg Thr Ile Lys
    1940                1945                1950

Pro Asp Val Arg Ser Tyr Thr Ile Thr Gly Leu Gln Pro Gly Thr
    1955                1960                1965

Asp Tyr Lys Ile Tyr Leu Tyr Thr Leu Asn Asp Asn Ala Arg Ser
    1970                1975                1980

Ser Pro Val Val Ile Asp Ala Ser Thr Ala Ile Asp Ala Pro Ser
    1985                1990                1995

Asn Leu Arg Phe Leu Ala Thr Thr Pro Asn Ser Leu Leu Val Ser
    2000                2005                2010

Trp Gln Pro Pro Arg Ala Arg Ile Thr Gly Tyr Ile Ile Lys Tyr
    2015                2020                2025

Glu Lys Pro Gly Ser Pro Pro Arg Glu Val Val Pro Arg Pro Arg
    2030                2035                2040

Pro Gly Val Thr Glu Ala Thr Ile Thr Gly Leu Glu Pro Gly Thr
    2045                2050                2055

Glu Tyr Thr Ile Tyr Val Ile Ala Leu Lys Asn Asn Gln Lys Ser
    2060                2065                2070

Glu Pro Leu Ile Gly Arg Lys Lys Thr Val Gln Lys Thr Pro Phe
    2075                2080                2085

Val Thr His Pro Gly Tyr Asp Thr Gly Asn Gly Ile Gln Leu Pro
    2090                2095                2100

Gly Thr Ser Gly Gln Gln Pro Ser Val Gly Gln Gln Met Ile Phe
    2105                2110                2115

Glu Glu His Gly Phe Arg Arg Thr Thr Pro Pro Thr Thr Ala Thr
    2120                2125                2130

Pro Ile Arg His Arg Pro Arg Pro Tyr Pro Pro Asn Val Gly Gln
    2135                2140                2145

Glu Ala Leu Ser Gln Thr Thr Ile Ser Trp Ala Pro Phe Gln Asp
    2150                2155                2160

Thr Ser Glu Tyr Ile Ile Ser Cys His Pro Val Gly Thr Asp Glu
    2165                2170                2175

Glu Pro Leu Gln Phe Arg Val Pro Gly Thr Ser Thr Ser Ala Thr
    2180                2185                2190

Leu Thr Gly Leu Thr Arg Gly Ala Thr Tyr Asn Ile Ile Val Glu
    2195                2200                2205

Ala Leu Lys Asp Gln Gln Arg His Lys Val Arg Glu Glu Val Val
    2210                2215                2220

Thr Val Gly Asn Ser Val Asn Glu Gly Leu Asn Gln Pro Thr Asp
```

```
                2225                2230                2235
Asp Ser Cys Phe Asp Pro Tyr Thr Val Ser His Tyr Ala Val Gly
    2240                2245                2250

Asp Glu Trp Glu Arg Met Ser Glu Ser Gly Phe Lys Leu Leu Cys
    2255                2260                2265

Gln Cys Leu Gly Phe Gly Ser Gly His Phe Arg Cys Asp Ser Ser
    2270                2275                2280

Arg Trp Cys His Asp Asn Gly Val Asn Tyr Lys Ile Gly Glu Lys
    2285                2290                2295

Trp Asp Arg Gln Gly Glu Asn Gly Gln Met Met Ser Cys Thr Cys
    2300                2305                2310

Leu Gly Asn Gly Lys Gly Glu Phe Lys Cys Asp Pro His Glu Ala
    2315                2320                2325

Thr Cys Tyr Asp Asp Gly Lys Thr Tyr His Val Gly Glu Gln Trp
    2330                2335                2340

Gln Lys Glu Tyr Leu Gly Ala Ile Cys Ser Cys Thr Cys Phe Gly
    2345                2350                2355

Gly Gln Arg Gly Trp Arg Cys Asp Asn Cys Arg Arg Pro Gly Gly
    2360                2365                2370

Glu Pro Ser Pro Glu Gly Thr Thr Gly Gln Ser Tyr Asn Gln Tyr
    2375                2380                2385

Ser Gln Arg Tyr His Gln Arg Thr Asn Thr Asn Val Asn Cys Pro
    2390                2395                2400

Ile Glu Cys Phe Met Pro Leu Asp Val Gln Ala Asp Arg Glu Asp
    2405                2410                2415

Ser Arg Glu
    2420

<210> SEQ ID NO 227
<211> LENGTH: 2355
<212> TYPE: PRT
<213> ORGANISM: Homo sapiens
<220> FEATURE:
<223> OTHER INFORMATION: Fibronectin 1 isoform 3

<400> SEQUENCE: 227

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
        50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
```

```
            145                 150                 155                 160
        Gly Gly Tyr Met Leu Glu Cys Val Cys Leu Gly Asn Gly Lys Gly Glu
                        165                 170                 175

Trp Thr Cys Lys Pro Ile Ala Glu Lys Cys Phe Asp His Ala Ala Gly
                        180                 185                 190

Thr Ser Tyr Val Val Gly Glu Thr Trp Glu Lys Pro Tyr Gln Gly Trp
                        195                 200                 205

Met Met Val Asp Cys Thr Cys Leu Gly Glu Gly Ser Gly Arg Ile Thr
                210                 215                 220

Cys Thr Ser Arg Asn Arg Cys Asn Asp Gln Asp Thr Arg Thr Ser Tyr
        225                 230                 235                 240

Arg Ile Gly Asp Thr Trp Ser Lys Lys Asp Asn Arg Gly Asn Leu Leu
                        245                 250                 255

Gln Cys Ile Cys Thr Gly Asn Gly Arg Gly Glu Trp Lys Cys Glu Arg
                        260                 265                 270

His Thr Ser Val Gln Thr Thr Ser Ser Gly Ser Gly Pro Phe Thr Asp
                        275                 280                 285

Val Arg Ala Ala Val Tyr Gln Pro Gln Pro His Pro Gln Pro Pro Pro
                290                 295                 300

Tyr Gly His Cys Val Thr Asp Ser Gly Val Val Tyr Ser Val Gly Met
        305                 310                 315                 320

Gln Trp Leu Lys Thr Gln Gly Asn Lys Gln Met Leu Cys Thr Cys Leu
                        325                 330                 335

Gly Asn Gly Val Ser Cys Gln Glu Thr Ala Val Thr Gln Thr Tyr Gly
                        340                 345                 350

Gly Asn Ser Asn Gly Glu Pro Cys Val Leu Pro Phe Thr Tyr Asn Gly
                        355                 360                 365

Arg Thr Phe Tyr Ser Cys Thr Thr Glu Gly Arg Gln Asp Gly His Leu
                        370                 375                 380

Trp Cys Ser Thr Thr Ser Asn Tyr Glu Gln Asp Gln Lys Tyr Ser Phe
        385                 390                 395                 400

Cys Thr Asp His Thr Val Leu Val Gln Thr Arg Gly Gly Asn Ser Asn
                        405                 410                 415

Gly Ala Leu Cys His Phe Pro Phe Leu Tyr Asn Asn His Asn Tyr Thr
                        420                 425                 430

Asp Cys Thr Ser Glu Gly Arg Arg Asp Asn Met Lys Trp Cys Gly Thr
                        435                 440                 445

Thr Gln Asn Tyr Asp Ala Asp Gln Lys Phe Gly Phe Cys Pro Met Ala
                        450                 455                 460

Ala His Glu Glu Ile Cys Thr Thr Asn Glu Gly Val Met Tyr Arg Ile
        465                 470                 475                 480

Gly Asp Gln Trp Asp Lys Gln His Asp Met Gly His Met Met Arg Cys
                        485                 490                 495

Thr Cys Val Gly Asn Gly Arg Gly Glu Trp Thr Cys Ile Ala Tyr Ser
                        500                 505                 510

Gln Leu Arg Asp Gln Cys Ile Val Asp Asp Ile Thr Tyr Asn Val Asn
                        515                 520                 525

Asp Thr Phe His Lys Arg His Glu Glu Gly His Met Leu Asn Cys Thr
                        530                 535                 540

Cys Phe Gly Gln Gly Arg Gly Arg Trp Lys Cys Asp Pro Val Asp Gln
        545                 550                 555                 560

Cys Gln Asp Ser Glu Thr Gly Thr Phe Tyr Gln Ile Gly Asp Ser Trp
                        565                 570                 575
```

-continued

```
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
            595                 600                 605
Ser Gly Pro Val Glu Val Phe Ile Thr Glu Thr Pro Ser Gln Pro Asn
            610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                645                 650                 655
Ala Thr Ile Pro Gly His Leu Asn Ser Tyr Thr Ile Lys Gly Leu Lys
            660                 665                 670
Pro Gly Val Val Tyr Glu Gly Gln Leu Ile Ser Ile Gln Gln Tyr Gly
            675                 680                 685
His Gln Glu Val Thr Arg Phe Asp Phe Thr Thr Ser Thr Ser Thr
            690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
                725                 730                 735
Val Val Ser Trp Val Ser Ala Ser Asp Thr Val Ser Gly Phe Arg Val
            740                 745                 750
Glu Tyr Glu Leu Ser Glu Glu Gly Asp Glu Pro Gln Tyr Leu Asp Leu
            755                 760                 765
Pro Ser Thr Ala Thr Ser Val Asn Ile Pro Asp Leu Leu Pro Gly Arg
            770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
                805                 810                 815
Pro Thr Val Asp Gln Val Asp Asp Thr Ser Ile Val Val Arg Trp Ser
            820                 825                 830
Arg Pro Gln Ala Pro Ile Thr Gly Tyr Arg Ile Val Tyr Ser Pro Ser
            835                 840                 845
Val Glu Gly Ser Ser Thr Glu Leu Asn Leu Pro Glu Thr Ala Asn Ser
            850                 855                 860
Val Thr Leu Ser Asp Leu Gln Pro Gly Val Gln Tyr Asn Ile Thr Ile
865                 870                 875                 880
Tyr Ala Val Glu Glu Asn Gln Glu Ser Thr Pro Val Val Ile Gln Gln
                885                 890                 895
Glu Thr Thr Gly Thr Pro Arg Ser Asp Thr Val Pro Ser Pro Arg Asp
            900                 905                 910
Leu Gln Phe Val Glu Val Thr Asp Val Lys Val Thr Ile Met Trp Thr
            915                 920                 925
Pro Pro Glu Ser Ala Val Thr Gly Tyr Arg Val Asp Val Ile Pro Val
            930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
                965                 970                 975
Val Phe Ala Val Ser His Gly Arg Glu Ser Lys Pro Leu Thr Ala Gln
            980                 985                 990
```

```
Gln Thr Thr Lys Leu Asp Ala Pro  Thr Asn Leu Gln Phe  Val Asn Glu
    995                 1000                      1005

Thr Asp  Ser Thr Val Leu Val Arg Trp Thr Pro  Pro Arg Ala Gln
    1010                 1015                 1020

Ile Thr  Gly Tyr Arg Leu Thr  Val Gly Leu Thr Arg  Arg Gly Gln
    1025                 1030                 1035

Pro Arg  Gln Tyr Asn Val Gly  Pro Ser Val Ser Lys  Tyr Pro Leu
    1040                 1045                 1050

Arg Asn  Leu Gln Pro Ala Ser  Glu Tyr Thr Val Ser  Leu Val Ala
    1055                 1060                 1065

Ile Lys  Gly Asn Gln Glu Ser  Pro Lys Ala Thr Gly  Val Phe Thr
    1070                 1075                 1080

Thr Leu  Gln Pro Gly Ser Ser  Ile Pro Pro Tyr Asn  Thr Glu Val
    1085                 1090                 1095

Thr Glu  Thr Thr Ile Val Ile  Thr Trp Thr Pro Ala  Pro Arg Ile
    1100                 1105                 1110

Gly Phe  Lys Leu Gly Val Arg  Pro Ser Gln Gly Gly  Glu Ala Pro
    1115                 1120                 1125

Arg Glu  Val Thr Ser Asp Ser  Gly Ser Ile Val Val  Ser Gly Leu
    1130                 1135                 1140

Thr Pro  Gly Val Glu Tyr Val  Tyr Thr Ile Gln Val  Leu Arg Asp
    1145                 1150                 1155

Gly Gln  Glu Arg Asp Ala Pro  Ile Val Asn Lys Val  Val Thr Pro
    1160                 1165                 1170

Leu Ser  Pro Pro Thr Asn Leu  His Leu Glu Ala Asn  Pro Asp Thr
    1175                 1180                 1185

Gly Val  Leu Thr Val Ser Trp  Glu Arg Ser Thr Thr  Pro Asp Ile
    1190                 1195                 1200

Thr Gly  Tyr Arg Ile Thr Thr  Thr Pro Thr Asn Gly  Gln Gln Gly
    1205                 1210                 1215

Asn Ser  Leu Glu Glu Val Val  His Ala Asp Gln Ser  Ser Cys Thr
    1220                 1225                 1230

Phe Asp  Asn Leu Ser Pro Gly  Leu Glu Tyr Asn Val  Ser Val Tyr
    1235                 1240                 1245

Thr Val  Lys Asp Asp Lys Glu  Ser Val Pro Ile Ser  Asp Thr Ile
    1250                 1255                 1260

Ile Pro  Ala Val Pro Pro Pro  Thr Asp Leu Arg Phe  Thr Asn Ile
    1265                 1270                 1275

Gly Pro  Asp Thr Met Arg Val  Thr Trp Ala Pro Pro  Pro Ser Ile
    1280                 1285                 1290

Asp Leu  Thr Asn Phe Leu Val  Arg Tyr Ser Pro Val  Lys Asn Glu
    1295                 1300                 1305

Glu Asp  Val Ala Glu Leu Ser  Ile Ser Pro Ser Asp  Asn Ala Val
    1310                 1315                 1320

Val Leu  Thr Asn Leu Leu Pro  Gly Thr Glu Tyr Val  Val Ser Val
    1325                 1330                 1335

Ser Ser  Val Tyr Glu Gln His  Glu Ser Thr Pro Leu  Arg Gly Arg
    1340                 1345                 1350

Gln Lys  Thr Gly Leu Asp Ser  Pro Thr Gly Ile Asp  Phe Ser Asp
    1355                 1360                 1365

Ile Thr  Ala Asn Ser Phe Thr  Val His Trp Ile Ala  Pro Arg Ala
    1370                 1375                 1380

Thr Ile  Thr Gly Tyr Arg Ile  Arg His His Pro Glu  His Phe Ser
```

```
            1385                1390                1395
Gly Arg Pro Arg Glu Asp Arg Val Pro His Ser Arg Asn Ser Ile
        1400                1405                1410
Thr Leu Thr Asn Leu Thr Pro Gly Thr Glu Tyr Val Val Ser Ile
        1415                1420                1425
Val Ala Leu Asn Gly Arg Glu Glu Ser Pro Leu Leu Ile Gly Gln
        1430                1435                1440
Gln Ser Thr Val Ser Asp Val Pro Arg Asp Leu Glu Val Val Ala
        1445                1450                1455
Ala Thr Pro Thr Ser Leu Leu Ile Ser Trp Asp Ala Pro Ala Val
        1460                1465                1470
Thr Val Arg Tyr Tyr Arg Ile Thr Tyr Gly Glu Thr Gly Gly Asn
        1475                1480                1485
Ser Pro Val Gln Glu Phe Thr Val Pro Gly Ser Lys Ser Thr Ala
        1490                1495                1500
Thr Ile Ser Gly Leu Lys Pro Gly Val Asp Tyr Thr Ile Thr Val
        1505                1510                1515
Tyr Ala Val Thr Gly Arg Gly Asp Ser Pro Ala Ser Ser Lys Pro
        1520                1525                1530
Ile Ser Ile Asn Tyr Arg Thr Glu Ile Asp Lys Pro Ser Gln Met
        1535                1540                1545
Gln Val Thr Asp Val Gln Asp Asn Ser Ile Ser Val Lys Trp Leu
        1550                1555                1560
Pro Ser Ser Ser Pro Val Thr Gly Tyr Arg Val Thr Thr Thr Pro
        1565                1570                1575
Lys Asn Gly Pro Gly Pro Thr Lys Thr Lys Thr Ala Gly Pro Asp
        1580                1585                1590
Gln Thr Glu Met Thr Ile Glu Gly Leu Gln Pro Thr Val Glu Tyr
        1595                1600                1605
Val Val Ser Val Tyr Ala Gln Asn Pro Ser Gly Glu Ser Gln Pro
        1610                1615                1620
Leu Val Gln Thr Ala Val Thr Asn Ile Asp Arg Pro Lys Gly Leu
        1625                1630                1635
Ala Phe Thr Asp Val Asp Val Asp Ser Ile Lys Ile Ala Trp Glu
        1640                1645                1650
Ser Pro Gln Gly Gln Val Ser Arg Tyr Arg Val Thr Tyr Ser Ser
        1655                1660                1665
Pro Glu Asp Gly Ile His Glu Leu Phe Pro Ala Pro Asp Gly Glu
        1670                1675                1680
Glu Asp Thr Ala Glu Leu Gln Gly Leu Arg Pro Gly Ser Glu Tyr
        1685                1690                1695
Thr Val Ser Val Val Ala Leu His Asp Asp Met Glu Ser Gln Pro
        1700                1705                1710
Leu Ile Gly Thr Gln Ser Thr Ala Ile Pro Ala Pro Thr Asp Leu
        1715                1720                1725
Lys Phe Thr Gln Val Thr Pro Thr Ser Leu Ser Ala Gln Trp Thr
        1730                1735                1740
Pro Pro Asn Val Gln Leu Thr Gly Tyr Arg Val Arg Val Thr Pro
        1745                1750                1755
Lys Glu Lys Thr Gly Pro Met Lys Glu Ile Asn Leu Ala Pro Asp
        1760                1765                1770
Ser Ser Ser Val Val Val Ser Gly Leu Met Val Ala Thr Lys Tyr
        1775                1780                1785
```

```
Glu Val Ser Val Tyr Ala Leu Lys Asp Thr Leu Thr Ser Arg Pro
    1790            1795                1800

Ala Gln Gly Val Val Thr Thr Leu Glu Asn Val Ser Pro Pro Arg
    1805            1810                1815

Arg Ala Arg Val Thr Asp Ala Thr Glu Thr Thr Ile Thr Ile Ser
    1820            1825                1830

Trp Arg Thr Lys Thr Glu Thr Ile Thr Gly Phe Gln Val Asp Ala
    1835            1840                1845

Val Pro Ala Asn Gly Gln Thr Pro Ile Gln Arg Thr Ile Lys Pro
    1850            1855                1860

Asp Val Arg Ser Tyr Thr Ile Thr Gly Leu Gln Pro Gly Thr Asp
    1865            1870                1875

Tyr Lys Ile Tyr Leu Tyr Thr Leu Asn Asp Asn Ala Arg Ser Ser
    1880            1885                1890

Pro Val Val Ile Asp Ala Ser Thr Ala Ile Asp Ala Pro Ser Asn
    1895            1900                1905

Leu Arg Phe Leu Ala Thr Thr Pro Asn Ser Leu Leu Val Ser Trp
    1910            1915                1920

Gln Pro Pro Arg Ala Arg Ile Thr Gly Tyr Ile Ile Lys Tyr Glu
    1925            1930                1935

Lys Pro Gly Ser Pro Pro Arg Glu Val Val Pro Arg Pro Arg Pro
    1940            1945                1950

Gly Val Thr Glu Ala Thr Ile Thr Gly Leu Glu Pro Gly Thr Glu
    1955            1960                1965

Tyr Thr Ile Tyr Val Ile Ala Leu Lys Asn Asn Gln Lys Ser Glu
    1970            1975                1980

Pro Leu Ile Gly Arg Lys Lys Thr Asp Glu Leu Pro Gln Leu Val
    1985            1990                1995

Thr Leu Pro His Pro Asn Leu His Gly Pro Glu Ile Leu Asp Val
    2000            2005                2010

Pro Ser Thr Val Gln Lys Thr Pro Phe Val Thr His Pro Gly Tyr
    2015            2020                2025

Asp Thr Gly Asn Gly Ile Gln Leu Pro Gly Thr Ser Gly Gln Gln
    2030            2035                2040

Pro Ser Val Gly Gln Gln Met Ile Phe Glu Glu His Gly Phe Arg
    2045            2050                2055

Arg Thr Thr Pro Pro Thr Thr Ala Thr Pro Ile Arg His Arg Pro
    2060            2065                2070

Arg Pro Tyr Pro Pro Asn Val Gly Gln Glu Ala Leu Ser Gln Thr
    2075            2080                2085

Thr Ile Ser Trp Ala Pro Phe Gln Asp Thr Ser Glu Tyr Ile Ile
    2090            2095                2100

Ser Cys His Pro Val Gly Thr Asp Glu Glu Pro Leu Gln Phe Arg
    2105            2110                2115

Val Pro Gly Thr Ser Thr Ser Ala Thr Leu Thr Gly Leu Thr Arg
    2120            2125                2130

Gly Ala Thr Tyr Asn Ile Ile Val Glu Ala Leu Lys Asp Gln Gln
    2135            2140                2145

Arg His Lys Val Arg Glu Glu Val Val Thr Val Gly Asn Ser Val
    2150            2155                2160

Asn Glu Gly Leu Asn Gln Pro Thr Asp Asp Ser Cys Phe Asp Pro
    2165            2170                2175
```

```
Tyr Thr Val Ser His Tyr Ala Val Gly Asp Glu Trp Glu Arg Met
    2180                2185                2190

Ser Glu Ser Gly Phe Lys Leu Leu Cys Gln Cys Leu Gly Phe Gly
2195                2200                2205

Ser Gly His Phe Arg Cys Asp Ser Ser Arg Trp Cys His Asp Asn
    2210                2215                2220

Gly Val Asn Tyr Lys Ile Gly Glu Lys Trp Asp Arg Gln Gly Glu
        2225                2230                2235

Asn Gly Gln Met Met Ser Cys Thr Cys Leu Gly Asn Gly Lys Gly
    2240                2245                2250

Glu Phe Lys Cys Asp Pro His Glu Ala Thr Cys Tyr Asp Asp Gly
2255                2260                2265

Lys Thr Tyr His Val Gly Glu Gln Trp Gln Lys Glu Tyr Leu Gly
    2270                2275                2280

Ala Ile Cys Ser Cys Thr Cys Phe Gly Gly Gln Arg Gly Trp Arg
    2285                2290                2295

Cys Asp Asn Cys Arg Arg Pro Gly Gly Glu Pro Ser Pro Glu Gly
    2300                2305                2310

Thr Thr Gly Gln Ser Tyr Asn Gln Tyr Ser Gln Arg Tyr His Gln
    2315                2320                2325

Arg Thr Asn Thr Asn Val Asn Cys Pro Ile Glu Cys Phe Met Pro
    2330                2335                2340

Leu Asp Val Gln Ala Asp Arg Glu Asp Ser Arg Glu
    2345                2350                2355

<210> SEQ ID NO 228
<211> LENGTH: 2330
<212> TYPE: PRT
<213> ORGANISM: Homo sapiens
<220> FEATURE:
<223> OTHER INFORMATION: Fibronectin 1 isoform 4

<400> SEQUENCE: 228

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175
```

-continued

```
Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
```

```
                595                 600                 605
    Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
    625                 630                 635                 640

Tyr Ile Leu Arg Trp Arg Pro Lys Asn Ser Val Gly Arg Trp Lys Glu
                    645                 650                 655

Ala Thr Ile Pro Gly His Leu Asn Ser Tyr Thr Ile Lys Gly Leu Lys
                    660                 665                 670

Pro Gly Val Val Tyr Glu Gly Gln Leu Ile Ser Ile Gln Gln Tyr Gly
                    675                 680                 685

His Gln Glu Val Thr Arg Phe Asp Phe Thr Thr Thr Ser Thr Ser Thr
                690                 695                 700

Pro Val Thr Ser Asn Thr Val Thr Gly Glu Thr Thr Pro Phe Ser Pro
    705                 710                 715                 720

Leu Val Ala Thr Ser Glu Ser Val Thr Glu Ile Thr Ala Ser Ser Phe
                    725                 730                 735

Val Val Ser Trp Val Ser Ala Ser Asp Thr Val Ser Gly Phe Arg Val
                    740                 745                 750

Glu Tyr Glu Leu Ser Glu Glu Gly Asp Glu Pro Gln Tyr Leu Asp Leu
                    755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
    785                 790                 795                 800

Leu Ile Leu Ser Thr Ser Gln Thr Thr Ala Pro Asp Ala Pro Pro Asp
                    805                 810                 815

Pro Thr Val Asp Gln Val Asp Asp Thr Ser Ile Val Val Arg Trp Ser
                    820                 825                 830

Arg Pro Gln Ala Pro Ile Thr Gly Tyr Arg Ile Val Tyr Ser Pro Ser
                    835                 840                 845

Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
    865                 870                 875                 880

Tyr Ala Val Glu Glu Asn Gln Glu Ser Thr Pro Val Val Ile Gln Gln
                    885                 890                 895

Glu Thr Thr Gly Thr Pro Arg Ser Asp Thr Val Pro Ser Pro Arg Asp
                    900                 905                 910

Leu Gln Phe Val Glu Val Thr Asp Val Lys Val Thr Ile Met Trp Thr
                    915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
    945                 950                 955                 960

Phe Ala Glu Val Thr Gly Leu Ser Pro Gly Val Thr Tyr Tyr Phe Lys
                    965                 970                 975

Val Phe Ala Val Ser His Gly Arg Glu Ser Lys Pro Leu Thr Ala Gln
                    980                 985                 990

Gln Thr Thr Lys Leu Asp Ala Pro  Thr Asn Leu Gln Phe  Val Asn Glu
                    995                  1000                 1005

Thr Asp Ser Thr Val Leu Val Arg Trp Thr Pro Pro  Arg Ala Gln
                1010                1015                1020
```

-continued

```
Ile Thr Gly Tyr Arg Leu Thr Val Gly Leu Thr Arg Arg Gly Gln
1025                1030                1035

Pro Arg Gln Tyr Asn Val Gly Pro Ser Val Ser Lys Tyr Pro Leu
1040                1045                1050

Arg Asn Leu Gln Pro Ala Ser Glu Tyr Thr Val Ser Leu Val Ala
1055                1060                1065

Ile Lys Gly Asn Gln Glu Ser Pro Lys Ala Thr Gly Val Phe Thr
1070                1075                1080

Thr Leu Gln Pro Gly Ser Ser Ile Pro Pro Tyr Asn Thr Glu Val
1085                1090                1095

Thr Glu Thr Thr Ile Val Ile Thr Trp Thr Pro Ala Pro Arg Ile
1100                1105                1110

Gly Phe Lys Leu Gly Val Arg Pro Ser Gln Gly Gly Glu Ala Pro
1115                1120                1125

Arg Glu Val Thr Ser Asp Ser Gly Ser Ile Val Val Ser Gly Leu
1130                1135                1140

Thr Pro Gly Val Glu Tyr Val Tyr Thr Ile Gln Val Leu Arg Asp
1145                1150                1155

Gly Gln Glu Arg Asp Ala Pro Ile Val Asn Lys Val Val Thr Pro
1160                1165                1170

Leu Ser Pro Pro Thr Asn Leu His Leu Glu Ala Asn Pro Asp Thr
1175                1180                1185

Gly Val Leu Thr Val Ser Trp Glu Arg Ser Thr Thr Pro Asp Ile
1190                1195                1200

Thr Gly Tyr Arg Ile Thr Thr Thr Pro Thr Asn Gly Gln Gln Gly
1205                1210                1215

Asn Ser Leu Glu Glu Val Val His Ala Asp Gln Ser Ser Cys Thr
1220                1225                1230

Phe Asp Asn Leu Ser Pro Gly Leu Glu Tyr Asn Val Ser Val Tyr
1235                1240                1245

Thr Val Lys Asp Asp Lys Glu Ser Val Pro Ile Ser Asp Thr Ile
1250                1255                1260

Ile Pro Ala Val Pro Pro Pro Thr Asp Leu Arg Phe Thr Asn Ile
1265                1270                1275

Gly Pro Asp Thr Met Arg Val Thr Trp Ala Pro Pro Pro Ser Ile
1280                1285                1290

Asp Leu Thr Asn Phe Leu Val Arg Tyr Ser Pro Val Lys Asn Glu
1295                1300                1305

Glu Asp Val Ala Glu Leu Ser Ile Ser Pro Ser Asp Asn Ala Val
1310                1315                1320

Val Leu Thr Asn Leu Leu Pro Gly Thr Glu Tyr Val Val Ser Val
1325                1330                1335

Ser Ser Val Tyr Glu Gln His Glu Ser Thr Pro Leu Arg Gly Arg
1340                1345                1350

Gln Lys Thr Gly Leu Asp Ser Pro Thr Gly Ile Asp Phe Ser Asp
1355                1360                1365

Ile Thr Ala Asn Ser Phe Thr Val His Trp Ile Ala Pro Arg Ala
1370                1375                1380

Thr Ile Thr Gly Tyr Arg Ile Arg His His Pro Glu His Phe Ser
1385                1390                1395

Gly Arg Pro Arg Glu Asp Arg Val Pro His Ser Arg Asn Ser Ile
1400                1405                1410
```

```
Thr Leu Thr Asn Leu Thr Pro Gly Thr Glu Tyr Val Val Ser Ile
1415                1420                1425

Val Ala Leu Asn Gly Arg Glu Glu Ser Pro Leu Leu Ile Gly Gln
1430                1435                1440

Gln Ser Thr Val Ser Asp Val Pro Arg Asp Leu Glu Val Val Ala
1445                1450                1455

Ala Thr Pro Thr Ser Leu Leu Ile Ser Trp Asp Ala Pro Ala Val
1460                1465                1470

Thr Val Arg Tyr Tyr Arg Ile Thr Tyr Gly Glu Thr Gly Gly Asn
1475                1480                1485

Ser Pro Val Gln Glu Phe Thr Val Pro Gly Ser Lys Ser Thr Ala
1490                1495                1500

Thr Ile Ser Gly Leu Lys Pro Gly Val Asp Tyr Thr Ile Thr Val
1505                1510                1515

Tyr Ala Val Thr Gly Arg Gly Asp Ser Pro Ala Ser Ser Lys Pro
1520                1525                1530

Ile Ser Ile Asn Tyr Arg Thr Glu Ile Asp Lys Pro Ser Gln Met
1535                1540                1545

Gln Val Thr Asp Val Gln Asp Asn Ser Ile Ser Val Lys Trp Leu
1550                1555                1560

Pro Ser Ser Ser Pro Val Thr Gly Tyr Arg Val Thr Thr Thr Pro
1565                1570                1575

Lys Asn Gly Pro Gly Pro Thr Lys Thr Lys Thr Ala Gly Pro Asp
1580                1585                1590

Gln Thr Glu Met Thr Ile Glu Gly Leu Gln Pro Thr Val Glu Tyr
1595                1600                1605

Val Val Ser Val Tyr Ala Gln Asn Pro Ser Gly Glu Ser Gln Pro
1610                1615                1620

Leu Val Gln Thr Ala Val Thr Asn Ile Asp Arg Pro Lys Gly Leu
1625                1630                1635

Ala Phe Thr Asp Val Asp Val Asp Ser Ile Lys Ile Ala Trp Glu
1640                1645                1650

Ser Pro Gln Gly Gln Val Ser Arg Tyr Arg Val Thr Tyr Ser Ser
1655                1660                1665

Pro Glu Asp Gly Ile His Glu Leu Phe Pro Ala Pro Asp Gly Glu
1670                1675                1680

Glu Asp Thr Ala Glu Leu Gln Gly Leu Arg Pro Gly Ser Glu Tyr
1685                1690                1695

Thr Val Ser Val Val Ala Leu His Asp Asp Met Glu Ser Gln Pro
1700                1705                1710

Leu Ile Gly Thr Gln Ser Thr Ala Ile Pro Ala Pro Thr Asp Leu
1715                1720                1725

Lys Phe Thr Gln Val Thr Pro Thr Ser Leu Ser Ala Gln Trp Thr
1730                1735                1740

Pro Pro Asn Val Gln Leu Thr Gly Tyr Arg Val Arg Val Thr Pro
1745                1750                1755

Lys Glu Lys Thr Gly Pro Met Lys Glu Ile Asn Leu Ala Pro Asp
1760                1765                1770

Ser Ser Ser Val Val Val Ser Gly Leu Met Val Ala Thr Lys Tyr
1775                1780                1785

Glu Val Ser Val Tyr Ala Leu Lys Asp Thr Leu Thr Ser Arg Pro
1790                1795                1800

Ala Gln Gly Val Val Thr Thr Leu Glu Asn Val Ser Pro Pro Arg
```

```
             1805                1810                1815
Arg Ala Arg Val Thr Asp Ala Thr Glu Thr Thr Ile Thr Ile Ser
         1820                1825                1830
Trp Arg Thr Lys Thr Glu Thr Ile Thr Gly Phe Gln Val Asp Ala
         1835                1840                1845
Val Pro Ala Asn Gly Gln Thr Pro Ile Gln Arg Thr Ile Lys Pro
         1850                1855                1860
Asp Val Arg Ser Tyr Thr Ile Thr Gly Leu Gln Pro Gly Thr Asp
         1865                1870                1875
Tyr Lys Ile Tyr Leu Tyr Thr Leu Asn Asp Asn Ala Arg Ser Ser
         1880                1885                1890
Pro Val Val Ile Asp Ala Ser Thr Ala Ile Asp Ala Pro Ser Asn
         1895                1900                1905
Leu Arg Phe Leu Ala Thr Thr Pro Asn Ser Leu Leu Val Ser Trp
         1910                1915                1920
Gln Pro Pro Arg Ala Arg Ile Thr Gly Tyr Ile Ile Lys Tyr Glu
         1925                1930                1935
Lys Pro Gly Ser Pro Pro Arg Glu Val Val Pro Arg Pro Arg Pro
         1940                1945                1950
Gly Val Thr Glu Ala Thr Ile Thr Gly Leu Glu Pro Gly Thr Glu
         1955                1960                1965
Tyr Thr Ile Tyr Val Ile Ala Leu Lys Asn Asn Gln Lys Ser Glu
         1970                1975                1980
Pro Leu Ile Gly Arg Lys Lys Thr Val Gln Lys Thr Pro Phe Val
         1985                1990                1995
Thr His Pro Gly Tyr Asp Thr Gly Asn Gly Ile Gln Leu Pro Gly
         2000                2005                2010
Thr Ser Gly Gln Gln Pro Ser Val Gly Gln Gln Met Ile Phe Glu
         2015                2020                2025
Glu His Gly Phe Arg Arg Thr Thr Pro Pro Thr Thr Ala Thr Pro
         2030                2035                2040
Ile Arg His Arg Pro Arg Pro Tyr Pro Pro Asn Val Gly Gln Glu
         2045                2050                2055
Ala Leu Ser Gln Thr Thr Ile Ser Trp Ala Pro Phe Gln Asp Thr
         2060                2065                2070
Ser Glu Tyr Ile Ile Ser Cys His Pro Val Gly Thr Asp Glu Glu
         2075                2080                2085
Pro Leu Gln Phe Arg Val Pro Gly Thr Ser Thr Ser Ala Thr Leu
         2090                2095                2100
Thr Gly Leu Thr Arg Gly Ala Thr Tyr Asn Ile Ile Val Glu Ala
         2105                2110                2115
Leu Lys Asp Gln Gln Arg His Lys Val Arg Glu Glu Val Val Thr
         2120                2125                2130
Val Gly Asn Ser Val Asn Glu Gly Leu Asn Gln Pro Thr Asp Asp
         2135                2140                2145
Ser Cys Phe Asp Pro Tyr Thr Val Ser His Tyr Ala Val Gly Asp
         2150                2155                2160
Glu Trp Glu Arg Met Ser Glu Ser Gly Phe Lys Leu Leu Cys Gln
         2165                2170                2175
Cys Leu Gly Phe Gly Ser Gly His Phe Arg Cys Asp Ser Ser Arg
         2180                2185                2190
Trp Cys His Asp Asn Gly Val Asn Tyr Lys Ile Gly Glu Lys Trp
         2195                2200                2205
```

```
Asp Arg Gln Gly Glu Asn Gly Gln Met Met Ser Cys Thr Cys Leu
2210            2215                2220

Gly Asn Gly Lys Gly Glu Phe Lys Cys Asp Pro His Glu Ala Thr
    2225            2230                2235

Cys Tyr Asp Asp Gly Lys Thr Tyr His Val Gly Glu Gln Trp Gln
    2240            2245                2250

Lys Glu Tyr Leu Gly Ala Ile Cys Ser Cys Thr Cys Phe Gly Gly
    2255            2260                2265

Gln Arg Gly Trp Arg Cys Asp Asn Cys Arg Arg Pro Gly Gly Glu
    2270            2275                2280

Pro Ser Pro Glu Gly Thr Thr Gly Gln Ser Tyr Asn Gln Tyr Ser
    2285            2290                2295

Gln Arg Tyr His Gln Arg Thr Asn Thr Asn Val Asn Cys Pro Ile
    2300            2305                2310

Glu Cys Phe Met Pro Leu Asp Val Gln Ala Asp Arg Glu Asp Ser
    2315            2320                2325

Arg Glu
    2330

<210> SEQ ID NO 229
<211> LENGTH: 2296
<212> TYPE: PRT
<213> ORGANISM: Homo sapiens
<220> FEATURE:
<223> OTHER INFORMATION: Fibronectin 1 isoform 5

<400> SEQUENCE: 229

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220
```

```
Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
            245                 250                 255

Gln Cys Ile Cys Thr Gly Asn Gly Arg Gly Glu Trp Lys Cys Glu Arg
        260                 265                 270

His Thr Ser Val Gln Thr Thr Ser Ser Gly Ser Gly Pro Phe Thr Asp
    275                 280                 285

Val Arg Ala Ala Val Tyr Gln Pro Gln Pro His Pro Gln Pro Pro Pro
290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
610                 615                 620

Ser His Pro Ile Gln Trp Asn Ala Pro Gln Pro Ser His Ile Ser Lys
625                 630                 635                 640
```

-continued

```
Tyr Ile Leu Arg Trp Arg Pro Lys Asn Ser Val Gly Arg Trp Lys Glu
                645                 650                 655
Ala Thr Ile Pro Gly His Leu Asn Ser Tyr Thr Ile Lys Gly Leu Lys
            660                 665                 670
Pro Gly Val Val Tyr Glu Gly Gln Leu Ile Ser Ile Gln Gln Tyr Gly
        675                 680                 685
His Gln Glu Val Thr Arg Phe Asp Phe Thr Thr Ser Thr Ser Thr
    690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
                725                 730                 735
Val Val Ser Trp Val Ser Ala Ser Asp Thr Val Ser Gly Phe Arg Val
            740                 745                 750
Glu Tyr Glu Leu Ser Glu Gly Asp Glu Pro Gln Tyr Leu Asp Leu
        755                 760                 765
Pro Ser Thr Ala Thr Ser Val Asn Ile Pro Asp Leu Leu Pro Gly Arg
    770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Asp
                805                 810                 815
Pro Thr Val Asp Gln Val Asp Asp Thr Ser Ile Val Val Arg Trp Ser
            820                 825                 830
Arg Pro Gln Ala Pro Ile Thr Gly Tyr Arg Ile Val Tyr Ser Pro Ser
        835                 840                 845
Val Glu Gly Ser Ser Thr Glu Leu Asn Leu Pro Glu Thr Ala Asn Ser
    850                 855                 860
Val Thr Leu Ser Asp Leu Gln Pro Gly Val Gln Tyr Asn Ile Thr Ile
865                 870                 875                 880
Tyr Ala Val Glu Glu Asn Gln Glu Ser Thr Pro Val Val Ile Gln Gln
                885                 890                 895
Glu Thr Thr Gly Thr Pro Arg Ser Asp Thr Val Pro Ser Pro Arg Asp
            900                 905                 910
Leu Gln Phe Val Glu Val Thr Asp Val Lys Val Thr Ile Met Trp Thr
        915                 920                 925
Pro Pro Glu Ser Ala Val Thr Gly Tyr Arg Val Asp Val Ile Pro Val
    930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
                965                 970                 975
Val Phe Ala Val Ser His Gly Arg Glu Ser Lys Pro Leu Thr Ala Gln
            980                 985                 990
Gln Thr Thr Lys Leu Asp Ala Pro Thr Asn Leu Gln Phe Val Asn Glu
        995                 1000                1005
Thr Asp Ser Thr Val Leu Val Arg Trp Thr Pro Pro Arg Ala Gln
    1010                1015                1020
Ile Thr Gly Tyr Arg Leu Thr Val Gly Leu Thr Arg Arg Gly Gln
    1025                1030                1035
Pro Arg Gln Tyr Asn Val Gly Pro Ser Val Ser Lys Tyr Pro Leu
    1040                1045                1050
Arg Asn Leu Gln Pro Ala Ser Glu Tyr Thr Val Ser Leu Val Ala
```

-continued

|      | 1055 |      |      | 1060 |      |      | 1065 |      |      |
| --- | --- | --- | --- | --- | --- | --- | --- | --- | --- |
| Ile | Lys | Gly | Asn | Gln | Glu | Ser | Pro | Lys | Ala | Thr | Gly | Val | Phe | Thr |
|     |     | 1070 |     |     |     | 1075 |     |     |     | 1080 |

Thr Leu Gln Pro Gly Ser Ser Ile Pro Pro Tyr Asn Thr Glu Val
     1085             1090             1095

Thr Glu Thr Thr Ile Val Ile Thr Trp Thr Pro Ala Pro Arg Ile
     1100             1105             1110

Gly Phe Lys Leu Gly Val Arg Pro Ser Gln Gly Gly Glu Ala Pro
     1115             1120             1125

Arg Glu Val Thr Ser Asp Ser Gly Ser Ile Val Val Ser Gly Leu
     1130             1135             1140

Thr Pro Gly Val Glu Tyr Val Tyr Thr Ile Gln Val Leu Arg Asp
     1145             1150             1155

Gly Gln Glu Arg Asp Ala Pro Ile Val Asn Lys Val Val Thr Pro
     1160             1165             1170

Leu Ser Pro Pro Thr Asn Leu His Leu Glu Ala Asn Pro Asp Thr
     1175             1180             1185

Gly Val Leu Thr Val Ser Trp Glu Arg Ser Thr Thr Pro Asp Ile
     1190             1195             1200

Thr Gly Tyr Arg Ile Thr Thr Thr Pro Thr Asn Gly Gln Gln Gly
     1205             1210             1215

Asn Ser Leu Glu Glu Val Val His Ala Asp Gln Ser Ser Cys Thr
     1220             1225             1230

Phe Asp Asn Leu Ser Pro Gly Leu Glu Tyr Asn Val Ser Val Tyr
     1235             1240             1245

Thr Val Lys Asp Asp Lys Glu Ser Val Pro Ile Ser Asp Thr Ile
     1250             1255             1260

Ile Pro Ala Val Pro Pro Thr Asp Leu Arg Phe Thr Asn Ile
     1265             1270             1275

Gly Pro Asp Thr Met Arg Val Thr Trp Ala Pro Pro Ser Ile
     1280             1285             1290

Asp Leu Thr Asn Phe Leu Val Arg Tyr Ser Pro Val Lys Asn Glu
     1295             1300             1305

Glu Asp Val Ala Glu Leu Ser Ile Ser Pro Ser Asp Asn Ala Val
     1310             1315             1320

Val Leu Thr Asn Leu Leu Pro Gly Thr Glu Tyr Val Val Ser Val
     1325             1330             1335

Ser Ser Val Tyr Glu Gln His Glu Ser Thr Pro Leu Arg Gly Arg
     1340             1345             1350

Gln Lys Thr Gly Leu Asp Ser Pro Thr Gly Ile Asp Phe Ser Asp
     1355             1360             1365

Ile Thr Ala Asn Ser Phe Thr Val His Trp Ile Ala Pro Arg Ala
     1370             1375             1380

Thr Ile Thr Gly Tyr Arg Ile Arg His His Pro Glu His Phe Ser
     1385             1390             1395

Gly Arg Pro Arg Glu Asp Arg Val Pro His Ser Arg Asn Ser Ile
     1400             1405             1410

Thr Leu Thr Asn Leu Thr Pro Gly Thr Glu Tyr Val Val Ser Ile
     1415             1420             1425

Val Ala Leu Asn Gly Arg Glu Glu Ser Pro Leu Leu Ile Gly Gln
     1430             1435             1440

Gln Ser Thr Val Ser Asp Val Pro Arg Asp Leu Glu Val Val Ala
     1445             1450             1455

```
Ala Thr Pro Thr Ser Leu Leu Ile Ser Trp Asp Ala Pro Ala Val
1460                1465                1470

Thr Val Arg Tyr Tyr Arg Ile Thr Tyr Gly Glu Thr Gly Gly Asn
1475                1480                1485

Ser Pro Val Gln Glu Phe Thr Val Pro Gly Ser Lys Ser Thr Ala
1490                1495                1500

Thr Ile Ser Gly Leu Lys Pro Gly Val Asp Tyr Thr Ile Thr Val
1505                1510                1515

Tyr Ala Val Thr Gly Arg Gly Asp Ser Pro Ala Ser Ser Lys Pro
1520                1525                1530

Ile Ser Ile Asn Tyr Arg Thr Glu Ile Asp Lys Pro Ser Gln Met
1535                1540                1545

Gln Val Thr Asp Val Gln Asp Asn Ser Ile Ser Val Lys Trp Leu
1550                1555                1560

Pro Ser Ser Ser Pro Val Thr Gly Tyr Arg Val Thr Thr Thr Pro
1565                1570                1575

Lys Asn Gly Pro Gly Pro Thr Lys Thr Lys Thr Ala Gly Pro Asp
1580                1585                1590

Gln Thr Glu Met Thr Ile Glu Gly Leu Gln Pro Thr Val Glu Tyr
1595                1600                1605

Val Val Ser Val Tyr Ala Gln Asn Pro Ser Gly Glu Ser Gln Pro
1610                1615                1620

Leu Val Gln Thr Ala Val Thr Thr Ile Pro Ala Pro Thr Asp Leu
1625                1630                1635

Lys Phe Thr Gln Val Thr Pro Thr Ser Leu Ser Ala Gln Trp Thr
1640                1645                1650

Pro Pro Asn Val Gln Leu Thr Gly Tyr Arg Val Arg Val Thr Pro
1655                1660                1665

Lys Glu Lys Thr Gly Pro Met Lys Glu Ile Asn Leu Ala Pro Asp
1670                1675                1680

Ser Ser Ser Val Val Val Ser Gly Leu Met Val Ala Thr Lys Tyr
1685                1690                1695

Glu Val Ser Val Tyr Ala Leu Lys Asp Thr Leu Thr Ser Arg Pro
1700                1705                1710

Ala Gln Gly Val Val Thr Thr Leu Glu Asn Val Ser Pro Pro Arg
1715                1720                1725

Arg Ala Arg Val Thr Asp Ala Thr Glu Thr Thr Ile Thr Ile Ser
1730                1735                1740

Trp Arg Thr Lys Thr Glu Thr Ile Thr Gly Phe Gln Val Asp Ala
1745                1750                1755

Val Pro Ala Asn Gly Gln Thr Pro Ile Gln Arg Thr Ile Lys Pro
1760                1765                1770

Asp Val Arg Ser Tyr Thr Ile Thr Gly Leu Gln Pro Gly Thr Asp
1775                1780                1785

Tyr Lys Ile Tyr Leu Tyr Thr Leu Asn Asp Asn Ala Arg Ser Ser
1790                1795                1800

Pro Val Val Ile Asp Ala Ser Thr Ala Ile Asp Ala Pro Ser Asn
1805                1810                1815

Leu Arg Phe Leu Ala Thr Thr Pro Asn Ser Leu Leu Val Ser Trp
1820                1825                1830

Gln Pro Pro Arg Ala Arg Ile Thr Gly Tyr Ile Ile Lys Tyr Glu
1835                1840                1845
```

```
Lys Pro Gly Ser Pro Pro Arg Glu Val Pro Arg Pro Arg Pro
1850             1855             1860

Gly Val Thr Glu Ala Thr Ile Thr Gly Leu Glu Pro Gly Thr Glu
1865             1870             1875

Tyr Thr Ile Tyr Val Ile Ala Leu Lys Asn Asn Gln Lys Ser Glu
1880             1885             1890

Pro Leu Ile Gly Arg Lys Lys Thr Asp Glu Leu Pro Gln Leu Val
1895             1900             1905

Thr Leu Pro His Pro Asn Leu His Gly Pro Glu Ile Leu Asp Val
1910             1915             1920

Pro Ser Thr Val Gln Lys Thr Pro Phe Val Thr His Pro Gly Tyr
1925             1930             1935

Asp Thr Gly Asn Gly Ile Gln Leu Pro Gly Thr Ser Gly Gln Gln
1940             1945             1950

Pro Ser Val Gly Gln Gln Met Ile Phe Glu Glu His Gly Phe Arg
1955             1960             1965

Arg Thr Thr Pro Pro Thr Thr Ala Thr Pro Ile Arg His Arg Pro
1970             1975             1980

Arg Pro Tyr Pro Pro Asn Val Gly Glu Glu Ile Gln Ile Gly His
1985             1990             1995

Ile Pro Arg Glu Asp Val Asp Tyr His Leu Tyr Pro His Gly Pro
2000             2005             2010

Gly Leu Asn Pro Asn Ala Ser Thr Gly Gln Glu Ala Leu Ser Gln
2015             2020             2025

Thr Thr Ile Ser Trp Ala Pro Phe Gln Asp Thr Ser Glu Tyr Ile
2030             2035             2040

Ile Ser Cys His Pro Val Gly Thr Asp Glu Glu Pro Leu Gln Phe
2045             2050             2055

Arg Val Pro Gly Thr Ser Thr Ser Ala Thr Leu Thr Gly Leu Thr
2060             2065             2070

Arg Gly Ala Thr Tyr Asn Ile Ile Val Glu Ala Leu Lys Asp Gln
2075             2080             2085

Gln Arg His Lys Val Arg Glu Glu Val Val Thr Val Gly Asn Ser
2090             2095             2100

Val Asn Glu Gly Leu Asn Gln Pro Thr Asp Asp Ser Cys Phe Asp
2105             2110             2115

Pro Tyr Thr Val Ser His Tyr Ala Val Gly Asp Glu Trp Glu Arg
2120             2125             2130

Met Ser Glu Ser Gly Phe Lys Leu Leu Cys Gln Cys Leu Gly Phe
2135             2140             2145

Gly Ser Gly His Phe Arg Cys Asp Ser Ser Arg Trp Cys His Asp
2150             2155             2160

Asn Gly Val Asn Tyr Lys Ile Gly Glu Lys Trp Asp Arg Gln Gly
2165             2170             2175

Glu Asn Gly Gln Met Met Ser Cys Thr Cys Leu Gly Asn Gly Lys
2180             2185             2190

Gly Glu Phe Lys Cys Asp Pro His Glu Ala Thr Cys Tyr Asp Asp
2195             2200             2205

Gly Lys Thr Tyr His Val Gly Glu Gln Trp Gln Lys Glu Tyr Leu
2210             2215             2220

Gly Ala Ile Cys Ser Cys Thr Cys Phe Gly Gly Gln Arg Gly Trp
2225             2230             2235

Arg Cys Asp Asn Cys Arg Arg Pro Gly Gly Glu Pro Ser Pro Glu
```

```
             2240                2245                2250

Gly Thr  Thr Gly Gln Ser Tyr  Asn Gln Tyr Ser Gln  Arg Tyr His
    2255                2260                2265

Gln Arg  Thr Asn Thr Asn Val  Asn Cys Pro Ile Glu  Cys Phe Met
    2270                2275                2280

Pro Leu  Asp Val Gln Ala Asp  Arg Glu Asp Ser Arg  Glu
    2285                2290                2295

<210> SEQ ID NO 230
<211> LENGTH: 2176
<212> TYPE: PRT
<213> ORGANISM: Homo sapiens
<220> FEATURE:
<223> OTHER INFORMATION: Fibronectin 1 isoform 6

<400> SEQUENCE: 230

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
```

-continued

```
            305                 310                 315                 320
        Gln Trp Leu Lys Thr Gln Gly Asn Lys Gln Met Leu Cys Thr Cys Leu
                        325                 330                 335
        Gly Asn Gly Val Ser Cys Gln Glu Thr Ala Val Thr Gln Thr Tyr Gly
                        340                 345                 350
        Gly Asn Ser Asn Gly Glu Pro Cys Val Leu Pro Phe Thr Tyr Asn Gly
                        355                 360                 365
        Arg Thr Phe Tyr Ser Cys Thr Thr Glu Gly Arg Gln Asp Gly His Leu
            370                 375                 380
        Trp Cys Ser Thr Thr Ser Asn Tyr Glu Gln Asp Gln Lys Tyr Ser Phe
        385                 390                 395                 400
        Cys Thr Asp His Thr Val Leu Val Gln Thr Arg Gly Gly Asn Ser Asn
                        405                 410                 415
        Gly Ala Leu Cys His Phe Pro Phe Leu Tyr Asn Asn His Asn Tyr Thr
                        420                 425                 430
        Asp Cys Thr Ser Glu Gly Arg Arg Asp Asn Met Lys Trp Cys Gly Thr
                        435                 440                 445
        Thr Gln Asn Tyr Asp Ala Asp Gln Lys Phe Gly Phe Cys Pro Met Ala
            450                 455                 460
        Ala His Glu Glu Ile Cys Thr Thr Asn Glu Gly Val Met Tyr Arg Ile
        465                 470                 475                 480
        Gly Asp Gln Trp Asp Lys Gln His Asp Met Gly His Met Met Arg Cys
                        485                 490                 495
        Thr Cys Val Gly Asn Gly Arg Gly Glu Trp Thr Cys Ile Ala Tyr Ser
                        500                 505                 510
        Gln Leu Arg Asp Gln Cys Ile Val Asp Asp Ile Thr Tyr Asn Val Asn
            515                 520                 525
        Asp Thr Phe His Lys Arg His Glu Glu Gly His Met Leu Asn Cys Thr
            530                 535                 540
        Cys Phe Gly Gln Gly Arg Gly Arg Trp Lys Cys Asp Pro Val Asp Gln
        545                 550                 555                 560
        Cys Gln Asp Ser Glu Thr Gly Thr Phe Tyr Gln Ile Gly Asp Ser Trp
                        565                 570                 575
        Glu Lys Tyr Val His Gly Val Arg Tyr Gln Cys Tyr Cys Tyr Gly Arg
                        580                 585                 590
        Gly Ile Gly Glu Trp His Cys Gln Pro Leu Gln Thr Tyr Pro Ser Ser
                        595                 600                 605
        Ser Gly Pro Val Glu Val Phe Ile Thr Glu Thr Pro Ser Gln Pro Asn
            610                 615                 620
        Ser His Pro Ile Gln Trp Asn Ala Pro Gln Pro Ser His Ile Ser Lys
        625                 630                 635                 640
        Tyr Ile Leu Arg Trp Arg Pro Lys Asn Ser Val Gly Arg Trp Lys Glu
                        645                 650                 655
        Ala Thr Ile Pro Gly His Leu Asn Ser Tyr Thr Ile Lys Gly Leu Lys
                        660                 665                 670
        Pro Gly Val Val Tyr Glu Gly Gln Leu Ile Ser Ile Gln Gln Tyr Gly
                        675                 680                 685
        His Gln Glu Val Thr Arg Phe Asp Phe Thr Thr Thr Ser Thr Ser Thr
            690                 695                 700
        Pro Val Thr Ser Asn Thr Val Thr Gly Glu Thr Thr Pro Phe Ser Pro
        705                 710                 715                 720
        Leu Val Ala Thr Ser Glu Ser Val Thr Glu Ile Thr Ala Ser Ser Phe
                        725                 730                 735
```

```
Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
            755                 760                 765

Pro Ser Thr Ala Thr Ser Val Asn Ile Pro Asp Leu Leu Pro Gly Arg
770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Thr Ser Ile Val Arg Trp Ser
                820                 825                 830

Arg Pro Gln Ala Pro Ile Thr Gly Tyr Arg Ile Val Tyr Ser Pro Ser
                835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
                900                 905                 910

Leu Gln Phe Val Glu Val Thr Asp Val Lys Val Thr Ile Met Trp Thr
                915                 920                 925

Pro Pro Glu Ser Ala Val Thr Gly Tyr Arg Val Asp Val Ile Pro Val
                930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
                980                 985                 990

Gln Thr Thr Lys Leu Asp Ala Pro Thr Asn Leu Gln Phe Val Asn Glu
                995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140
```

```
Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260

Ile Pro Ala Val Pro Pro Thr Asp Leu Arg Phe Thr Asn Ile
    1265                1270                1275

Gly Pro Asp Thr Met Arg Val Thr Trp Ala Pro Pro Ser Ile
    1280                1285                1290

Asp Leu Thr Asn Phe Leu Val Arg Tyr Ser Pro Val Lys Asn Glu
    1295                1300                1305

Glu Asp Val Ala Glu Leu Ser Ile Ser Pro Ser Asp Asn Ala Val
    1310                1315                1320

Val Leu Thr Asn Leu Leu Pro Gly Thr Glu Tyr Val Val Ser Val
    1325                1330                1335

Ser Ser Val Tyr Glu Gln His Glu Ser Thr Pro Leu Arg Gly Arg
    1340                1345                1350

Gln Lys Thr Gly Leu Asp Ser Pro Thr Gly Ile Asp Phe Ser Asp
    1355                1360                1365

Ile Thr Ala Asn Ser Phe Thr Val His Trp Ile Ala Pro Arg Ala
    1370                1375                1380

Thr Ile Thr Gly Tyr Arg Ile Arg His His Pro Glu His Phe Ser
    1385                1390                1395

Gly Arg Pro Arg Glu Asp Arg Val Pro His Ser Arg Asn Ser Ile
    1400                1405                1410

Thr Leu Thr Asn Leu Thr Pro Gly Thr Glu Tyr Val Val Ser Ile
    1415                1420                1425

Val Ala Leu Asn Gly Arg Glu Glu Ser Pro Leu Leu Ile Gly Gln
    1430                1435                1440

Gln Ser Thr Val Ser Asp Val Pro Arg Asp Leu Glu Val Val Ala
    1445                1450                1455

Ala Thr Pro Thr Ser Leu Leu Ile Ser Trp Asp Ala Pro Ala Val
    1460                1465                1470

Thr Val Arg Tyr Tyr Arg Ile Thr Tyr Gly Glu Thr Gly Gly Asn
    1475                1480                1485

Ser Pro Val Gln Glu Phe Thr Val Pro Gly Ser Lys Ser Thr Ala
    1490                1495                1500

Thr Ile Ser Gly Leu Lys Pro Gly Val Asp Tyr Thr Ile Thr Val
    1505                1510                1515

Tyr Ala Val Thr Gly Arg Gly Asp Ser Pro Ala Ser Ser Lys Pro
    1520                1525                1530

Ile Ser Ile Asn Tyr Arg Thr Glu Ile Asp Lys Pro Ser Gln Met
```

-continued

```
            1535                1540                1545
Gln Val Thr Asp Val Gln Asp Asn Ser Ile Ser Val Lys Trp Leu
            1550                1555                1560
Pro Ser Ser Ser Pro Val Thr Gly Tyr Arg Val Thr Thr Thr Pro
            1565                1570                1575
Lys Asn Gly Pro Gly Pro Thr Lys Thr Lys Thr Ala Gly Pro Asp
            1580                1585                1590
Gln Thr Glu Met Thr Ile Glu Gly Leu Gln Pro Thr Val Glu Tyr
            1595                1600                1605
Val Val Ser Val Tyr Ala Gln Asn Pro Ser Gly Glu Ser Gln Pro
            1610                1615                1620
Leu Val Gln Thr Ala Val Thr Thr Ile Pro Ala Pro Thr Asp Leu
            1625                1630                1635
Lys Phe Thr Gln Val Thr Pro Thr Ser Leu Ser Ala Gln Trp Thr
            1640                1645                1650
Pro Pro Asn Val Gln Leu Thr Gly Tyr Arg Val Arg Val Thr Pro
            1655                1660                1665
Lys Glu Lys Thr Gly Pro Met Lys Glu Ile Asn Leu Ala Pro Asp
            1670                1675                1680
Ser Ser Ser Val Val Val Ser Gly Leu Met Val Ala Thr Lys Tyr
            1685                1690                1695
Glu Val Ser Val Tyr Ala Leu Lys Asp Thr Leu Thr Ser Arg Pro
            1700                1705                1710
Ala Gln Gly Val Val Thr Thr Leu Glu Asn Val Ser Pro Pro Arg
            1715                1720                1725
Arg Ala Arg Val Thr Asp Ala Thr Glu Thr Thr Ile Thr Ile Ser
            1730                1735                1740
Trp Arg Thr Lys Thr Glu Thr Ile Thr Gly Phe Gln Val Asp Ala
            1745                1750                1755
Val Pro Ala Asn Gly Gln Thr Pro Ile Gln Arg Thr Ile Lys Pro
            1760                1765                1770
Asp Val Arg Ser Tyr Thr Ile Thr Gly Leu Gln Pro Gly Thr Asp
            1775                1780                1785
Tyr Lys Ile Tyr Leu Tyr Thr Leu Asn Asp Asn Ala Arg Ser Ser
            1790                1795                1800
Pro Val Val Ile Asp Ala Ser Thr Ala Ile Asp Ala Pro Ser Asn
            1805                1810                1815
Leu Arg Phe Leu Ala Thr Thr Pro Asn Ser Leu Leu Val Ser Trp
            1820                1825                1830
Gln Pro Pro Arg Ala Arg Ile Thr Gly Tyr Ile Ile Lys Tyr Glu
            1835                1840                1845
Lys Pro Gly Ser Pro Pro Arg Glu Val Val Pro Arg Pro Arg Pro
            1850                1855                1860
Gly Val Thr Glu Ala Thr Ile Thr Gly Leu Glu Pro Gly Thr Glu
            1865                1870                1875
Tyr Thr Ile Tyr Val Ile Ala Leu Lys Asn Asn Gln Lys Ser Glu
            1880                1885                1890
Pro Leu Ile Gly Arg Lys Lys Thr Gly Gln Glu Ala Leu Ser Gln
            1895                1900                1905
Thr Thr Ile Ser Trp Ala Pro Phe Gln Asp Thr Ser Glu Tyr Ile
            1910                1915                1920
Ile Ser Cys His Pro Val Gly Thr Asp Glu Glu Pro Leu Gln Phe
            1925                1930                1935
```

Arg Val Pro Gly Thr Ser Thr Ser Ala Thr Leu Thr Gly Leu Thr
1940            1945                1950

Arg Gly Ala Thr Tyr Asn Ile Ile Val Glu Ala Leu Lys Asp Gln
1955            1960                1965

Gln Arg His Lys Val Arg Glu Val Val Thr Val Gly Asn Ser
1970            1975                1980

Val Asn Glu Gly Leu Asn Gln Pro Thr Asp Asp Ser Cys Phe Asp
1985            1990                1995

Pro Tyr Thr Val Ser His Tyr Ala Val Gly Asp Glu Trp Glu Arg
2000            2005                2010

Met Ser Glu Ser Gly Phe Lys Leu Leu Cys Gln Cys Leu Gly Phe
2015            2020                2025

Gly Ser Gly His Phe Arg Cys Asp Ser Ser Arg Trp Cys His Asp
2030            2035                2040

Asn Gly Val Asn Tyr Lys Ile Gly Glu Lys Trp Asp Arg Gln Gly
2045            2050                2055

Glu Asn Gly Gln Met Met Ser Cys Thr Cys Leu Gly Asn Gly Lys
2060            2065                2070

Gly Glu Phe Lys Cys Asp Pro His Glu Ala Thr Cys Tyr Asp Asp
2075            2080                2085

Gly Lys Thr Tyr His Val Gly Glu Gln Trp Gln Lys Glu Tyr Leu
2090            2095                2100

Gly Ala Ile Cys Ser Cys Thr Cys Phe Gly Gly Gln Arg Gly Trp
2105            2110                2115

Arg Cys Asp Asn Cys Arg Arg Pro Gly Gly Glu Pro Ser Pro Glu
2120            2125                2130

Gly Thr Thr Gly Gln Ser Tyr Asn Gln Tyr Ser Gln Arg Tyr His
2135            2140                2145

Gln Arg Thr Asn Thr Asn Val Asn Cys Pro Ile Glu Cys Phe Met
2150            2155                2160

Pro Leu Asp Val Gln Ala Asp Arg Glu Asp Ser Arg Glu
2165            2170                2175

<210> SEQ ID NO 231
<211> LENGTH: 657
<212> TYPE: PRT
<213> ORGANISM: Homo sapiens
<220> FEATURE:
<223> OTHER INFORMATION: Fibronectin 1 isoform 7

<400> SEQUENCE: 231

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
        50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

```
Glu Arg Pro Lys Asp Ser Met Ile Trp Asp Cys Thr Cys Ile Gly Ala
            115                 120                 125

Gly Arg Gly Arg Ile Ser Cys Thr Ile Ala Asn Arg Cys His Glu Gly
        130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
        290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
        370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
            405                 410                 415

Gly Ala Leu Cys His Phe Pro Phe Leu Tyr Asn Asn His Asn Tyr Thr
        420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525
```

```
Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
610                 615                 620

Ser His Pro Ile Gln Trp Asn Ala Pro Gln Pro Ser His Ile Ser Lys
625                 630                 635                 640

Tyr Ile Leu Arg Trp Arg Pro Val Ser Ile Pro Pro Arg Asn Leu Gly
                645                 650                 655

Tyr

<210> SEQ ID NO 232
<211> LENGTH: 278
<212> TYPE: PRT
<213> ORGANISM: Homo sapiens
<220> FEATURE:
<223> OTHER INFORMATION: insulin-like growth factor-binding
      protein-like 1

<400> SEQUENCE: 232

Met Pro Arg Leu Ser Leu Leu Pro Leu Leu Leu Leu Leu Leu Leu Leu
1               5                   10                  15

Pro Leu Leu Pro Pro Leu Ser Pro Ser Leu Gly Ile Arg Asp Val Gly
            20                  25                  30

Gly Arg Arg Pro Lys Cys Gly Pro Cys Arg Pro Glu Gly Cys Pro Ala
        35                  40                  45

Pro Ala Pro Cys Pro Ala Pro Gly Ile Ser Ala Leu Asp Glu Cys Gly
    50                  55                  60

Cys Cys Ala Arg Cys Leu Gly Ala Glu Gly Ala Ser Cys Gly Gly Arg
65                  70                  75                  80

Ala Gly Gly Arg Cys Gly Pro Gly Leu Val Cys Ala Ser Gln Ala Ala
                85                  90                  95

Gly Ala Ala Pro Glu Gly Thr Gly Leu Cys Val Cys Ala Gln Arg Gly
            100                 105                 110

Thr Val Cys Gly Ser Asp Gly Arg Ser Tyr Pro Ser Val Cys Ala Leu
        115                 120                 125

Arg Leu Arg Ala Arg His Thr Pro Arg Ala His Pro Gly His Leu His
130                 135                 140

Lys Ala Arg Asp Gly Pro Cys Glu Phe Ala Pro Val Val Val Val Pro
145                 150                 155                 160

Pro Arg Ser Val His Asn Val Thr Gly Ala Gln Val Gly Leu Ser Cys
                165                 170                 175

Glu Val Arg Ala Val Pro Thr Pro Val Ile Thr Trp Arg Lys Val Thr
            180                 185                 190

Lys Ser Pro Glu Gly Thr Gln Ala Leu Glu Glu Leu Pro Gly Asp His
        195                 200                 205

Val Asn Ile Ala Val Gln Val Arg Gly Gly Pro Ser Asp His Glu Ala
    210                 215                 220
```

-continued

```
Thr Ala Trp Ile Leu Ile Asn Pro Leu Arg Lys Glu Asp Glu Gly Val
225                 230                 235                 240

Tyr Gln Cys His Ala Ala Asn Met Val Gly Glu Ala Glu Ser His Ser
            245                 250                 255

Thr Val Thr Val Leu Asp Leu Ser Lys Tyr Arg Ser Phe His Phe Pro
            260                 265                 270

Ala Pro Asp Asp Arg Met
        275

<210> SEQ ID NO 233
<211> LENGTH: 848
<212> TYPE: PRT
<213> ORGANISM: Homo sapiens
<220> FEATURE:
<223> OTHER INFORMATION: NCAM1 isoform 1

<400> SEQUENCE: 233

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
290                 295                 300
```

```
Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Thr Leu Asp Gly His Met Val Val Arg Ser His Ala Arg Val Ser
        355                 360                 365

Ser Leu Thr Leu Lys Ser Ile Gln Tyr Thr Asp Ala Gly Glu Tyr Ile
    370                 375                 380

Cys Thr Ala Ser Asn Thr Ile Gly Gln Asp Ser Gln Ser Met Tyr Leu
385                 390                 395                 400

Glu Val Gln Tyr Ala Pro Lys Leu Gln Gly Pro Val Ala Val Tyr Thr
                405                 410                 415

Trp Glu Gly Asn Gln Val Asn Ile Thr Cys Glu Val Phe Ala Tyr Pro
            420                 425                 430

Ser Ala Thr Ile Ser Trp Phe Arg Asp Gly Gln Leu Leu Pro Ser Ser
        435                 440                 445

Asn Tyr Ser Asn Ile Lys Ile Tyr Asn Thr Pro Ser Ala Ser Tyr Leu
    450                 455                 460

Glu Val Thr Pro Asp Ser Glu Asn Asp Phe Gly Asn Tyr Asn Cys Thr
465                 470                 475                 480

Ala Val Asn Arg Ile Gly Gln Glu Ser Leu Glu Phe Ile Leu Val Gln
                485                 490                 495

Ala Asp Thr Pro Ser Ser Pro Ser Ile Asp Gln Val Glu Pro Tyr Ser
            500                 505                 510

Ser Thr Ala Gln Val Gln Phe Asp Glu Pro Glu Ala Thr Gly Gly Val
        515                 520                 525

Pro Ile Leu Lys Tyr Lys Ala Glu Trp Arg Ala Val Gly Glu Glu Val
    530                 535                 540

Trp His Ser Lys Trp Tyr Asp Ala Lys Glu Ala Ser Met Glu Gly Ile
545                 550                 555                 560

Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
            580                 585                 590

Phe Lys Thr Gln Pro Val Gln Gly Glu Pro Ser Ala Pro Lys Leu Glu
        595                 600                 605

Gly Gln Met Gly Glu Asp Gly Asn Ser Ile Lys Val Asn Leu Ile Lys
    610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
                645                 650                 655

Asp His Val Met Leu Lys Ser Leu Asp Trp Asn Ala Glu Tyr Glu Val
            660                 665                 670

Tyr Val Val Ala Glu Asn Gln Gln Gly Lys Ser Lys Ala Ala His Phe
        675                 680                 685

Val Phe Arg Thr Ser Ala Gln Pro Thr Ala Ile Pro Ala Asn Gly Ser
    690                 695                 700

Pro Thr Ser Gly Leu Ser Thr Gly Ala Ile Val Gly Ile Leu Ile Val
705                 710                 715                 720

Ile Phe Val Leu Leu Leu Val Val Val Asp Ile Thr Cys Tyr Phe Leu
```

```
                725                 730                 735
Asn Lys Cys Gly Leu Phe Met Cys Ile Ala Val Asn Leu Cys Gly Lys
            740                 745                 750

Ala Gly Pro Gly Ala Lys Gly Lys Asp Met Glu Glu Gly Lys Ala Ala
            755                 760                 765

Phe Ser Lys Asp Glu Ser Lys Glu Pro Ile Val Glu Val Arg Thr Glu
            770                 775                 780

Glu Glu Arg Thr Pro Asn His Asp Gly Lys His Thr Glu Pro Asn
785                 790                 795                 800

Glu Thr Thr Pro Leu Thr Glu Pro Glu Lys Gly Pro Val Glu Ala Lys
                805                 810                 815

Pro Glu Cys Gln Glu Thr Glu Thr Lys Pro Ala Pro Ala Glu Val Lys
            820                 825                 830

Thr Val Pro Asn Asp Ala Thr Gln Thr Lys Glu Asn Glu Ser Lys Ala
            835                 840                 845
```

<210> SEQ ID NO 234
<211> LENGTH: 858
<212> TYPE: PRT
<213> ORGANISM: Homo sapiens
<220> FEATURE:
<223> OTHER INFORMATION: NCAM1 isoform 2

<400> SEQUENCE: 234

```
Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
    210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
```

-continued

```
                245                 250                 255
Glu Glu Asp Asp Glu Lys Tyr Ile Phe Ser Asp Asp Ser Ser Gln Leu
                260                 265                 270
Thr Ile Lys Lys Val Asp Lys Asn Asp Glu Ala Glu Tyr Ile Cys Ile
                275                 280                 285
Ala Glu Asn Lys Ala Gly Glu Gln Asp Ala Thr Ile His Leu Lys Val
                290                 295                 300
Phe Ala Lys Pro Lys Ile Thr Tyr Val Glu Asn Gln Thr Ala Met Glu
305                 310                 315                 320
Leu Glu Glu Gln Val Thr Leu Thr Cys Glu Ala Ser Gly Asp Pro Ile
                325                 330                 335
Pro Ser Ile Thr Trp Arg Thr Ser Thr Arg Asn Ile Ser Ser Glu Glu
                340                 345                 350
Lys Ala Ser Trp Thr Arg Pro Glu Lys Gln Glu Thr Leu Asp Gly His
                355                 360                 365
Met Val Val Arg Ser His Ala Arg Val Ser Ser Leu Thr Leu Lys Ser
            370                 375                 380
Ile Gln Tyr Thr Asp Ala Gly Glu Tyr Ile Cys Thr Ala Ser Asn Thr
385                 390                 395                 400
Ile Gly Gln Asp Ser Gln Ser Met Tyr Leu Glu Val Gln Tyr Ala Pro
                405                 410                 415
Lys Leu Gln Gly Pro Val Ala Val Tyr Thr Trp Glu Gly Asn Gln Val
                420                 425                 430
Asn Ile Thr Cys Glu Val Phe Ala Tyr Pro Ser Ala Thr Ile Ser Trp
                435                 440                 445
Phe Arg Asp Gly Gln Leu Leu Pro Ser Ser Asn Tyr Ser Asn Ile Lys
            450                 455                 460
Ile Tyr Asn Thr Pro Ser Ala Ser Tyr Leu Glu Val Thr Pro Asp Ser
465                 470                 475                 480
Glu Asn Asp Phe Gly Asn Tyr Asn Cys Thr Ala Val Asn Arg Ile Gly
                485                 490                 495
Gln Glu Ser Leu Glu Phe Ile Leu Val Gln Ala Asp Thr Pro Ser Ser
                500                 505                 510
Pro Ser Ile Asp Gln Val Glu Pro Tyr Ser Ser Thr Ala Gln Val Gln
            515                 520                 525
Phe Asp Glu Pro Glu Ala Thr Gly Gly Val Pro Ile Leu Lys Tyr Lys
            530                 535                 540
Ala Glu Trp Arg Ala Val Gly Glu Glu Val Trp His Ser Lys Trp Tyr
545                 550                 555                 560
Asp Ala Lys Glu Ala Ser Met Glu Gly Ile Val Thr Ile Val Gly Leu
                565                 570                 575
Lys Pro Glu Thr Thr Tyr Ala Val Arg Leu Ala Ala Leu Asn Gly Lys
            580                 585                 590
Gly Leu Gly Glu Ile Ser Ala Ala Ser Glu Phe Lys Thr Gln Pro Val
            595                 600                 605
Gln Gly Glu Pro Ser Ala Pro Lys Leu Glu Gly Gln Met Gly Glu Asp
            610                 615                 620
Gly Asn Ser Ile Lys Val Asn Leu Ile Lys Gln Asp Asp Gly Gly Ser
625                 630                 635                 640
Pro Ile Arg His Tyr Leu Val Arg Tyr Arg Ala Leu Ser Ser Glu Trp
                645                 650                 655
Lys Pro Glu Ile Arg Leu Pro Ser Gly Ser Asp His Val Met Leu Lys
                660                 665                 670
```

-continued

```
Ser Leu Asp Trp Asn Ala Glu Tyr Glu Val Tyr Val Ala Glu Asn
    675                 680                 685

Gln Gln Gly Lys Ser Lys Ala His Phe Val Phe Arg Thr Ser Ala
690                 695                 700

Gln Pro Thr Ala Ile Pro Ala Asn Gly Ser Pro Thr Ser Gly Leu Ser
705                 710                 715                 720

Thr Gly Ala Ile Val Gly Ile Leu Ile Val Ile Phe Val Leu Leu Leu
                    725                 730                 735

Val Val Val Asp Ile Thr Cys Tyr Phe Leu Asn Lys Cys Gly Leu Phe
                740                 745                 750

Met Cys Ile Ala Val Asn Leu Cys Gly Lys Ala Gly Pro Gly Ala Lys
                755                 760                 765

Gly Lys Asp Met Glu Glu Gly Lys Ala Ala Phe Ser Lys Asp Glu Ser
770                 775                 780

Lys Glu Pro Ile Val Glu Val Arg Thr Glu Glu Glu Arg Thr Pro Asn
785                 790                 795                 800

His Asp Gly Gly Lys His Thr Glu Pro Asn Glu Thr Thr Pro Leu Thr
                    805                 810                 815

Glu Pro Glu Lys Gly Pro Val Glu Ala Lys Pro Glu Cys Gln Glu Thr
                820                 825                 830

Glu Thr Lys Pro Ala Pro Ala Glu Val Lys Thr Val Pro Asn Asp Ala
                835                 840                 845

Thr Gln Thr Lys Glu Asn Glu Ser Lys Ala
                850                 855

<210> SEQ ID NO 235
<211> LENGTH: 761
<212> TYPE: PRT
<213> ORGANISM: Homo sapiens
<220> FEATURE:
<223> OTHER INFORMATION: NCAM1 isoform 3

<400> SEQUENCE: 235

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
                20                  25                  30

Val Gly Glu Ser Lys Phe Phe Leu Cys Gln Val Ala Gly Asp Ala Lys
            35                  40                  45

Asp Lys Asp Ile Ser Trp Phe Ser Pro Asn Gly Glu Lys Leu Thr Pro
        50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175
```

```
Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
        210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
        290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Thr Leu Asp Gly His Met Val Val Arg Ser His Ala Arg Val Ser
        355                 360                 365

Ser Leu Thr Leu Lys Ser Ile Gln Tyr Thr Asp Ala Gly Glu Tyr Ile
        370                 375                 380

Cys Thr Ala Ser Asn Thr Ile Gly Gln Asp Ser Gln Ser Met Tyr Leu
385                 390                 395                 400

Glu Val Gln Tyr Ala Pro Lys Leu Gln Gly Pro Val Ala Val Tyr Thr
                405                 410                 415

Trp Glu Gly Asn Gln Val Asn Ile Thr Cys Glu Val Phe Ala Tyr Pro
            420                 425                 430

Ser Ala Thr Ile Ser Trp Phe Arg Asp Gly Gln Leu Leu Pro Ser Ser
        435                 440                 445

Asn Tyr Ser Asn Ile Lys Ile Tyr Asn Thr Pro Ser Ala Ser Tyr Leu
        450                 455                 460

Glu Val Thr Pro Asp Ser Glu Asn Asp Phe Gly Asn Tyr Asn Cys Thr
465                 470                 475                 480

Ala Val Asn Arg Ile Gly Gln Glu Ser Leu Glu Phe Ile Leu Val Gln
                485                 490                 495

Ala Asp Thr Pro Ser Ser Pro Ser Ile Asp Gln Val Glu Pro Tyr Ser
            500                 505                 510

Ser Thr Ala Gln Val Gln Phe Asp Glu Pro Glu Ala Thr Gly Gly Val
        515                 520                 525

Pro Ile Leu Lys Tyr Lys Ala Glu Trp Arg Ala Val Gly Glu Glu Val
        530                 535                 540

Trp His Ser Lys Trp Tyr Asp Ala Lys Glu Ala Ser Met Glu Gly Ile
545                 550                 555                 560

Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
            580                 585                 590
```

```
Phe Lys Thr Gln Pro Val His Ser Pro Pro Pro Pro Ala Ser Ala Ser
    595                 600                 605

Ser Ser Thr Pro Val Pro Leu Ser Pro Pro Asp Thr Thr Trp Pro Leu
    610                 615                 620

Pro Ala Leu Ala Thr Thr Glu Pro Ala Lys Gly Glu Pro Ser Ala Pro
625                 630                 635                 640

Lys Leu Glu Gly Gln Met Gly Glu Asp Gly Asn Ser Ile Lys Val Asn
                645                 650                 655

Leu Ile Lys Gln Asp Asp Gly Gly Ser Pro Ile Arg His Tyr Leu Val
            660                 665                 670

Arg Tyr Arg Ala Leu Ser Ser Glu Trp Lys Pro Glu Ile Arg Leu Pro
        675                 680                 685

Ser Gly Ser Asp His Val Met Leu Lys Ser Leu Asp Trp Asn Ala Glu
    690                 695                 700

Tyr Glu Val Tyr Val Val Ala Glu Asn Gln Gln Gly Lys Ser Lys Ala
705             710                 715                 720

Ala His Phe Val Phe Arg Thr Ser Ala Gln Pro Thr Ala Ile Pro Ala
                725                 730                 735

Thr Leu Gly Gly Asn Ser Ala Ser Tyr Thr Phe Val Ser Leu Leu Phe
            740                 745                 750

Ser Ala Val Thr Leu Leu Leu Cys
        755                 760
```

LUNG CANCER DIFFERENTIAL MARKER

CROSS REFERENCE TO RELATED APPLICATIONS

This application is a divisional of U.S. application Ser. No. 13/823,922, filed Mar. 15, 2013, now U.S. Pat. No. 9,696,320, which is a national stage application filed under 35 USC § 371 of PCT/JP2011/070635, filed Sep. 9, 2011, which claims the benefit of Japanese Patent Application No. 2010-209932, filed Sep. 17, 2010, each of which is incorporated by reference herein in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 119244_00124_Sequence_Listing. The size of the text file is 206 KB, and the text file was created on Jun. 2, 2017.

FIELD OF THE INVENTION

The present invention relates to a lung cancer differential marker glycoprotein having a glycan or a fragment thereof, and a method for determining the presence or absence of lung cancer or the histological type of lung cancer using the same.

BACKGROUND OF THE INVENTION

Lung cancer is a typical example of intractable cancers and is the first and second leading causes of cancer deaths in Japanese men and women, respectively, in 2009. The types of lung cancer are broadly classified into small cell cancer (small cell lung cancer) accounting for approximately 10% and non-small cell cancer accounting for approximately 90%. The types of non-small cell cancer are further classified into adenocarcinoma (lung adenocarcinoma) (60%), squamous cell carcinoma (lung squamous cell carcinoma) (25%), and large-cell cancer (large-cell lung cancer) (5%).

The small cell lung cancer is a very high-grade cancer and therefore has a strong tendency to metastasize even in an early stage. As seen in previous cases, it is likely that the small cell lung cancer has already metastasized systemically when found. Thus, non-surgical therapy is commonly selected for this cancer even if its metastasis to lymph nodes or other tissues is not confirmed. Since this cancer is highly sensitive to chemotherapy or radiation, chemotherapy is central to the non-surgical therapy.

By contrast, the non-small cell lung cancer, which constitutes a large portion of lung cancer cases, is low sensitive to chemotherapy or radiation. For its treatment, it is important to find the cancer relatively early and remove the lesion by surgical therapy.

Tests for lung cancer can be broadly classified, depending on the purposes of the tests, into three: (1) lung cancer assessment to test the probability of lung cancer; (2) definite diagnosis of lung cancer to confirm that this probable lung cancer is definitely lung cancer; and (3) determination of the stage of lung cancer progression to test the histological type and stage of progression of the definitely diagnosed lung cancer.

These tests generally adopt a method which involves detecting an abnormal shadow in the lung field by chest X-ray examination or CT scan and subsequently finally determining a cancer type and comprehensively determining the stage of progression by bronchoscopy or by the pathological diagnosis of biopsy samples obtained using biopsy or the like. However, cases with small cell cancer coexisting with non-small cell cancer or borderline cancers might be given different diagnostic outcomes among pathologists. Accurate definite diagnosis has not yet been established for lung cancer.

In recent years, tumor markers have been used in cancer prognosis or the like. The tumor markers refer to substances produced by cancer cells or substances produced by cells in response to cancer cells. The amounts of the tumor markers contained in serum reflect the amount or histological type of tumor. The tumor markers can therefore serve as an index for, for example, determining the presence or absence of cancer and as such, can be used in diagnostic aids, the prediction of a histological type or the stage of progression, the determination of therapeutic effects, the prediction of recurrence, prognosis, etc. Currently, some tumor markers, such as CEA, CYFRA, NSE, ProGRP, SCC, and SLX, are also known for lung cancer (Non Patent Literatures 1 to 3). All of these tumor markers, however, are based on the difference in protein expression level, i.e., increase or decrease in protein expression, in blood or tissue between healthy persons and lung cancer patients. These tumor markers are usually expressed even in normal cells and are thus low specific for lung cancer. Hence, the obtained results present the problem of low reliability or detection sensitivity. In addition, lung cancer markers useful in determining the histological type of detected lung cancer have not yet been found.

CITATION LIST

Non Patent Literature

Non Patent Literature 1: Molina R, et al., (2005) Anticancer Res 25: 1773-1778.
Non Patent Literature 2: Mizuguchi S, et al., (2007) Ann Thorac Surg 83: 216-221.
Non Patent Literature 3: Holdenrieder S, et al., (2008) Clin Cancer Res 14: 7813-7821.

SUMMARY OF THE INVENTION

Technical Problem

An object of the present invention is to develop a lung cancer differential marker with which lung cancer can be diagnosed conveniently and highly sensitively without depending only on increase or decrease in protein expression level between cancer patients and healthy persons. More specifically, an object of the present invention is to develop a lung cancer-specific differential marker glycoprotein and a fragment thereof, which serve as an indication for suffering lung cancer.

Another object of the present invention is to develop a lung cancer differential marker capable of determining the histological type of lung cancer.

A further object of the present invention is to develop a glycan probe for differential diagnosis of lung cancer, with which the presence or absence of lung cancer and further, its histological type can be determined by histological staining.

Solution to Problem

The compositional and structural diversities of glycans on proteins secreted from cells are controlled by the balanced expression of hundreds of glycan-related genes and vary depending on the degrees of cell differentiation and cancer progression. Glycoproteins whose glycan structures are altered can be used as disease condition index markers including tumor markers. In recent years, such glycan-related tumor markers based on proteomics have been searched for actively. In the pipeline of the marker search, first, candidate molecules are identified by large-scale analysis at phase 1. Subsequently, the candidate molecules are tested by quantitative analysis at phase 2 to narrow down the candidates. Then, a validation test is conducted at phase 3.

In order to attain the objects, the present inventors have searched for lung cancer differential markers using glycoproteomics based on the marker search pipeline. As a result, the present inventors have successfully identified, from among serum glycoproteins, novel glycoprotein or glycopeptide groups having lung cancer-specific structures detected in a lung cancer cell culture supernatant. The present inventors have also revealed that the presence or absence of lung cancer and the histological type of lung cancer can be determined using these glycoprotein or glycopeptide groups. The present invention is based on these findings and provides the followings:

(1) A lung cancer differential marker glycoprotein listed in Table 1 or 2, being glycosylated with a glycan at the asparagine residue(s) at the glycosylation site(s) shown in Table 1 or 2:

TABLE 1

| Protein # | Protein name | gi(ID) | Small cell cancer AAL | Small cell cancer ConA | Adeno-carcinoma AAL | Adeno-carcinoma ConA | Glycosylation site | Peptide sequence | SEQ ID NO: |
|---|---|---|---|---|---|---|---|---|---|
| 1 | acid alpha-glucosidase | gi\|119393591, gi\|119393893 | ○ | X | X | X | 390<br>470<br>882 | QVVENMTR<br>GVFITNETGQPLIGK<br>GAYTQVIFLARNNTIVNELVR | 1<br>2<br>3 |
| 2 | biotinidase | gi\|4557373 | X | X | ○ | X | 119<br>150<br>349<br>349 | DVQIIVPEDGIHGFNFTR<br>FNDTEVLQR<br>SHLIIAQVAKNPVGLIGAENATGETDPSHSK<br>NPVGLIGAENATGETDPSHSKFLK | 4<br>5<br>6<br>7 |
| 3 | cathepsin D | gi\|4503143 | X | X | ○ | ○ | 263 | YYKGSLSYLNVTR | 8 |
| 4 | cathepsin L1 | gi\|22202619, gi\|4503155 | ○ | X | X | X | 221<br>221 | YNPKYSVANDTGFVDIPKQEK<br>YSVANDTGFVDIPK | 9<br>10 |
| 5 | cathepsin L2 | gi\|23110960 | ○ | X | X | X | 221<br>292 | YRPENSVANDTGFTVAPGKEK<br>NLDHGVLVVGYGFEGANSNNSK | 11<br>12 |
| 6 | cell adhesion molecule 4 | gi\|21686977 | ○ | X | X | X | 67 | QTLFFNGTR | 13 |
| 7 | deoxyribonuclease II, lysosomal | gi\|4503349 | ○ | X | X | X | 86 | SNTSQLAFLLYNDQPPQPSK | 14 |
| 8 | fibronectin 1 | gi\|47132557 (isoform 1),<br>gi\|47132551 (isoform 2),<br>gi\|16933542 (isoform 3),<br>gi\|47132555 (isoform 4),<br>gi\|47132553 (isoform 5),<br>gi\|47132549 (isoform 6),<br>gi\|47132547 (isoform 7) | X | X | ○ | X | 430<br>528<br>542<br>542<br>1007<br>1007<br>1291 | GGNSNGALCHFPFLYNNHNYTDCSEGR<br>DQCIVDDITYNVNDTFHL<br>RHEEGHMLNCTCFGQGR<br>HEEGHMLNCTCFGQGR<br>ESKPLTAQQTTKLDAPTNLQFVNETDSTVLVR<br>LDAPTNLQFVNETDSTVLVR<br>WTPLNSSTIIGYR | 15<br>16<br>17<br>18<br>19<br>20<br>21 |
| 9 | galectin-3-binding protein-like | gi\|122937327 | ○ | X | X | X | 44<br>61<br>307 | ADVGGEAAGTSINHSQAVLQR<br>QGNASDVVLR<br>FFDVNGSAFLPR | 22<br>23<br>24 |
| 10 | insulin-like growth factor 2 receptor | gi\|119964726 | ○ | X | X | X | 112<br>435<br>582<br>2085 | SLLEFNTTVSCDQQGTNHR<br>MSVINFECNKTAGNDGK<br>TNITLVCKPGDLESAPVLR<br>GYPCGGNKTASSVIELTCTK | 25<br>26<br>27<br>28 |
| 11 | insulin-like growth factor binding protein 3 | gi\|62243248 (isoform a),<br>gi\|62243068 (isoform b) | X | X | ○ | X | 116<br>205 | GLCVNASAVSR<br>YKDYESQSTDTQNFSSESKR | 29<br>30 |

TABLE 1-continued

| Protein # | Protein name | gi(ID) | Small cell cancer AAL | Small cell cancer ConA | Adeno-carcinoma AAL | Adeno-carcinoma ConA | Glycosylation site | Peptide sequence | SEQ ID NO: |
|---|---|---|---|---|---|---|---|---|---|
| 12 | insulin-like growth factor binding protein-like 1 | gi\|56090548 | X | ○ | X | X | 166<br>166 | DGPCEFAPVVVPPRSVHNVTGAQVGLSCEVR<br>SVHNVTGAQVGLSCEVR | 31<br>32 |
| 13 | integral membrane protein 1 | gi\|22749415 | X | ○ | X | X | 548 | TILVDNNTWNNTHISR | 33 |
| 14 | L1 cell adhesion molecule | gi\|4557707 (isoform 1),<br>gi\|13435353 (isoform 2) | X | X | X | ○ | 433<br>671<br>777<br>979 | ILTADNQTYMAVQGSTAYLLCK<br>WYSLGKVPGNQTSTTLK<br>VQWRPQGTRGPWQEQIVSDPFLVVSNTSTFVPYEIK<br>THNLTDLSPHLR | 34<br>35<br>36<br>37 |
| 15 | lysosomal acid phosphatase | gi\|4557010 | ○ | ○ | X | X | 133<br>167<br>177 | FNPNISWQPIPVHTVPITEDR<br>YEQLQNETRQTPEYQNESSR<br>QTPEYQNESSR | 38<br>39<br>40 |
| 16 | melanoma cell adhesion molecule | gi\|71274107 | ○ | X | X | X | 56<br>418 | CGLSQSQNLSHVDWFSVHK<br>CVACVPSIPGLNR | 41<br>42 |
| 17 | melanoma-associated antigen p97 | gi\|13424428\|<br>gi\|16163666 | ○ | ○ | X | X | 38<br>515 | WCATSDPEQHKCGNMSEAFR<br>DCDVLTAVSEFNASCVPNNPK | 43<br>44 |
| 18 | neoginen homolog 1 | gi\|4505375 | X | ○ | X | X | 73<br>210<br>470 | GSSVILNCSAYSEPSPK<br>VIKLPSGMLVISNATEGDGGLYR<br>TPASDPHGDNLTYSVFYTK | 45<br>46<br>47 |
| 19 | neural cell adhesion molecule 1 | gi\|94420689 (isoform 1),<br>gi\|115529482 (isoform 2),<br>gi\|115529478 (isoform 3) | ○ | X | X | X | 347<br>449<br>478 | TSTRNISSEEK<br>DGQLLPSSNYSNIK<br>IYNTPSASYLEVTPDSENDFGNYNCTAVNR | 48<br>49<br>50 |
| 20 | neuronal pentraxin II | gi\|28195384 | ○ | X | X | X | 148<br>189 | ANVSNAGLPGDFR<br>VAELEDEKSLLHNETSAHR | 51<br>52 |
| 21 | neuronal pentraxin receptor | gi\|17402888 | X | ○ | X | X | 42 | ALPGGADNASVASGAAASPGPQR | 53 |
| 22 | ribonuclease T2 | gi\|5231228 | X | X | ○ | X | 106<br>212 | AYWPDVIHSFPNR<br>QDQQLQNCTEPGEQPSPK | 54<br>55 |
| 23 | secretogranin III | gi\|19557645 | ○ | ○ | X | X | 68<br>346 | KTYPPENKPGQSNYSFVDNLLLK<br>NKLEKNATDNISK | 56<br>57 |
| 24 | sel-1 suppressor of lin-12-like | gi\|19923669 | X | ○ | X | X | 608 | EASIVGENETYPR | 58 |

TABLE 1-continued

| Protein # | Protein name | gi(ID) | Small cell cancer AAL | Small cell cancer ConA | Adeno-carcinoma AAL | Adeno-carcinoma ConA | Glycosylation site | Peptide sequence | SEQ ID NO: |
|---|---|---|---|---|---|---|---|---|---|
| 25 | sparc/osteonectin, cwcv and kazal-like domains proteoglycan (testican) 2 | gi|7662036 | ○ | ○ | X | X | 225<br>225 | LRDWFQLLHENSKQNGSASSVAGPASGLDK<br>QNGSASSVAGPASGLDK | 59<br>60 |
| 26 | Thy-1 cell surface antigen | gi|19923362 | ○ | ○ | X | X | 42 | LDCRHENTSSSPIQYEFSLTR | 61 |
| 27 | tubulointerstitial nephritis antigen-like 1 | gi|11545918 | X | X | X | ○ | 78<br>161 | GRADDCALPYLGAICYCDLFCNR<br>AINQGNYGWQAGNHSAFWGMTLDEGIR | 62<br>63 |
| 28 | v-kit Hardy-Zuckerman 4 feline sarcoma viral oncogene homolog | gi|4557695 (isoform 1),<br>gi|148005039 (isoform 2) | ○ | ○ | X | X | 130<br>367<br>463<br>486 | SLYGKEDNDTLVR<br>TFTDKWEDYPKSENESNIR<br>CSASVLPVDVQTLNSSGPPFGK<br>LVVQSSIDSSAFKHNGTVECK | 64<br>65<br>66<br>67 |
| 29 | laminin alpha 5 | gi|21264602 | X | X | ○ | ○ | 95<br>921<br>1330<br>1529<br>2019<br>2196<br>2209<br>2303<br>2423<br>2501<br>2568<br>2707<br>3107<br>3287 | LVGGPVAGGDPNQTIR<br>LNLTSPDLFWLVFR<br>VMQGHANASFCPHGYGCR<br>TIPPDCLLCQPQTFGCHPLVGCEECNCSGPIQELTD PTCDTDSGQCK<br>CEICAPGFYGNALLPGNCTR<br>GINASSMAWAR<br>LHRLNASIADLQSQLR<br>TLSELMSQTGHLGLANASAPSGEQLLR<br>DNATLQATLHAAR<br>LVEAAEAHAQQIGQLALNLSSIILDVNQDRLTQR<br>QGLVDRAQQLLANSTALEEAMLQEQQR<br>GVHNASLALSASIGR<br>LNTTGVSAGCTADLLVGR<br>VFDLQQNLGSVNVSTGCAPALQAQTPGLGPR | 68<br>69<br>70<br>71<br>72<br>73<br>74<br>75<br>76<br>77<br>78<br>79<br>80<br>81 |
| 30 | laminin, beta 1 | gi|450495 | X | X | ○ | ○ | 1041<br>1279<br>1487<br>1643 | KCVCNYLGTVQEHCNGSDCQCDK<br>LSDTTSQSNSTAK<br>QSAEDILLTNATK<br>AIKQADEDIQGTQNLLTSIESETAASETLFNASQR | 82<br>83<br>84<br>85 |
| 31 | phospholipid transfer protein | gi|5453914 (isoform a),<br>gi|33356541 (isoform b) | X | X | ○ | ○ | 64<br>143<br>143<br>245<br>398<br>193 | GKEGHFYYNISEVK<br>MKVSNVSCQASVSR<br>VSNVSCQASVSR<br>GAFFPLTERNWSLPNR<br>FRIYSNHSALESLALIPLQAPLK<br>GAFFPLTERNWSLPNR | 86<br>87<br>88<br>89<br>90<br>91 |

TABLE 2

| Protein # | Protein name | gi (ID) | Small cell cancer AAL | Small cell cancer ConA | Adeno-carcinoma AAL | Adeno-carcinoma ConA | Glycosylation site | Peptide sequence | SEQ ID NO: |
|---|---|---|---|---|---|---|---|---|---|
| 1 | activated leukocyte cell adhesion molecule | gi\|68163411 | X | ○ | X | X | 167<br>265<br>265<br>361<br>480 | KLGDCISEDSYPDGNITWYR<br>NAIKEGDNITLK<br>EGDNITLK<br>NATVVWMKDNIR<br>YYSKIIISPEENVTLTVTAENQLER | 92<br>93<br>94<br>95<br>96 |
| 2 | alpha 2 type V collagen preproprotein | gi\|89363017 | X | | X | ○ | 1400 | EASQNITICK | 97 |
| 3 | amiloride binding protein 1 | gi\|73486661 | X | X | X | ○ | 538 | LENITNPWSPR | 98 |
| 4 | aspartate beta-hydroxylase | gi\|14589866 (isoform a) | X | X | X | ○ | 452 | LVQLFNDTSLKNDLGVGYLLIGDNDNAKK | 99 |
| 5 | aspartate beta-hydroxylase | gi\|14589864 (isoform b) | ○ | ○ | X | X | 64 | DFRYNLSEVLQGK | 100 |
| 6 | beta-1,2-galactosyl-O-glycosyl-glycoprotein beta-1,6-N-acetylglucosaminyltransferase | gi\|148277029,<br>gi\|148277031,<br>gi\|148277033,<br>gi\|148277035,<br>gi\|21614523 | X | X | X | ○ | 58<br>95 | HLELAGENPSSDINCTK<br>WTPDDYINMTSDCSSFIK | 101<br>102 |
| 7 | bone morphogenetic protein 1 | gi\|4502421 | X | X | X | ○ | 142<br>363<br>599 | AATSRPERVWPDGVIPFVIGGNFTGSQR<br>ISVTPGEKIILNFTSLDLYR<br>LNGSITSPGWPK | 103<br>104<br>105 |
| 8 | calsyntenin 2 | gi\|11545861 | ○ | X | X | X | 98<br>374<br>716<br>729 | IHGQELPFEAVVLNKTSGEGR<br>NLTDQFTITMWMK<br>QECLELNHSELHQR<br>HLDATNSTAGYSIYGVGSMSR | 106<br>107<br>108<br>109 |
| 9 | carboxypeptidase D | gi\|22202611 | X | ○ | X | X | 172<br>522<br>975<br>1070 | LLNTTDVYLLPSLNPDGFERAR<br>RFANEYPNITR<br>HIWSLEISNKPNVSEPEEPKIR<br>GKDLDTDFTNNASQPETK | 110<br>111<br>112<br>113 |
| 10 | CD47 Antigen | gi\|4502673 (isoform 1),<br>gi\|38683836 (isoform 2),<br>gi\|68223315 (isoform 3) | X | ○ | X | X | 73<br>73<br>111 | GRDITFDGALNK<br>DIYTFDGALNKSTVPTDFSSAK<br>MDKSDAVSHTGNYTCEVTELTR | 114<br>115<br>116 |
| 11 | CD63 antigen | gi\|4502679 (isoform A),<br>gi\|91199546 (isoform B) | X | ○ | X | X | 130<br>130<br>172 | QQMENYOKNNHTASILDR<br>NNHTASILDR<br>NRVPDSCCINVTVGCGINFNEK | 117<br>118<br>119 |

TABLE 2 -continued

| Protein # | Protein name | gi(ID) | Small cell cancer AAL | Small cell cancer ConA | Adeno-carcinoma AAL | Adeno-carcinoma ConA | Glycosylation site | Peptide sequence | SEQ ID NO: |
|---|---|---|---|---|---|---|---|---|---|
| 12 | CD97 antigen | gi\|17978491 (isoform 1), gi\|17978489 (isoform 2), gi\|68508955 (isoform 3) | X | X | | X | 108 453 360 108 404 | TFKNESENTCQDVDECQQNPR RLSAVNSIFLSHNNTK RLSAVNSIFLSHNNTK TFKNESENTCQDVDECQQNPR RLSAVNSIFLSHNNTK | 120 121 122 123 124 |
| 13 | complement factor I | gi\|119392081 | X | X | ○ | X | 103 177 177 464 494 | FLNNGTCTAEGK FKLSDLSINSTECLHVHCR LSDLSINSTECLHVHCR SIPACVPWSPYLFQPNDTCIVSGWGR LISNCSKFYGNR | 125 126 127 128 129 |
| 14 | cystatin F | gi\|20302139 | X | X | ○ | | 84 84 137 | YSVEKFNNCTNDMFLFK FNNCTNDMFLFKESR LDDCDFQTNHTLK | 130 131 132 |
| 15 | desmocollin 2 | gi\|13435364 | X | X | X | ○ | 546 629 | SLDREAETIKNGIYNITVLASDQGGR AINDTAAR | 133 134 |
| 16 | epithelial V-like antigen 1 | gi\|21536337 | X | X | X | ○ | 39 118 | VLEAVNGTAR LQFDDNGTYTCQVK | 135 136 |
| 17 | FAT tumor suppressor 1 | gi\|66346693 | X | X | ○ | ○ | 333 998 1551 3716 | AIGGIDWDSHPFGYNLTLQAK QVYNLTVR IVVNVSDTNDHAPWFTASSYK QLLHKINSSVTDIEBIIGVR | 137 138 139 140 |
| 18 | fibrinogen-like2 | gi\|5730075 | X | X | ○ | ○ | 263 336 | LDGSTNFTR LHVGNYNGTAGDALR | 141 142 |
| 19 | Fraser syndrome 1 | gi\|108773804 | X | X | ○ | ○ | 1107 1503 1776 2562 2667 | IHTPSLHVNGSLILPIGSIKPLDFSLLNVQDQEGR IVYNITLPLHPNQGIIEHR ISGSEVEELSEVSNFTMEDINNKK YTSYNVSEK VIINDTEDEPTLEFDKK | 143 144 145 146 147 |
| 20 | growth differentiation factor 15 | gi\|4758936 | X | X | X | ○ | 70 70 | LRANQSWEDSNTDLVPAPAVR ANQWEDSNTDLVPAPAVRILTPEVR | 148 149 |
| 21 | immunoglobin superfamily, member 4D isoform 1 | gi\|148664190 (isoform 1), gi\|148664211 (isoform 2) | ○ | X | X | X | 101 113 | FQLLNFSSSELK VSLTNVSISDEGR | 150 151 |
| 22 | integrin, alpha 1 | gi\|31657142 | X | X | X | ○ | 418 883 1113 | NTTFNVESTK DSCESNHNITCK SENASLVLSSSNQK | 152 153 154 |

TABLE 2 -continued

| Protein # | Protein name | gi(ID) | Small cell cancer AAL | Small cell cancer ConA | Adeno-carcinoma AAL | Adeno-carcinoma ConA | Glycosylation site | Peptide sequence | SEQ ID NO: |
|---|---|---|---|---|---|---|---|---|---|
| 23 | intercellular adhesion molecule 1 | gi\|4557878 | X | X | X | X | 202<br>267 | TELDLPQGLELFENTSAPYQLQTFVLPATPPQLVSPR<br>LNPTVYGNDSFSAK | 155<br>156 |
| 24 | interleukin 6 receptor | gi\|4504673 | X | X | O | X | 93 | SVQLHDSGNYSCYR | 157 |
| 25 | latent transforming growth factor beta binding protein 3 | gi\|18497288 | X | X | O | X | 89<br>349<br>845 | DSCQQGSNMTLIGENGHSTDTLTGSGFR<br>RLNSTHCQDINECAMPGVCR<br>DRSHCDIDECDFPAACIGGDCINTNGSYR | 158<br>159<br>160 |
| 26 | mucin 16 | gi\|83367077 | X | X | O | X | 12586<br>13193<br>14363<br>14417 | NTSVGLLYSGCR<br>KFNITRSVLQGLLKPLFK<br>NIEDALNQLFRNSSIK<br>NGTQLQNFTLDR | 161<br>162<br>163<br>164 |
| 27 | netrin 4 | gi\|93204871 | X | X | O | X | 56<br>163 | KLWADTTCGQNATELYCFYSENTDLTCRQPK<br>YFATNCSATFGLEDDVVKK | 165<br>166 |
| 28 | neuronal cell adhesion molecule isoform A | gi\|81158226 | X | O | X | X | 223<br>245, 254<br>276<br>314<br>507<br>858 | FNHTQTIQQK<br>VISVDELNDTIAANLSDTEFYGAK<br>ERPPTFLTPEGNASNKEELR<br>EDGMLPKNR<br>GSALHEDIYVLHENGTLEIPVAQKDSTGTYTCVAR<br>VNVVNSTLAEVHWDPVPLK | 167<br>168<br>169<br>170<br>171<br>172 |
| 29 | olfactomedin related ER localized protein | gi\|17136143 (isoform 1),<br>gi\|5453547 (isoform 2) | O | O | X | X | 85<br>85<br>270<br>376<br>85 | QLLEKVQNMSQSIEVLDRR<br>VQNMSQSIEVLDRR<br>SMVDFMNTDNFTSHR<br>LDPVSLQTLQTWNTSYPKR<br>QLLEKVQNMSQSIEVLDR | 173<br>174<br>175<br>176<br>177 |
| 30 | osteoprotegerin | gi\|148743793 | X | X | O | X | 98<br>152<br>178<br>289 | ELQYVKQECNR<br>CPDGFFSNETSSKAPCR<br>GNATHDNICSGNSESTQK<br>HIGHANLTFELQR | 178<br>179<br>180<br>181 |
| 31 | palmitoyl-protein thioesterase 1 (ceroid-lipofuscinosis, neuronal 1, infantile) | gi\|4506031 | X | X | X | O | 212<br>232 | GINESYKK<br>FLNDSIVDPVDSEWFGFYR | 182<br>183 |
| 32 | peptidylprolyl isomerase B | gi\|4758950 | X | X | X | O | 148 | HYGPGWVSMANAGKDTNGSQFFITTVK | 184 |

TABLE 2 -continued

| Protein # | Protein name | gi (ID) | Small cell cancer AAL | Small cell cancer ConA | Adeno-carcinoma AAL | Adeno-carcinoma ConA | Glycosylation site | Peptide sequence | SEQ ID NO: |
|---|---|---|---|---|---|---|---|---|---|
| 33 | plasminogen activator, tissue type I | gi\|4505861 | X | X | X | ○ | 152, 219, 219, 483 | GTWSTAEGAECTNWNSSALAQKPYSGR<br>AGKYSEFCSTPACSEGNSDCFGNGSAYR<br>YSSEFCSTPACSEGNSDCYFGNGSAYR<br>CTSQHLNRTVTDNMLCAGDTR | 185<br>186<br>187<br>188 |
| 34 | prion protein | gi\|122056623,<br>gi\|122056625,<br>gi\|122056628, | X | X | X | ○ | 197, 197 | QHTVTTTKGENFTETDVK<br>GENFTETDVK | 189<br>190 |
| 35 | proslaglandin H2 D-isomerase | gi\|32171249 | X | X | X | ○ | 51, 78 | WFSAGLASNSSWLR<br>SVVAPATDGGLNLTSTFLR | 191<br>192 |
| 36 | protein tyrosine phosphatase, receptor type, F | gi\|109633041 (isoform 1),<br>gi\|109633039 (isoform 2), | ○<br> | X<br> | X<br> | X<br> | 721<br>966<br>721<br>957 | KVEVEPLNSTAVHVYWK<br>DINSQELQNITTDTRFTLTGLKPDTTYDIK<br>KVEVEPLNSTAVHVYWK<br>DINSQELQNITTDTRFTLTGLKPDTTYDIK | 193<br>194<br>195<br>196 |
| 37 | protein tyrosine phosphatase, receptor type, U | gi\|110735404 (isoform 1),<br>gi\|110735406 (isoform 2),<br>gi\|110735402 (isoform 3) | X | X | ○ | X | 410 | QLTLQWEPLGYNVTR | 197 |
| 38 | seizure related 6 homolog (mouse)-like 2 | gi\|6912612 (isoform 1),<br>gi\|42491358 (isoform 2) | ○ | ○ | X | X | 177<br>303<br>247<br>373 | LLANSMLGEGQVLR<br>IVSPEPGGAVGPNLTCR<br>LLANSMLGEGQVLR<br>IVSPEPGGAVGPNLTCR | 198<br>199<br>200<br>201 |
| 39 | seizure related 6 homolog (mouse)-like | gi\|32261332 | ○ | X | X | X | 328 | SVNLSDGELLSIR | 202 |
| 40 | seizure related 6 homolog | gi\|148839280 (isoform 1),<br>gi\|148839346 (isoform 2) | X | ○ | X | X | 399, 422<br>436, 440 | HLTCLNATQPFWDSKEPVCIAACGGVIRNATTGR<br>IVSPGFPGNYSNNLTCHWLLEAPEGQR | 203<br>204 |
| 41 | serine carboxypeptidase vitellogenic-like | gi\|83641874,<br>gi\|83641876 | ○ | ○ | X | X | 346 | QAIHVGNQTFNDGTIVEK | 205 |
| 42 | solute carrier family 39 (zinc transporter), member 10 | gi\|55741750 | X | X | X | ○ | 191, 198<br>218<br>339 | LHHHLDHNTHHFHNDSITPSER<br>GEPSNEPSTETNKTQEQSDVKLPK<br>KDLNEDDHHHECLNVTQLLK | 206<br>207<br>208 |

TABLE 2 -continued

| Protein # | Protein name | gi (ID) | Small cell cancer AAL | Small cell cancer ConA | Adeno-carcinoma Glycosylation AAL | Adeno-carcinoma Glycosylation ConA | site | Peptide sequence | SEQ ID NO: |
|---|---|---|---|---|---|---|---|---|---|
| 43 | tenascin C (hexabrachion) | gi\|4504549 | X | X | ○ | X | 38 | QSGVNATLPEENQPVVFNHVYNIK | 209 |
| | | | | | | | 327 | CINGTCYCEEGFTGEDCGKPTCPHACHTQGR | 210 |
| | | | | | | | 788 | QTGLAPGQEYEISLHIVKNNTRGPGLK | 211 |
| | | | | | | | 1018 | LNYSLPTGQWVGVQLPR | 212 |
| | | | | | | | 1034 | NTTSVVLRGLEPGQEYNVLLTAEK | 213 |
| | | | | | | | 1079 | VKASTEQAPELENLTVTEVGWDGLR | 214 |
| | | | | | | | 1093 | LNWTAADQAYEHFIIQVQEANKEAAR | 215 |
| | | | | | | | 1485 | LLETVEYNISGAER | 216 |
| 44 | tissue factor pathway inhibitor | gi\|5454114 | X | X | ○ | X | 145 | YFYNNQTK | 217 |
| 45 | transforming growth factor, beta 1 | gi\|63025222 | X | X | ○ | ○ | 82 | LRLASPPSQGEVPPGPLP EAVLALYNSTR | 218 |
| 46 | tumor-associated calcium signal transducer 1 | gi\|4505059, gi\|4505057 | X | X | ○ | X | 111 | QCNGTSTCWCVNTAGVR | 219 |
| | | | | | | | 168 | HRPTAGAFNHSDLDAELR | 220 |
| 47 | UDP-GlcNac:betaGal beta-1,3-N-acetylglocusaminyl-transferase 2 | gi\|9845238 | X | X | ○ | X | 89 | LSNISHLNYCEPDLR | 221 |
| | | | | | | | 173 | ESWGQESNAGNQTVVR | 222 |
| 48 | von Willebrand factor A domain containing 2 | gi\|33348304 | X | X | ○ | ○ | 147 | NASVPQILIIVTDGK | 223 |

(2) The lung cancer differential marker glycoprotein according to (1), wherein the sugar chain is at least one glycan selected from the group consisting of a fucosylated glycan, a high mannose-type glycan, a hybrid-type glycan, a biantennary complex-type glycan, chitin, polylactosamine, and a (β1,3-galactose epitope.

(3) The lung cancer differential marker glycoprotein according to (2), wherein the glycoprotein is for differential diagnosis of small cell lung cancer or lung adenocarcinoma.

(4) The lung cancer differential marker glycoprotein according to (3), wherein the glycoprotein is for differential diagnosis of small cell lung cancer and is at least one glycoprotein selected from the group consisting of neural cell adhesion molecule (NCAM1), secretogranin III, and insulin-like growth factor-binding protein-L1 (IGFBP-L1).

(5) The lung cancer differential marker glycoprotein according to (3). wherein the glycoprotein is for differential diagnosis of lung adenocarcinoma and is fibronectin 1.

(6) A fragment of a lung cancer differential marker glycoprotein according to any of (1) to (5), comprising at least one asparagine residue at a glycosylation site shown in Table 1 or 2 being glycosylated with a glycan.

(7) A method for determining lung cancer, comprising detecting at least one lung cancer differential marker glycoprotein shown in Table 1 or 2 being glycosylated with a glycan at the asparagine residue(s) at the glycosylation site(s) shown in Table 1 or 2, and/or at least one fragment thereof, the fragment comprising at least one asparagine residue at the glycosylation site shown in Table 1 or 2 being glycosylated with a glycan, from a sample obtained from a test subject, wherein the detection of the glycoprotein or fragment determines that the test subject suffers lung cancer.

(8) The method according to (7), wherein the lung cancer differential marker glycoprotein and/or the fragment thereof are detected using at least one glycan probe binding to the glycan.

(9) The method according to (8), wherein the glycan probe binds to a fucosylated glycan, a high mannose-type glycan, a hybrid-type glycan, a biantennary complex-type glycan, chitin, polylactosamine, or a β1,3-galactose epitope.

(10) The method according to (8) or (9), wherein the glycan probe is a lectin, an antibody, or a phage antibody.

(11) The method according to (10), wherein the lectin is AAL, ConA, PWM, or PNA.

(12) The method according to (11), wherein the lung cancer differential marker glycoprotein is neural cell adhesion molecule (NCAM1), and the detection of the binding thereof to AAL determines the histological type of the lung cancer as small cell cancer.

(13) The method according to (11), wherein the lung cancer differential marker glycoprotein is secretogranin III, and the detection of the binding thereof to AAL and/or ConA determines the histological type of the lung cancer as small cell cancer.

(14) The method according to (11), wherein the lung cancer differential marker glycoprotein is insulin-like growth factor-binding protein-L1 (IGFBP-L1), and the detection of the binding thereof to ConA and/or PWM determines the histological type of the lung cancer as small cell cancer.

(15) The method according to (11), wherein the lung cancer differential marker glycoprotein is fibronectin 1, and the detection of the binding thereof to AAL and/or PNA determines the histological type of the lung cancer as adenocarcinoma.

(16) The method according to any of (8) to (11). wherein the histological type of lung cancer is determined as small cell cancer or adenocarcinoma on the basis of a result of binding of the glycan probe to the glycan in the lung cancer differential marker glycoprotein and/or the fragment thereof, and a manner of binding of the lung cancer differential marker glycoprotein shown in Table 1 or 2 and/or the fragment thereof to the glycan probe.

(17) The method according to any of (7) to (16), wherein the sample is a body fluid, a cell, or a lung lavage.

(18) The method according to (17), wherein the body fluid is blood (including serum, plasma, and interstitial fluid), lymph, a cell extract, sputum, or pleural effusion.

(19) A lung cancer cell-identifying antibody for histological staining, binding to a lung cancer differential marker glycoprotein listed in Table 1 or 2 being glycosylated with a glycan at the asparagine residue(s) at the glycosylation site(s) shown in Table 1 or 2, and/or a fragment thereof, the fragment comprising at least one asparagine residue at a glycosylation site shown in Table 1 or 2 being glycosylated with a glycan, and thereby diagnosing lung cancer.

(20) The antibody according to (19), wherein the antibody is capable of determining a histological type of a lung cancer cell.

(21) The antibody according to (20), wherein the lung cancer differential marker glycoprotein is neuronal pentraxin receptor (NPR), and the histological type of the lung cancer cell is determined as small cell cancer.

The present specification encompasses the contents described in the specification and/or drawings of Japanese Patent Application No. 2010-209932 on which the priority of the present application is based.

Advantageous Effects of Invention

According to the lung cancer differential marker of the present invention, the presence or absence of lung cancer can be determined conveniently and highly reliably by the testing of a body fluid, a cell, or a lung lavage. According to the lung cancer differential marker of the present invention, the histological type of lung cancer can be further determined.

The method of the present invention can determine the presence or absence of lung cancer and the histological type of lung cancer using a body fluid, a cell, or a lung lavage with a more highly proper differential rate and lower invasiveness than existing tumor markers.

According to the glycan probe for differential diagnosis of lung cancer of the present invention, the presence or absence of lung cancer and further, its histological type can be determined by histological staining.

DETAILED DESCRIPTION OF THE INVENTION

Figure 1:
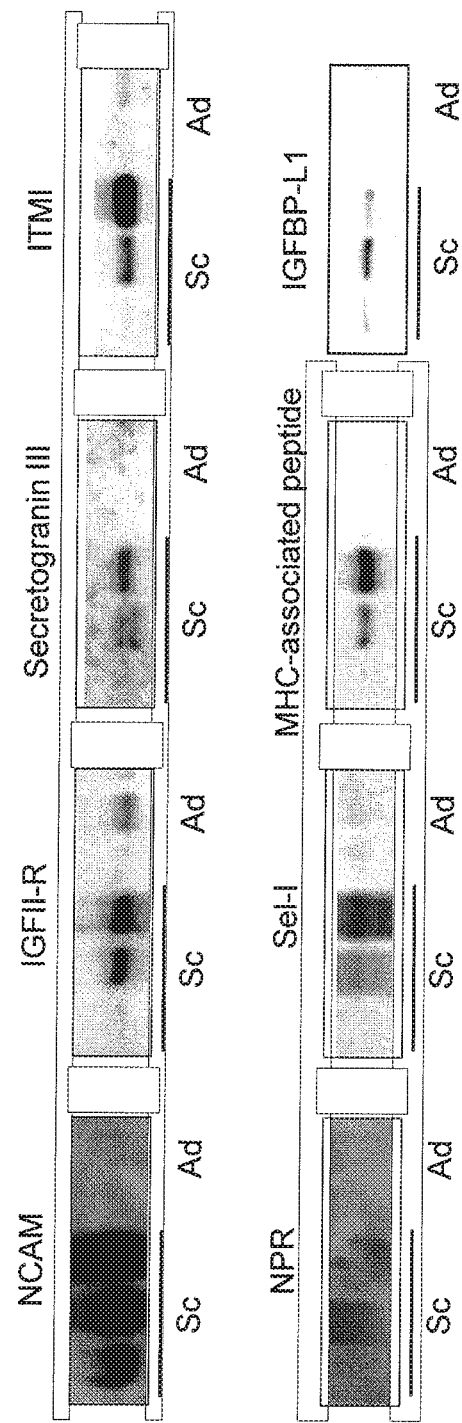
FIG. 1 is a Western blot image showing the expression of small cell lung cancer differential marker glycoproteins in the culture supernatants of cultured small cell lung cancer cells (Sc) and cultured lung adenocarcinoma cells (Ad).

1. Lung Cancer Differential Marker Glycoprotein and Fragment Thereof

The first embodiment of the present invention provides lung cancer differential marker glycoproteins shown in Table 1 or 2 above and fragment thereof.

1-1. Lung Cancer Differential Marker Glycoprotein

The "lung cancer differential marker glycoprotein" of this embodiment corresponds to a protein represented by each of Protein #1 to #31 in Table 1 and Protein #1 to #48 in Table 2. All of these proteins are lung cancer-specific glycoproteins comprising, in their amino acid sequences, a glycosylated asparagine residue at least at a position (counted from the initiating amino acid residue as the first position) represented by "Glycosylation site" in each table. In the case of, for example, acid alpha-glucosidase represented by Protein #1 in Table 1, glycans are linked to asparagine residues at least at positions 390, 470, and 882 in the amino acid sequence of this protein. Hereinafter, in the present specification, such a glycosylated protein is referred to as a "glycoprotein".

In each table, "gi(ID)" represents the ID number of each glycoprotein of this embodiment. A plurality of gi(ID) numbers registered for one protein are all described in the table. Also, a plurality of isoforms of one protein are indicated by isoform numbers together with their gi(ID) numbers in the table.

The glycan linked to the asparagine residue is not particularly limited as long as the glycan is linked in a lung cancer-specific manner. Examples thereof include fucosylated glycans, high mannose-type glycans, hybrid-type glycans, biantennary complex-type glycans, chitin, polylactosamine, and β1,3-galactose epitopes. In this context, the "glycan linked in a lung cancer-specific manner" refers to a glycan linked to the asparagine residue represented by "Glycosylation site" in the table, only in the lung cancer cell-derived protein. Hence, as a rule, the lung cancer differential marker glycoprotein of this embodiment is a glycoprotein produced from a lung cancer cell. Thus, the detection of presence or absence of the glycoprotein, for example, in the serum of a test subject, using a glycan probe recognizing this glycoprotein can determine an individual having the glycoprotein as suffering lung cancer.

In the present specification, the "glycan probe" refers to a determinant that specifically recognizes a particular glycan and/or glycoconjugate such as a glycoprotein and binds thereto. Examples thereof include lectins, antibodies, and phage antibodies.

As described above, the histological types of "lung cancer" are known to consist of: small cell cancer; and non-small cell cancer further including adenocarcinoma, squamous cell carcinoma, and large cell cancer. Neuroendocrine cancer in the lung is also known. Most of the neuroendocrine cancer types are classified into small cell cancer, whereas the other histological types of this cancer are also known. The lung cancer differential marker glycoprotein of this embodiment can determine the histological type of lung cancer, depending on the type of the glycan linked to the prescribed asparagine residue. In the case of, for example, acid alpha-glucosidase represented by Protein #1 in Table 1, fucosylated glycans are linked to the prescribed asparagine residues only in a small cell lung cancer-derived glycoprotein. Thus, use of a lectin or an antibody that can bind to and recognize any of the fucosylated glycans can diagnose lung cancer with acid alpha-glucosidase as a lung cancer differential marker glycoprotein. In this case, the acid alpha-glucosidase can also serve as a marker that confirms the lung cancer as small cell cancer. Alternatively, in the case of biotinidase represented by Protein #2 in Table 1, fucosylated glycans are linked to the prescribed asparagine residues only in a lung adenocarcinoma-derived glycoprotein. Thus. use of a lectin or an antibody that can bind to and recognize any of the fucosylated glycans can diagnose lung cancer with biotinidase as a lung cancer differential marker glycoprotein. In this case, the biotinidase can also serve as a marker that confirms the lung cancer as adenocarcinoma.

The fucosylated glycan can be detected using AAL lectin. The high mannose-type glycan, the hybrid-type glycan, and the biantennary complex-type glycan can be detected using ConA lectin. The chitin and the polylactosamine can be detected using PWM lectin. The β1,3-galactose epitope can be detected using PNA lectin. In Table 1, the presence and absence of the binding between each lung cancer differential marker glycoprotein and AAL lectin or ConA lectin are indicated by "◯" and "x", respectively. Taking acid alpha-glucosidase represented by Protein #1 as an example, only a small cell lung cancer-derived glycoprotein has fucosylated glycans at the prescribed asparagine residues and is thus indicated by "○" in "AAL" of "Small cell cancer" and by "x" in the other boxes. The same holds true for the other lung cancer differential marker glycoproteins in Tables 1 and 2. Accordingly, each lung cancer differential marker glycoprotein (including a fragment of the lung cancer differential marker glycoprotein) shown in Tables 1 and 2 can serve as a marker for differentiation of small cell lung cancer or lung adenocarcinoma based on the manner of its binding to AAL lectin and ConA lectin for "small cell cancer" and "adenocarcinoma" in Tables 1 and 2.

1-2. Fragment of Lung Cancer Differential Marker Glycoprotein

The "lung cancer differential marker glycoprotein fragment" or the "fragment of the lung cancer differential marker glycoprotein" of this embodiment refers to an oligopeptide or polypeptide fragment consisting of a portion of the lung cancer differential marker glycoprotein. This fragment comprises, in its amino acid sequence, at least one asparagine residue at the glycosylation site shown in Table 1 or 2, wherein the lung cancer-specific glycan described in the paragraph "1-1. Lung cancer differential marker glycoprotein" is linked to this asparagine residue.

The amino acid length of the lung cancer differential marker glycoprotein fragment is not particularly limited and is preferably 5 to 100 amino acids, 8 to 80 amino acids, or 8 to 50 amino acids. Hereinafter, in the present specification, the lung cancer differential marker glycoprotein fragment is also referred to as a "glycoprotein fragment" or a "glycopeptide". Hereinafter, the lung cancer differential marker glycoprotein and its glycoprotein fragment are also collectively referred to as a "lung cancer differential marker".

Specific examples of the lung cancer differential marker glycoprotein fragment include glycopeptides consisting of amino acid sequences represented by SEQ ID NOs: 1 to 223 shown in Tables 1 and 2. These are glycoprotein fragments that were obtained by an IGOT method (described later) in identifying the lung cancer differential marker glycoproteins of this embodiment. Any of these glycoprotein fragments can be used as a lung cancer differential marker, as in the lung cancer differential marker glycoproteins, to determine the presence or absence of lung cancer and determine the histological type of the detected lung cancer, depending on the type of glycan linked to the prescribed asparagine residue. In each amino acid sequence shown in Tables 1 and 2, the underlined asparagine residue (N) represents a glycan-linked asparagine residue.

1-3. Obtainment of Lung Cancer Diagnosis Marker Glycoprotein

Methods by which the lung cancer differential marker glycoprotein fragments and the lung cancer differential marker glycoproteins of this embodiment were obtained and identified will be described below.

1-3-1. Large-Scale Identification of Lung Cancer-Specific Candidate Glycoprotein The large-scale selective collection and concentration of the lung cancer-specific glycoproteins can adopt any of methods broadly classified into, for example, a method using probes having affinity for glycans, a method using chemical reaction with glycans (Zhang H. et al., Nat Biotechnol 21, 660-666 (2003)), and a method of introducing affinity tags to glycans. Here, the method using probes, which were used in the obtainment of the lung cancer differential marker glycoproteins in Tables 1 and 2, will be described.

First, lectins or anti-glycan antibodies reactive with glycans characteristically produced by cancer cells are selected as probes.

The probe lectins can be selected by the statistical analysis of glycan profiles using a lectin microarray. Alternatively, the probe lectins may be selected in consideration of literature information (some probe lectins to be used can be expected on the basis of, for example, increased fucosylation associated with malignant transformation) or the resulting determination performance of the histological type. Basically, lectins are selected by the statistical analysis of profile, and the selected lectins are validated on the basis of binding specificity. In the case of targeting lung cancer, for example, *Aleuria aurantia*-derived AAL lectin capable of detecting fucosylation, *Canavalia ensiformis*-derived ConA lectin capable of detecting high mannose-type, hybrid-type, or biantennary complex-type glycans, *Phytolacca americana*-derived PWM lectin capable of detecting chitin or polylactosamine, and/or *Arachis hypogaea*-derived PNA lectin capable of detecting Pβ1,3-galactose epitopes can be used.

The antibody probes or phage antibody probes may be prepared after structural determination of antigens (glycans). This is not a necessary condition, and these probes can also be prepared against the unknown structures of the antigenic glycans or glycopeptides.

For the large-scale identification of candidate glycoproteins, specifically, candidate glycoproteins are first collected from the culture supernatant of a lung cancer-derived cell line in a medium using the glycan probes (probe lectins and/or antibody probes or phage antibody probes). Use of the lung cancer-derived cell culture supernatant enables cancer cell-derived glycoproteins to be identified and can thus facilitate the detection of difference from glycans present on the serum-derived glycoproteins of healthy persons. This information can be useful in selectively obtaining candidate molecules from serum. The cells used may be derived from any histological type of lung cancer, i.e., small cell cancer or non-small cell cancer (adenocarcinoma, squamous cell carcinoma, or large cell cancer). Candidate glycoproteins may be collected from each histological type, and the results can be analyzed by comparison to obtain histological type-nonspecific lung cancer differential markers or histological type-specific lung cancer differential markers.

1-3-2. Identification of Glycopeptide by IGOT Method

The collected lung cancer differential marker candidate glycoproteins are then treated by a method based on an isotope-coded glycosylation site-specific tagging (IGOT) method and mass spectrometry to identify core glycopeptides in the candidate glycoproteins. The glycopeptides can be analyzed by a Lec-IGOT-LC/MS method described in, for example, JP Patent Publication (Kokai) No. 2004-233303 A (2004) (JP Patent No. 4220257) and Kaji H, et al., Mass spectrometric identification of N-linked glycopeptides using lectin-mediated affinity capture and glycosylation site-specific stable isotope tagging. Nature Protocols 1, 3019-3027 (2006). An example of the specific method will be described below.

(1) Glycan Cleavage and IGOT Method

The candidate glycoprotein groups collected with the probe lectins or the probe antibodies are digested with protease. From the obtained peptide groups, candidate glycopeptide groups are sampled and re-collected using the same probes as above. Alternatively, crude sample protein mixtures may be digested with protease without separating candidate glycoprotein groups from the crude sample protein mixtures, and candidate glycopeptide groups can be collected directly from the obtained crude peptide groups using the probe lectins or the probe antibodies. Subsequently, the obtained candidate glycopeptides are labeled by the IGOT method. The IGOT method involves dissociating glycans from the glycopeptides by treatment with enzymes such as glycopeptidase in oxygen isotope-labeled water, while causing the conversion of glycosylated asparagine to aspartic acid, during which the oxygen isotope ($^{18}O$) in the water is incorporated into the candidate glycopeptides.

(2) LC/MS Shotgun Analysis of Labeled Peptide

The candidate glycopeptides labeled by the IGOT method are separated by liquid column chromatography (LC) and applied to mass spectrometry (MS). Their amino acid sequences are exhaustively identified by tandem mass spectrometry.

(3) Identification of Candidate Glycopeptide

According to, for example, an MS/MS ion search method described in the Standard Technology Collection (edited by the Japan Patent Office), Mass spectrometry, 3-6-2-2 Amino acid sequence analysis, a database can be searched by comparing the respective MS/MS peptide measurement results of the obtained candidate glycopeptides with the hypothetical MS/MS spectra of all peptides predicted according to the specificity of the protease actually used from the amino acid sequences of all proteins registered in the database. In this search, the following amino acid modifications are taken into consideration: oxidation of methionine residue side chain, pyroglutamic acid conversion (deamination or cyclization) of ammo-terminal glutamine, deamination of an amino terminus (carbamidomethylation of cysteine), deamidation of asparagine residue side chain (provided that the stable isotope oxygen is already incorporated therein). The candidate glycoproteins including the candidate glycopeptide are identified using search software Mascot.

(4) Identification of Glycosylation Site

Of the candidate glycopeptides identified by the MS/MS ion search method, each candidate glycopeptide that has an asparagine residue with deamidated (stable isotope-incorporated) side chain and contains an N-linked glycosylation consensus sequence (Asn-Xaa-[Ser/Thr], provided that Xaa is not Pro) is regarded as the glycoprotein fragment of this embodiment. Also, the asparagine residue in the consensus sequence of the obtained glycoprotein fragment is defined as the glycosylation site. When Xaa is Lys/Arg and the identified peptide sequence is cleaved at this site, the candidate glycopeptide in which a residue subsequent to Xaa is [Ser/Thr] with reference to the amino acid sequence of the whole protein thereof is also included in the glycoprotein fragment. As a rule, the glycosylation site is contained in the consensus sequence, although some reports suggest different glycosylation sites. In this specification, a glycosylation site cleaved with peptide-N-glycanase (glycopeptidase F, PNGase) can be identified.

The lung cancer differential marker glycoprotein fragment groups selected by the method described above and the lung cancer differential marker glycoproteins (comprising these fragments) identified on the basis of their amino acid sequences are defined as the glycoprotein fragment groups and the glycoproteins shown in Tables 1 and 2.

The glycoprotein fragment groups and the glycoproteins can serve as lung cancer differential markers for diagnosing lung cancer in a test subject, for example, by testing the presence or absence thereof in the serum of the test subject using lectins or antibodies recognizing them.

1-3-3. Validation of Lung Cancer Differential Marker

The significance of the lung cancer differential markers selected in the paragraph 1-3-2 can be further validated. For example, from among the glycoproteins and/or the glycoprotein fragments collected with the probe lectins from the lung cancer cell culture supernatant, significant lung cancer differential markers can be detected and confirmed by Western blot or immunoprecipitation using antibodies specifically recognizing the lung cancer differential markers separated and identified above. In the present specification, 31 lung cancer differential marker glycoproteins shown in Table 1 and fragments of the glycoproteins correspond to the lung cancer differential markers further selected by the detection with the antibodies.

Figure 5:
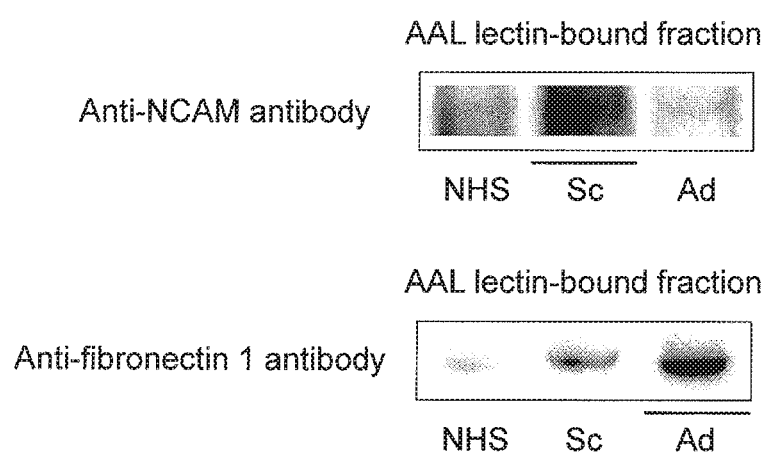
FIG. 5 is a Western blot image in which lung cancer differential marker glycoproteins (NCAM and fibronectin 1) in the sera of small cell lung cancer patients (Sc) and lung adenocarcinoma patients (Ad) fractionated with AAL lectin were detected with their respective anti-lung cancer differential marker glycoprotein antibodies
Figure 6:
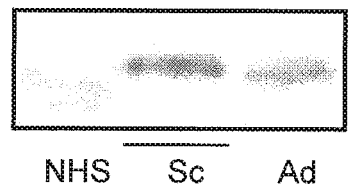
FIG. 6 is a Western blot image in which a lung cancer differential marker glycoprotein (secretogranin III) in the sera of small cell lung cancer patients (Sc) and lung adenocarcinoma patients (Ad) fractionated by the serial chromatography of the sera was detected with an antibody (anti-secretogranin III antibody).
Figure 8:
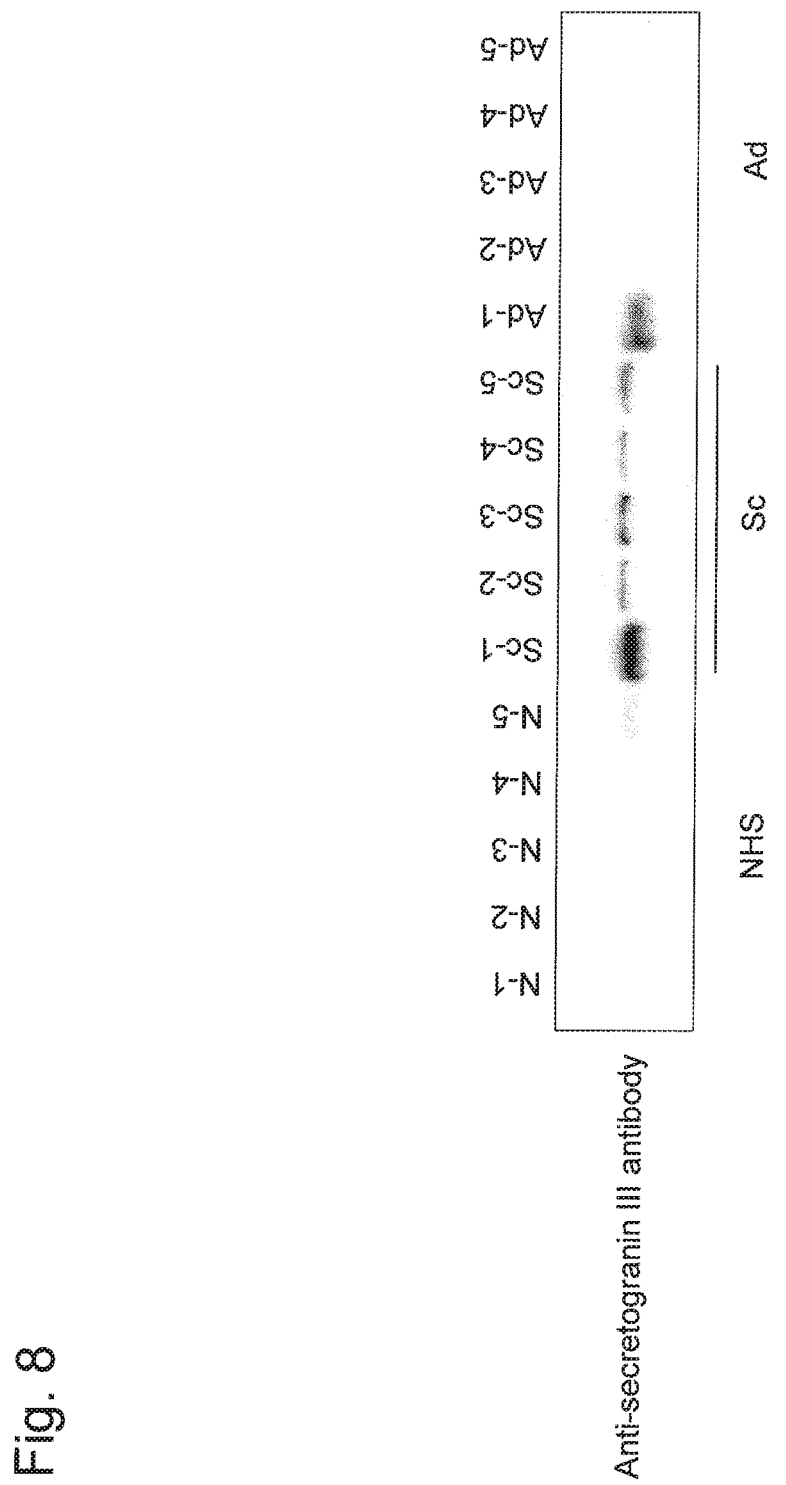
FIG. 8 is a Western blot image in which a lung cancer differential marker glycoprotein (secretogranin III) in the sera of small cell lung cancer patients (Sc) and lung adenocarcinoma patients (Ad) fractionated by the multisample serial chromatography of the sera was detected with an antibody (anti-secretogranin III antibody).
Figure 9:
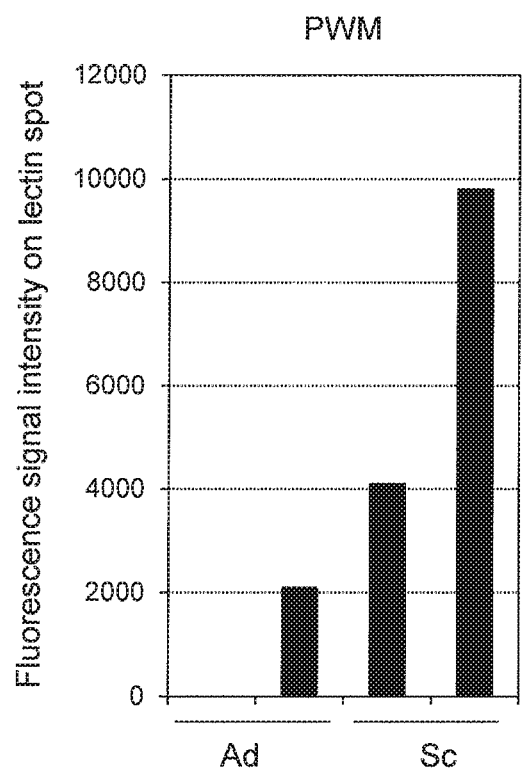
FIG. 9 is a diagram showing the comparison of fluorescence signal intensities on PWM lectin spots, from a lung cancer differential marker glycoprotein (insulin-like growth factor-binding protein-L1), in an antibody-overlay lectin array using eluates purified using an antibody (anti-insulin-like growth factor-binding protein-L1 antibody) from the culture supernatants of cultured small cell lung cancer cells (Sc) and cultured lung adenocarcinoma cells (Ad).
Figure 10:
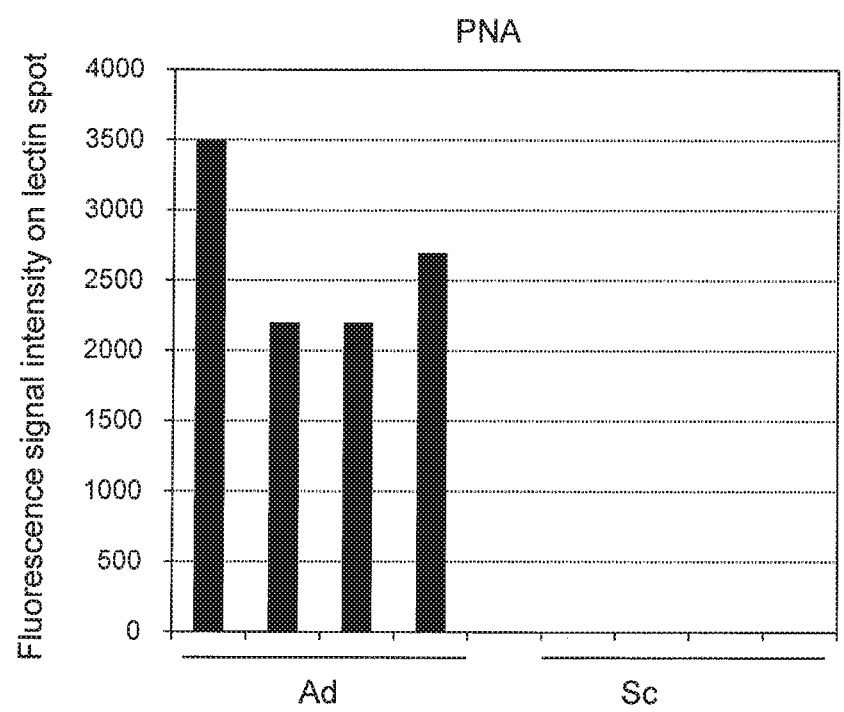
FIG. 10 is a diagram showing the comparison of fluorescence signal intensities on PNA lectin spots, from a lung cancer differential marker glycoprotein (fibronectin 1), in an antibody-overlay lectin array using eluates purified using an antibody (anti-fibronectin 1 antibody) from the culture supernatants of cultured small cell lung cancer cells (Sc) and cultured lung adenocarcinoma cells (Ad).

Also, the lung cancer differential markers further selected by the detection with the antibodies may be further validated. For example, lung cancer differential markers are collected using the probe lectins from the sera of lung cancer patients, and significant markers can be further detected using the specific antibodies. As an example, neural cell adhesion molecule (NCAM1) (represented by Protein #19 in Table 1) and fibronectin 1 (represented by Protein #8 in Table 1) shown in FIG. 5, and secretogranin III (represented by Protein #23 in Table 1) shown in FIGS. 6 and 8 correspond to the lung cancer differential marker glycoproteins confirmed to be useful by this further validation. In this context, the neural cell adhesion molecule binds to AAL lectin only in small cell lung cancer as shown in Table 1 and can thus serve as a lung cancer differential marker that allows differential diagnosis of small cell lung cancer. Likewise, the secretogranin III binds to AAL lectin and ConA lectin only in small cell lung cancer as shown in Table 1 and can thus serve as a lung cancer differential marker that allows differential diagnosis of small cell lung cancer. By contrast, the fibronectin 1 binds to AAL lectin only in lung adenocarcinoma as shown in Table 1 and can thus serve as a lung cancer differential marker that allows differential diagnosis of lung adenocarcinoma. Alternatively, for example, lung cancer differential markers may be collected from the culture supernatant of a lung cancer cell line using specific antibodies, and useful markers can be detected using a lectin array. As an example, insulin-like growth factor-binding protein-L1 (IGFBP-L1) (represented by Protein #12 in Table 1) shown in FIG. 9 and fibronectin 1 (represented by Protein #8 in Table 1) shown in FIG. 10 correspond to the lung cancer differential marker glycoproteins confirmed to be useful by the further validation. In this context, the insulin-like growth factor-binding protein-L1 (1GFBP-L1) produces a strong detectable fluorescence signal on a PWM lectin spot in small cell lung cancer as shown in FIG. 9 and can thus serve as a lung cancer differential marker that allows differential diagnosis of small cell lung cancer. By contrast, the fibronectin 1 produces a detectable fluorescence signal on a PNA lectin spot only in lung adenocarcinoma as shown in FIG. 10 and can thus serve as a lung cancer differential marker that allows differential diagnosis of lung adenocarcinoma.

1-4. Detection of Lung Cancer Differential Marker Glycopeptide and Glycoprotein 1-4-1. Mass Spectrometry The lung cancer differential marker glycopeptides and glycoproteins can be detected with a mass spectrometer as a detector from samples collected with the probe lectins or the like binding to glycans.

The collected lung cancer differential marker glycopeptides can be detected, preferably, by the cleavage of their glycans followed by liquid chromatography (LC) to separate and elute peptides, which are then introduced in order directly to a mass spectrometer (MS) on line. The mass spectrometry is not only available for obtaining mass spectra, but also available for obtaining MS/MS spectra using a fragmentation method such as collision-induced dissociation (CID) and further detect a plurality of fragment ions generated by CID or the like only when pre-selected ions are detected (this approach is also called single reaction monitoring or multiple reaction monitoring). Furthermore, analyte peptides differing in mass by the incorporation of stable isotopes into some of synthesized core peptide moieties of lung cancer differential marker glycopeptides may be added to analysis samples, and their respective signal intensities can be compared to thereby achieve relative or absolute quantitative analysis. More simply, the signal intensity of the detected ion may be compared between two or more samples or with that of a reference sample to achieve simplified quantification.

The lung cancer differential marker glycoproteins can be detected using various proteomics approaches known in the art. For example, the collected proteins can be separated by one-dimensional or two-dimensional gel electrophoresis and quantified by the comparison of signal intensities (dye, fluorescence, etc.) between the target spot and a reference sample. In the case of a detection method using a mass spectrometer, the collected protein groups are digested with protease, and the formed peptides can be detected by LC/MS analysis. For such quantification, various methods based on stable isotope labeling (ICAT, MCAT, iTRAQ, SILAC, etc.) can be used in combination with a non-labeled simple quantification method (peptide counting method, area integration method, etc.). As further described later, the glycoproteins may be quantified by ELISA.

1-4-2. Lectin Microarray (1) Glycan Profiling Using Lectin Microarray (a) Lectin Microarray (Also Simply Referred to as a Lectin Array)

The lectin array refers to a substrate on which plural types of lectins differing in specificity are immobilized in parallel (i.e., in the form of array) as glycan probes. The lectin array allows concurrent analysis on the types of lectins interacted with analyte glycoconjugates and the degrees of these interactions. By use of this lectin array, information required for estimating glycan structures can be obtained by single analysis, while the steps from sample preparation to scanning can be carried out quickly and conveniently. In a glycan profiling system such as mass spectrometry, glycoproteins cannot be analyzed directly and must thus be decomposed into glycopeptides or free glycans in advance. In the lectin microarray, advantageously, glycoproteins can be analyzed directly by merely introducing, for example, fluorescent materials directly into the core protein moieties thereof. The lectin microarray technique has been developed by the present inventors, and the fundamental principles of this technique are described in, for example, Kuno A., et al. Nat. Methods 2, 851-856 (2005).

Typical examples of the lectins used in the lectin array include those described in the following Table 3:
Table 3
1Sugar Binding Specificity For example, a lectin array comprising 45 types of lectins (including the 43 types of lectins described above) immobilized on a substrate is already commercially available under the product name of LecChip from GP Biosciences Ltd.

(2) Statistical Analysis of Glycan Profiles Using Lectin Array

The lectin array has already evolved into a practical technique by which a quantitative comparative glycan profiling can be realized not only for purified preparations but also for mixed samples such as serum or cell lysates. Particularly, the comparative glycan profiling of cell surface glycans has achieved remarkable development (Ebe, Y et al. J. Biochem. 139, 323-327 (2006); Pilobello, K. T. et al. Proc Natl Acad Sci USA. 104, 11534-11539 (2007); and Tateno, H. et al. Glycobiology 17, 1138-1146 (2007)).

Also, data mining by the statistical analysis of glycan profiles can be carried out by a method shown in, for example, "Kuno A, et al. J Proteomics Bioinform. 1, 68-72 (2008)" or "the Japanese Society of Carbohydrate Research 2008/8/18, Development of Application Technique for Lectin Microarray—Comparative Glycan Profiling and Statistical Analysis of Biological Sample-, Atsushi Kuno, Atsushi Matsuda, Yoko Itakura, Hideki Matsuzaki, Hisashi Narimatsu. Jun Hirabayashi" and "Matsuda A, et al. Biochem Biophys Res Commun. 370, 259-263 (2008)".

(3) Antibody-Overlay Lectin Microarray Method

The platform of the lectin microarray in this method is basically the same as above. For detection, the sample of the test subject is not directly labeled with a fluorescent material or the like but is indirectly labeled by the introduction of a fluorescent group or the like into the sample of the test subject via an antibody. This application method can realize concurrent multisample analysis more conveniently and quickly (see "Kuno A, Kato Y, Matsuda A, Kaneko M K, Ito H, Amano K, Chiba Y, Narimatsu H, Hirabayashi, J. Mol Cell Proteomics. 8, 99-108 (2009)", "Jun Hirabayashi, Atsushi Kuno, Noboru Uchiyama, "Development of Application Technology for Glycan Profiling Using Lectin Microarray", Experimental Medicine, extra number "Study on Cancer Diagnosis at Molecular Level—Challenge to Clinical Application", Yodosha Co., Ltd., Vol. 25 (17) 164-171 (2007)", Atsushi Kuno, Jun Hirabayashi, "Application of Glycan Profiling System Based On Lectin Microarray to Glycan Biomarker Search", and Genetic Medicine MOOK No. 11 "Development of Clinical Glycan Biomarker and Elucidation of Glycan Function", pp. 34-39, Medical Do, Inc. (2008)).

For example, glycan moieties in glycoprotein samples obtained from a test subject are recognized by lectins on the lectin microarray. Thus, antibodies against the core protein moieties thereof can be overlaid on the glycoproteins to thereby specifically and highly sensitively detect the glycoproteins without labeling the test glycoproteins or highly purifying them.

(4) Lectin-Overlay Antibody Microarray Method

This method employs, instead of the lectin microarray, an antibody microarray in which antibodies against core proteins are immobilized in parallel (i.e., in the form of array) on a substrate such as a glass substrate. This method requires the same numbers of antibodies as the number of markers to be examined and also requires determining lectins in advance for detecting the alteration of glycans.

1-4-3 Lectin-Antibody Sandwich Immunological Detection

A simple and inexpensive sandwich detection method can be designed on the basis of the results obtained using the lectin array. Basically, this method can adopt the protocol of the sandwich detection method using two types of antibodies except that one of the antibodies is replaced by lectins. Thus, this approach is also applicable to automatization using an existing automatic immunodetection apparatus. The point to be noted is only the reaction between antibodies and lectins to be used for sandwiching antigens. Each antibody has at least two N-linked glycans. When the lectins used recognize glycans on the antibodies, background noise inevitably occurs during sandwich detection due to the binding reaction therebetween. A possible approach for preventing the generation of this noise signal involves modifying the glycan moieties on the antibodies or using only Fab fragments, which contain no such glycan moieties. These approaches have already been known in the art. For the method of modifying the glycan moieties, for example, Chen S. et al., Nat Methods. 4, 437-44 (2007) and Comunale M A, et al., J Proteome Res. 8, 595-602 (2009) can be referred to. For the method using Fab fragments, for example, Matsumoto H., et al., Clin Chem Lab Med 48, 505-512 (2010) can be referred to.

1-4-4. Method Using Serial Chromatography

The antibody-overlay lectin array is the best approach for statistically finding lectins that most precisely reflect the disease-specific alteration of glycans on the lung cancer differential marker glycoproteins. This approach, however, inevitably requires antibodies that permit immunoprecipitation and overlay detection. Nevertheless, such antibodies are not always available. In this regard, the immunological quantitative detection of target glycoproteins from among glycoproteins collected with probe lectins is generally carried out as means for using a larger number of candidate molecules in the detection of lung cancer. Specifically, SDS-PAGE is performed, and target glycoproteins are immunologically detected by Western blot after membrane transfer. The signal intensities of the obtained bands can be compared to thereby quantitatively estimate the change between samples. The significance of each marker candidate can be validated on the basis of change in the amount of the protein having the cancer-specific alteration of a glycan, to thereby narrow down the candidate glycoproteins. In this embodiment, generally, the AAL lectin used in the step of identifying candidate molecules is also used as a probe protein in this validation. Examples of practice under such a strategy include the report of Liu Y et al., J Proteome Res. 9, 798-805 (2010). Serum proteins are known to differ in the structures (the degree of branching, etc.) or fucosylation (core fucose, blood group antigen, etc.) of their N-linked glycans, depending on the types thereof. Reportedly. even the same molecules may therefore be differently fucosylated. For example, Nakagawa T. et al., J. Biol. Chem. 281, 29797-29806 (2006) discloses that al antitrypsin molecules are differently fucosylated. Such proteins may or may not be increased at different times depending on the type of disease and the stage of its progression. Thus, the approach is not ideal, in which all fucose-containing glycoproteins are collected using AAL probes, which can recognize almost all fucosylation patterns and collect the glycoproteins, and the collected glycoproteins are quantitatively compared. Hence, we have conceived that proteins are separated and fractionated by serial chromatography using two different fucose-recognizing lectins and these fractions are quantitatively compared and analyzed. The lectins used in this approach are LCA and AAL. Previous lectin specificity analysis has revealed that the LCA lectin recognizes core-fucosylated glycans with fewer branches, among N-linked glycans. The AAL lectin is known to be capable of recognizing every core fucose with any number of branches in N-linked glycans as well as even fucosylation at the non-reducing end typified by ABO, Lewis antigens, or the like. This means that LCA has high specificity while AAL has low specificity. Thus, in the first step, fucose-containing glycoproteins binding to LCA are captured by LCA column chromatography. These glycoproteins are regarded as LCA-bound fucose-containing glycoproteins. In this chromatography, fucose-containing glycoproteins having no core-fucosylated N-linked glycan with fewer branches are fractionated into unbound fractions without binding to the LCA column. In order to capture such fucose-containing glycoprotein groups from the LCA-unbound fractions, the LCA-unbound fractions are subjected to AAL column chromatography. The glycoprotein groups captured by AAL in this step are regarded as LCA-unbound/AAL-bound fucose-containing glycoproteins. These procedures can presumably evaluate increase or decrease in fucosylation of the same protein associated with the disease, on the basis of the type of modification.

2. Method for Determining Lung Cancer

The second embodiment of the present invention provides a method for determining lung cancer. The method of this embodiment comprises detecting the lung cancer differential marker of embodiment 1 from a sample obtained from a test subject, wherein the detection of the glycoprotein or fragment determines that the test subject suffers lung cancer.

2-1. Definition and Summary

In the present specification, the "test subject" refers to a person to be subjected to a test, i.e., a human donor of a sample described later. The test subject may be any of patients having a certain disease or healthy persons. The test subject is preferably a person possibly having lung cancer or a lung cancer patient.

The "sample" refers to a part that is obtained from the test subject and subjected to the differential method of this embodiment. For example, a body fluid, a cell from cancer tissue or the like, or a lung lavage obtained during operation applies to the sample.

The "body fluid" refers to a biological sample in a liquid state obtained from the test subject. Examples thereof include blood (including serum, plasma, and interstitial fluid), lymph, extracts of each tissue or cell, pleural effusion, sputum, spinal fluid, lacrimal fluid, nasal discharge, saliva, urine, vaginal fluid, and seminal fluid. The body fluid is preferably blood, lymph, pleural effusion, or sputum. The body fluid may be used, if necessary, after treatment such as the dilution or concentration of the sample obtained from the test subject or the addition of an anticoagulant such as heparin thereto. Alternatively, the body fluid may be used directly without such pretreatment. The body fluid can be obtained by a method known in the art. For example, blood or lymph can be obtained according to a blood collection method known in the art. Specifically, peripheral blood can be obtained from the vein or the like of a peripheral site by injection. The body fluid may be used immediately after obtainment. Alternatively, the body fluid may be cryopreserved or refrigerated for a given period and then treated, if necessary, by thawing or the like before use. In this embodiment, in the case of using serum, sufficient amounts of lung cancer differential markers can be detected using a volume of 10 µL to 100 µL, 20 µL to 80 µL, 30 µL to 70 µL, 40 µL to 60 µL, or 45 µL to 55 µL.

In the differential method of this embodiment, the lung cancer diagnosis marker used in detection can be any lung cancer diagnosis marker as long as the marker is a lung cancer marker glycoprotein listed in Table 1 or 2 being glycosylated with a glycan at the asparagine residue(s) at the glycosylation site(s) shown in Table 1 or 2, or a glycoprotein fragment thereof comprising at least one asparagine residue at the glycosylation site shown in Table 1 or 2 being glycosylated with a glycan. These lung cancer diagnosis markers may be used alone or in combination of two or more thereof in the diagnosis method of this embodiment. For example, two or more different lung cancer diagnosis marker glycoproteins may be used. Alternatively, two or more different fragments of the same lung cancer diagnosis marker glycoprotein may be used. Preferably, the lung cancer diagnosis marker(s) shown in Table 1 is used. More preferably, lung cancer diagnosis markers having the same or different diagnostic characteristics for small cell lung cancer and lung adenocarcinoma are used. Examples of the use method include a method using neural cell adhesion molecule (NCAM1), secretogranin III, and/or insulin-like growth factor-binding protein-L1 (IGFBP-L1) shown in Table 1 for differential diagnosis of small cell lung cancer, in combination with fibronectin 1 shown in Table 1 for differential diagnosis of lung adenocarcinoma as the lung cancer differential markers of this embodiment. This method is convenient because it can determine the presence or absence of lung cancer in the test subject while also determining the histological type (small cell cancer or adenocarcinoma) of the lung cancer. When the lung cancer differential marker shown in Table 1 or 2 is detected from the sample of the test subject by any method using, alone or in combination, lectins or antibodies binding to a fucosylated glycan, a high mannose-type glycan, a hybrid-type glycan, a biantennary complex-type glycan, chitin, polylactosamine, and/or a pβ1,3-galactose epitope, this test subject can be confirmed to have lung cancer or to be highly likely to have lung cancer. For example, the fucosylated glycan can be detected using AAL lectin specifically binding thereto. The high mannose-type glycan, the hybrid-type glycan, and the biantennary complex-type glycan can be detected using ConA lectin specifically binding thereto. The chitin and the polylactosamine can be detected using PWM lectin specifically binding thereto. The β1,3-galactose epitope can be detected using PNA lectin specifically binding thereto.

Alternatively, the histological type of lung cancer in the test subject may be confirmed as small cell cancer or adenocarcinoma on the basis of results of binding of the lectin to the glycan in the lung cancer differential marker in the sample obtained from the test subject, and the manner of binding of the lung cancer differential marker glycoprotein shown in Table 1 or 2 and/or the fragment thereof to the lectin. According to the manner of lectin binding of the glycoprotein shown in Table 1, for example, the glycans of acid alpha-glucosidase represented by Protein #1 bind to AAL lectin only in small cell lung cancer. Thus, when acid alpha-glucosidase bound to AAL lectin is detected from the sample obtained from a test subject, this test subject can be confirmed to have lung cancer whose histological type is small cell cancer. Alternatively, when neural cell adhesion molecule (NCAM1) as the lung cancer differential marker glycoprotein or its glycoprotein fragment bound with AAL lectin is detected, the histological type of lung cancer can be confirmed as small cell cancer. When fibronectin 1 as the lung cancer differential marker glycoprotein or its glycoprotein fragment bound with AAL lectin or an anti-fibronectin 1 (fragment) antibody is detected, the histological type of lung cancer can be confirmed as adenocarcinoma.

2-2. Method for Detecting Lung Cancer Differential Marker

Examples of the method for detecting the lung cancer differential marker can include the combination of two methods: a method involving using a lectin specifically binding to a glycan in each lung cancer differential marker (hereinafter, in the present specification, this lectin is referred to as lectin A for the sake of convenience) to select a lung cancer differential marker having the glycan; and a method involving detecting a moiety (core protein) other than the glycan of each lung cancer differential marker to thereby detect the lung cancer differential marker. Alternative examples of the method can include a method involving using an antibody to detect the lung cancer differential marker of interest, the antibody being specific for the lung cancer differential marker having a glycan specifically binding to lectin A and recognizing an epitope located in proximity to the glycosylation site.

In this context, the method of detecting a glycan specifically binding to lectin A and the method of detecting a core protein may be a method of assaying a glycan specifically binding to lectin A and a method of assaying a core protein, respectively. For example, the lung cancer differential marker can be detected using an antibody against the core protein and lectin A to thereby differentiate between lung cancer patients and healthy persons. Preferably, the antibody overlay method using a lectin array (Kuno A, Kato Y, Matsuda A, Kaneko M K, Ito H, Amano K, Chiba Y, Narimatsu H, Hirabayashi J. Mol Cell Proteomics. 8, 99-108 (2009)) can be used. More simply, the lectin-antibody sandwich immunological detection method can be used for detection.

Examples of the specific method for determining lung cancer using the lung cancer differential marker having a glycan specifically binding to lectin A include a method comprising the following steps:

(1) separating lung cancer differential markers using lectin A from serum obtained from a test subject to thereby select a protein group having the glycan specifically binding to lectin A; and (2) subsequently screening the lung cancer differential markers using an anti-lung cancer differential marker glycoprotein antibody specifically recognizing the moiety other than the glycan specifically binding to lectin A, to thereby detect the lung cancer differential marker of interest having the glycan specifically binding to lectin A, wherein when this marker is detected, this test subject is determined to be afflicted with lung cancer.

The lung cancer differential marker having the glycan specifically reacting with lectin A can be selected using, for example, the method of assaying a glycan specifically binding to lectin A using, specifically, a lectin A-immobilized column or array, and lung cancer differential marker assaying means, specifically, an antibody against the novel lung cancer differential marker glycoprotein or the fragment thereof. Preferably, the lectin-antibody sandwich ELISA or the antibody-overlay lectin array method can be used.

Also, the concentration of the lung cancer differential marker having the glycan specifically reacting with lectin A can be measured. Examples of the measurement method include the antibody-overlay lectin array method using a lectin array, LC-MS, immunoassay, enzymatic activity assay, and capillary electrophoresis. Preferably, a qualitative or quantitative approach can be used, which includes: LC-MS; and enzyme immunoassay, two-antibody sandwich ELISA, gold colloid method, radioimmunoassay, latex agglutination immunoassay, fluorescent immunoassay, Western blot, immunohistochemical method, surface plasmon resonance spectroscopy (SPR method), and quartz crystal microbalance (QCM) method, using a monoclonal or polyclonal antibody specific for the novel lung cancer differential marker glycoprotein having the glycan specifically reacting with lectin A or the fragment thereof.

2-3. Preparation of Specific Polyclonal and/or Monoclonal Antibodies Using Lung Cancer Differential Marker Glycoprotein or its Glycopeptide In the method for detecting lung cancer using the novel lung cancer differential marker glycoprotein or its fragment glycopeptide, polyclonal and/or monoclonal antibodies specific for the differential marker glycoprotein or its glycopeptide may be used. For example, an easily obtainable antibody, such as a commercially available antibody, specific for the glycoprotein or the like can be used. If such an antibody is not easily obtainable, it can be prepared, for example, by the following method:

For example, the anti-lung cancer differential marker glycopeptide polyclonal antibody can be prepared using a well-known method. Specifically, an adjuvant is added to an obtained antigenic lung cancer differential marker glycoprotein or glycopeptide. The antigen used may be synthesized as a lung cancer differential marker glycopeptide containing glycosylation site(s) (asparagine residue(s)). Examples of the adjuvant include complete Freund's adjuvant and incomplete Freund's adjuvant. These adjuvants may be used as a mixture. The antigen may be inoculated, together with the adjuvant, to an antibody-producing animal to thereby boost antibody production. Alternatively, this peptide may be covalently bonded to commercially available keyhole limpet hemocyanin (KLH) and inoculated to an antibody-producing animal. In this procedure, granulocyte-macrophage colony stimulating factor (GM-CSF) may also be administered to the animal simultaneously therewith to thereby boost antibody production. Examples of the antibody-producing animal that can be used in antigen inoculation include mammals, for example, mice, rats, horses, monkeys, rabbits, goats, and sheep. Immunization can employ any of existing methods and is performed mainly by intravenous injection, hypodermic injection, intraperitoneal injection, or the like. The interval between immunization doses is not particularly limited and is an interval of several days to several weeks, preferably 4 to 21 days.

2 to 3 days after the final immunization date, whole blood is obtained from the immunized animal. After serum separation, the polyclonal antibody can be prepared.

Alternatively, for example, the anti-lung cancer marker glycopeptide monoclonal antibody can be prepared by the method of Kohler and Milstein (Nature Vol. 256, pp. 495-497 (1975)). For example, antibody-producing cells obtained from the antigen-immunized animal are fused with myeloma cells to prepare hybridomas. From the obtained hybridomas, clones producing the anti-lung cancer differential marker glycopeptide monoclonal antibody can be selected to thereby prepare the monoclonal antibody.

Specifically, 2 to 3 days after the final immunization date in the preparation of the polyclonal antibody, antibody-producing cells are collected. Examples of the antibody-producing cells include spleen cells, lymph node cells, and peripheral blood cells.

Cell lines that are derived from various animals (e.g., mice, rats, and humans) and are generally obtainable by those skilled in the art are used as the myeloma cells to be fused with the antibody-producing cells. The cell line used is a drug resistance cell line that cannot survive in a selective medium (e.g., HAT medium) in an unfused state, but can characteristically survive therein only in a fused state. In general, 8-azaguanine-resistant line is used. This cell line is deficient in hypoxanthine-guanine-phosphoribosyl transferase and cannot grow in a hypoxanthine-aminopterin-thymidine (HAT) medium.

The myeloma cells have already been known in the art, and various cell lines can be used preferably, for example, P3(P3x63Ag8.653) (J. Immunol. 123, 1548-1550 1979)), P3x63Ag8U.1 (Current Topics in Microbiology and Immunology 81, 1-7 (1978)), NS-1 (Kohler, G. and Milstein, C., Eur. J. Immunol. 6, 511-519 (1976)), MPC-11 (Margulies, D. H. et al., Cell 8, 405-415 (1976)), SP2/0 (Shulman, M. et al., Nature 276, 269-270 (1978)), FO (de St. Groth, S. F. et al., J. Immunol. Methods 35, 1-21 (1980)), S194 (Trowbridge, I. S., J. Exp. Med. 148, 313-323 (1978)), and R210 (Galfre, G. et al., Nature 277, 131-133 (1979)).

Next, the myeloma cells and the antibody-producing cells are fused with each other. This cell fusion is performed by the contact between the myeloma cells and the antibody-producing cells at a mixing ratio of 1:1 to 1:10 at 30 to 37° C. for 1 to 15 minutes in the presence of a fusion promoter in a medium for animal cell culture such as MEM, DMEM, or RPMI-1640 medium. A fusion promoter or a fusion virus, such as polyethylene glycol or polyvinyl alcohol having an average molecular weight of 1,000 to 6,000 or Sendai virus can be used for promoting the cell fusion. Alternatively, the antibody-producing cells and the myeloma cells may be fused with each other using a commercially available cell fusion apparatus based on electrical stimulation (e.g., electroporation).

After the cell fusion, hybridomas of interest are selected from the fused cells. Examples of the method therefor include a method using selective growth of the cells in a selective medium. Specifically, the cell suspension is diluted with an appropriate medium and then seeded over a microtiter plate. A selective medium (e.g., HAT medium) is added to each well, and the cells are subsequently cultured with the selective medium appropriately replaced by a fresh one. As a result, the cells that have grown can be obtained as hybridomas.

The hybridoma screening is performed by, for example, a limiting dilution method or a fluorescence excitation method using a cell sorter. Finally, monoclonal antibody-producing hybridomas are obtained. Examples of the method for obtaining the monoclonal antibody from the obtained hybridomas include ordinary cell culture and ascitic fluid formation methods.

3. Lung Cancer Cell-Identifying Antibody for Histological Staining

The third embodiment of the present invention provides a lung cancer cell-identifying antibody for histological staining. The antibody of this embodiment is an antibody that can specifically recognize and bind to the lung cancer differential marker according to embodiment 1, i.e., at least one lung cancer differential marker glycoprotein shown in Table 1 or 2 being glycosylated with a glycan at the asparagine residue(s) at the glycosylation site(s) shown in Table 1 or 2, and/or at least one fragment thereof, the fragment comprising at least one asparagine residue at the glycosylation site shown in Table 1 or 2 being glycosylated with a glycan, and thereby specifically identifying a lung cancer cell in histological staining.

The epitope of the lung cancer differential marker according to embodiment 1 recognized by the antibody of this embodiment is not particularly limited and is preferably a core protein or a fragment of the core protein, more preferably a moiety encompassing both of a glycan and its neighboring peptide sequence. In this case, the length of the peptide sequence is 5 to 15 amino acids, 5 to 10 amino acids, or 5 to 8 amino acids. In addition to this antibody probe, a phage antibody probe prepared using a phage can also be used as a glycan probe for identification of a lung cancer cell.

Figure 7:
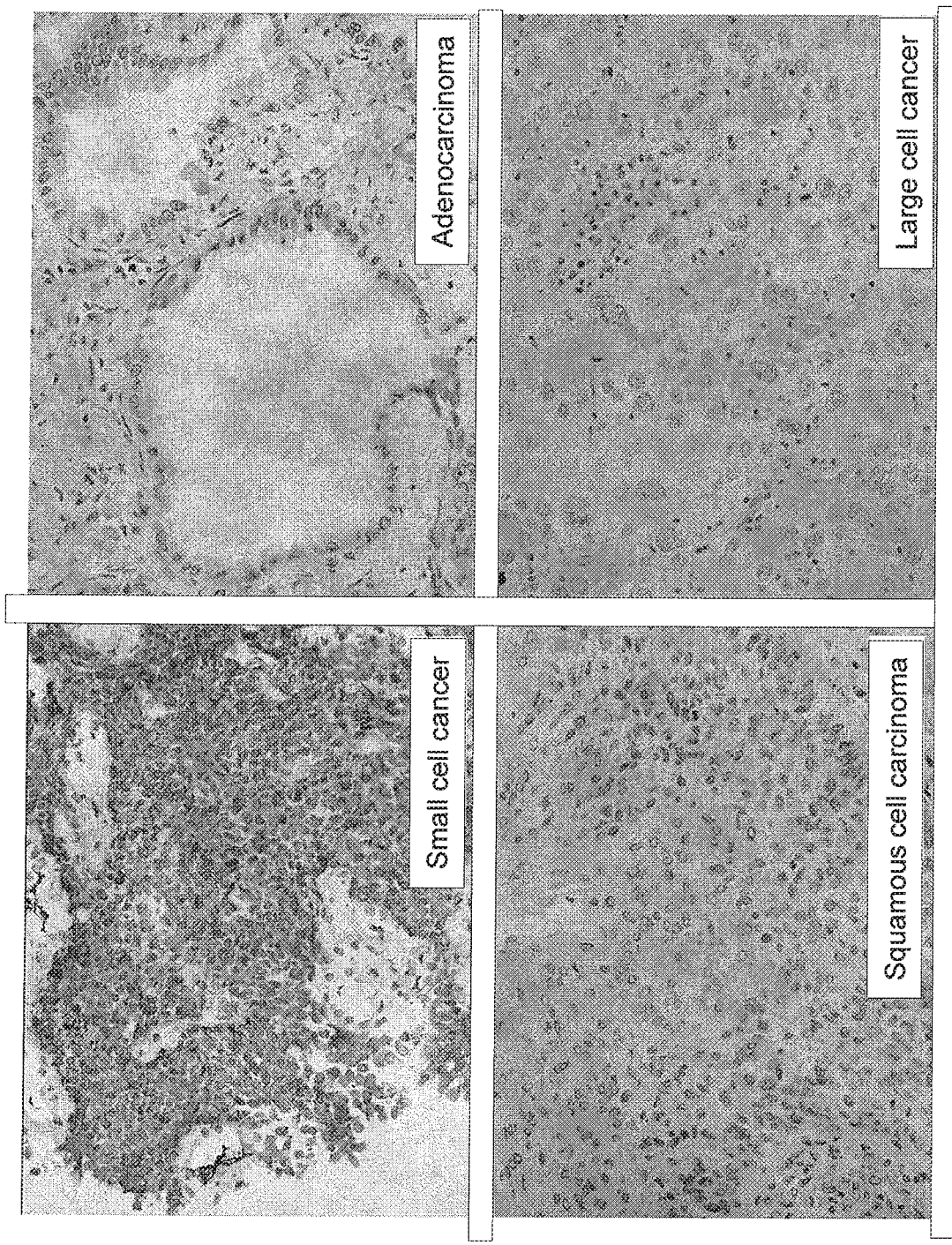
FIG. 7 is an image of histological staining of each histological type of lung cancer with an anti-neuronal pentraxin receptor (NPR) antibody.

The antibody of this embodiment is capable of determining the histological type of a lung cancer cell. Examples of such an antibody include an antibody (R&D Systems, Inc., Anti-human Neuronal Pentraxin Receptor Antibody) against neuronal pentraxin receptor (NPR) represented by Protein #21 in Table 1. This anti-neuronal pentraxin receptor antibody is capable of specifically identifying a small cell cancer-derived cell, as shown in FIG. 7, and as such, can serve as an antibody for identification of a small cell cancer cell. Thus, the proteins collected and identified with cancer-specific glycan probe lectins are usually expressed at an exceedingly low level at other tissues or normal sites and thus include tissue markers that can function by means of only the antibody or the phage antibody without the need of differentiating between small cell cancer-derived cells and lung adenocarcinoma-derived cells using lectins or the like.

EXAMPLES

Example 1

Selection of Glycopeptide Marker by Glycoproteomics (IGOT-LC/MS Method)

1. Method for Preparing Culture Supernatant of Human Lung Cancer Cell

Three lung adenocarcinoma cell lines (H358, H1975, and LX-1) and three small cell lung cancer cell lines (H2171, H524, and H526) were separately cultured for 3 days using a high-glucose medium containing 90% DMEM and 10% FBS (PS+) in a dish having a diameter of 14 cm to achieve 80 to 90% confluence. The FBS-containing medium was discarded by aspiration, and the cells of each line were washed with 10 mL/dish of a serum-free medium (100% DMEM-high glucose, no additive). After addition of a serum-free medium at a concentration of 30 mL/dish, the cells were cultured for 48 hours. The cells thus cultured were centrifuged at 1000 rpm for 30 minutes to recover a supernatant. The supernatant (culture supernatant) was further recovered by centrifugation at 3000 rpm for 30 minutes and cryopreserved at −80° C. The culture supernatant stored at this temperature was thawed before use, filtered through a 0.45-μm filter, and then used in Examples below. NaN$_3$ was added to each culture supernatant to adjust the final concentration to 0.1%.

2. Method for Identifying Glycoprotein at Large Scale (1) Preparation of Peptide Sample Trichloroacetic acid (TCA, 100% saturated aqueous solution) was added at a final concentration of 10% to each culture supernatant thus prepared. The mixture was cooled on ice for 10 to 60 minutes to precipitate proteins. The precipitates were recovered by centrifugation at a high speed at 4° C. The precipitates were suspended in ice-cold acetone and washed twice to remove TCA. A lysis buffer solution (containing 0.5 M tris-HCl buffer solution, pH 8-8.5, 7 M guanidine hydrochloride, and 10 mM EDTA) was added to the precipitates to adjust the protein concentration to 5 to 10 mg/mL, while the proteins were lysed therein. In another method, each culture supernatant was applied to an ultrafiltration membrane having a molecular weight cutoff of 10,000 at 4° C. to concentrate proteins, to which a lysis buffer solution was then added. The protein solution was filtered again to prepare a sample protein solution.

Extracts were recovered from each supernatant by centrifugation at a high speed. Nitrogen gas was passed through or sprayed to the extracts to remove dissolved oxygen. Then, dithiothreitol (DTT) in the form of a powder or dissolved in a small amount of a lysis buffer solution was added thereto in an amount equal to the protein weight. The mixture was reacted at room temperature for 1 to 2 hours with nitrogen gas passed therethrough or in a nitrogen gas atmosphere to reduce the disulfide bond. Subsequently, iodoacetamide for S-alkylation was added thereto in an amount of 2.5 times the protein weight. The mixture was reacted at room temperature for 1 to 2 hours in the dark. The reaction solution was dialyzed at 4° C. (cooling room) against a 50- to 100-fold amount of a buffer solution (in general, 10 mM ammonium bicarbonate buffer solution, pH 8.6) as an external solution. The external solution was replaced by a fresh one three to five times at appropriate time intervals to remove the denaturant (guanidine hydrochloride) or an excess of the reagents. Although proteins were partially precipitated, this suspension was subjected directly to protein quantification. Trypsin (sequencing grade or higher) with a weight of 1/100 to 1/50 of the protein amount was added thereto to digest the proteins overnight (approximately 16 hours) at 37° C. The progression of the digestion was confirmed by SDS-gel electrophoresis. When sufficient digestion was confirmed, the reaction was terminated by the addition of phenylmethanesulfonyl fluoride (PMSF) at a final concentration of 5 mM.

(2) Collection and Purification of Candidate Glycopeptide

The sample peptides prepared in the preceding step were applied to probe lectin (AAL lectin or ConA lectin)-immobilized columns. After washing, candidate glycopeptides were eluted by a method appropriate for the specificity of each lectin, i.e., using a buffer solution containing 5 mM fucose as to the AAL lectin and using a buffer solution containing 0.2 M methylmannoside as to the ConA lectin. To the obtained candidate glycopeptide solution, an equal volume of ethanol and a 4-fold volume of 1-butanol were added, and the mixture was applied to a Sepharose™ column equilibrated in advance with water:ethanol:1-butanol (1:1:4 (v/v)). The column was washed with this equilibrating solvent, and candidate glycopeptides were then eluted with 50% ethanol (v/v). Each candidate glycopeptide fraction was transferred in small portions to a microtube containing 2 μL of glycerol and concentrated by centrifugation under reduced pressure (i.e., water was removed by centrifugation under reduced pressure). This procedure was repeated to concentrate all candidate glycopeptide fractions.

(3) Glycan Cleavage and Isotope-Coded Glycosylation Site-Specific Tagging (IGOT) Method A necessary amount of a buffer solution was added to the purified candidate glycopeptides (glycerol solution), and the mixture was concentrated again by centrifugation under reduced pressure. Then, stable oxygen isotope-18 ($^{18}$O)-labeled water (H$_2$$^{18}$O) was added thereto to dissolve the concentrate (glycerol concentration: 10% or lower). Peptide-N-glycanase (glycopeptidase F, PNGase) prepared with labeled water was added thereto and reacted overnight at 37° C. This reaction causes the conversion of the glycosylated asparagine to aspartic acid, during which the oxygen isotope ($^{18}$O) in the water is incorporated into the candidate glycopeptide to label the candidate glycopeptide.

(4) LC/MS Shotgun Analysis of Labeled Peptide

The IGOT reaction solution was diluted with 0.1% formic acid and subjected to LC/MS shotgun analysis. In this analysis, a nano-LC system based on a direct nano-flow pump was used for high-separation, high-reproducibility, and high-sensitivity detection. The injected candidate glycopeptides were temporarily collected onto a trap column (reverse-phase C18 silica gel carrier) intended for desalting. After washing, the glycopeptides were separated by the concentration gradient of acetonitrile using frit-less spray tip nano-columns (inside diameter: 150 μm×50 mL) packed with the same resins. The eluate was ionized via an electrospray interface and directly introduced into a mass spectrometer. The glycopeptides were analyzed by collision-induced dissociation (CID)-tandem mass spectrometry in a data-dependent mode in which two ions at the maximum to be analyzed were selected.

(5) Search for Candidate Glycopeptide by MS/MS Ion Search Method

Thousands of MS/MS spectra thus obtained were individually smoothed and converted to centroid spectra to prepare peak lists. On the basis of the peak lists, each candidate glycopeptide was identified by the MS/MS ion search method using a protein amino acid sequence database. The search engine used was Mascot (Matrix Science Ltd.). The following parameters were used for search conditions: a fragmentation method used: trypsin digestion, the maximum number of missed cleavage: 2, fixed modification: carbamidomethylation of cysteine, variable modifications: deamination of an N-terminal amino group (N-terminal glutamine), oxidation of methionine, $^{18}O$-incorporating deamidation of asparagine (glycosylation site), error tolerance of MS spectrum: 500 ppm, and error tolerance of MS/MS spectrum: 0.5 Da.

(6) Identification of Candidate Glycopeptide

The database was searched under the conditions described above. The obtained identification results were validated according to criteria shown below. The obtained candidate glycopeptides were regarded as lung cancer differential marker glycopeptides (lung cancer differential marker glycoprotein fragments).

(i) The probability score (coincidence probability: Expectation value) of identification is 0.05 or less.

(ii) The number of fragment ions contributing to identification is 4 or more.

(iii) Error (ppm) is not significantly deviated from systematic error (mass error being 0.5 Da or less).

(iv) Each identified peptide has consensus sequence(s) with the number of Asn modifications (conversion to Asp and incorporation of $^{18}O$) equal to or fewer than the number of the consensus sequence(s).

(7) Identification of Lung Cancer Differential Marker Glycoprotein

Glycoproteins containing the sequences of the selected lung cancer differential marker glycopeptides can be identified using these sequences. More specifically, the whole amino acid sequences of corresponding lung cancer differential marker glycoproteins were identified from the amino acid sequence database NCBI-Refseq on the basis of the "peptide sequences" of lung cancer differential marker glycopeptides represented by SEQ ID NOs: 1 to 223 in Tables 1 and 2.

(Results)

The lung cancer differential marker glycoproteins obtained by the steps described above are shown in Table 2.

3. Validation of Culture Supernatant-Derived Protein by Immunoblot

Each of the culture supernatants of lung cancer cell lines (three lung adenocarcinoma cell lines: H358, 111975, and LX-1, and three small cell lung cancer cell lines: H2171, H524, and H526) separately cultured for 24 hours in a serum-free medium was concentrated 10-fold through Amicon Ultra-154 Centrifugal Filter Units (cutoff: 10 kDa, Millipore Corp.). Each sample (10 µL) was developed by SDS-PAGE on a 10%, 12.5%, or 17% acrylamide gel of XV PANTERA SYSTEM (Maruko Shokai Co., Ltd.) and then transferred to a PVDF membrane (GE Healthcare Japan Corp.) at 200 mA for 40 min. The blocking agent used was PBSTx (Dulbecco's PBS supplemented with 1% Triton X-100) containing 5% skimmed milk or 5% BSA dissolved therein. The membrane was blocked at room temperature for 1 hour. After 10-minute washing three times with PBSTx, the membrane was reacted for 1 hour with primary antibodies (Table 4) biotinylated in advance with Biotin Labeling Kit-Ni$_2$ (Dojindo Laboratories). After 10-minute washing three times with PBSTx again, the membrane was reacted for 1 hour with secondary antibody-HRP-conjugated streptavidin (1:3000 dilution, GE Healthcare Japan Corp.). After 10-minute washing three times with PBSTx, the enzymatic reaction of HRP was caused using Western Lightning Chemiluminescence Reagent Plus (PerkinElmer, Inc.). The obtained signals were developed onto Amersham Hyperfilm ECL (GE Healthcare Japan Corp.). The amounts of proteins present in the culture supernatants derived from the lung adenocarcinoma and small cell lung cancer cell lines were analyzed by comparison.

TABLE 4

| Antibody # | Antibody name [Manufacturer: Catalog No./Distributer] |
|---|---|
| 01 | neural cell adhesion molecule 1 (NCAM-1/CD56) [LSP: MAB24081/Funakoshi Corp.] |
| 02 | neuronal pentraxin II (NPTX2) [LSP: LS-C53292-50/Funakoshi Corp.] |
| 03 | Thy-1 cell surface antigen [ABV: H00007070-M01/Cosmo Bio Co., Ltd.] |
| 04 | insulin-like growth factor 2 receptor (IGF-IIR) [RSD: AF2447/Cosmo Bio Co., Ltd.] |
| 05 | insulin-like growth factor 2 receptor (IGF-IIR) [RSD: MAB2447/Funakoshi Corp.] |
| 06 | acid alpha-glucosidase preproprotein (GAA) [LSP: LS-C80648-50/Cosmo Bio Co., Ltd.] |
| 07 | sparc/osteonectin, cwcv and kazal-like domains proteoglycan 2 (testican2/SPOCK2) [RSD: MAB2328/Funakoshi Corp.] |
| 08 | sparc/osteonectin, cwcv and kazal-like domains proteoglycan 2 (testican2/SPOCK2) [ABV: H00009806-B01P/Funakoshi.Corp.] |
| 09 | cell adhesion molecule 4 (CADM4) [LSP: LS-C36881/Cosmo Bio Co., Ltd.] |
| 10 | secretogranin III (SgIII) [SCB: SC-1492/Cosmo Bio Co., Ltd.] |
| 11 | melanoma-associated antigen p97 (MFI2) [ABV: H00004241-B01P/Cosmo Bio Co., Ltd.] |
| 12 | cathepsin L2 preproprotein (CTSL2) [ABV: PAB8639/Cosmo Bio Co., Ltd.] |
| 13 | cathepsin L2 preproprotein (CTSL2) [DFK: F-106/Cosmo Bio Co., Ltd.] |
| 14 | lysosomal acid phosphatase 2 precursor (ACP2) [ABV: PAB7218/Cosmo Bio Co., Ltd.] |
| 15 | lysosomal acid phosphatase 2 precursor (ACP2) [ABV: H00000053-M01/Cosmo Bio Co., Ltd.] |
| 16 | cathepsin L1 (CTSL1) [ABV: PAB8638/Cosmo Bio Co., Ltd.] |
| 17 | cathepsin L1 (CTSL1) [ABV: MAB1432/Cosmo Bio Co., Ltd.] |
| 18 | deoxyribonuclease II, lysosomal precursor (DNASE2) [ABV: H00001777-B01P/Cosmo Bio Co., Ltd.] |
| 19 | integral membrane protein 1 (ITM1) [SCB: SC-100796/Funakoshi Corp.] |
| 20 | integral membrane protein 1 (ITM1) [ABV: H00003703-M02/Cosmo Bio Co., Ltd.] |
| 21 | neuronal pentraxin receptor (NPTXR/NPR) [RSD: AF4414/Funakoshi Corp.] |
| 22 | neuronal pentraxin receptor (NPTXR/NPR) [LSP: LS-C73727-100/Funakoshi Corp.] |

TABLE 4-continued

| Antibody # | Antibody name [Manufacturer: Catalog No./Distributer] |
|---|---|
| 23 | neuronal pentraxin receptor (NPTXR/NPR) [SCB: SC-12483/Cosmo Bio Co., Ltd.] |
| 24 | sushi domain containing 2 (SUSD2) [ABV: H00056241-B01/Cosmo Bio Co., Ltd.] |
| 25 | sel-1 suppressor of lin-12 like (SEL1L) [LSP: LS-B2253-50/Funakoshi Corp.] |
| 26 | sel-1 suppressor of lin-12 like (SEL1L) [LSP: LS-C55443-100/Funakoshi Corp.] |
| 27 | sel-1 suppressor of lih-12 like (SEL1L) [ABV: PAB7473/Cosmo Bio Co., Ltd.] |
| 28 | source of immunodominant MHC-associated peptides (STT3B) [PG: 15323-1-AP/Cosmo Bio Co., Ltd.] |
| 29 | IGFBP-L1 [RSD: AF3877/Cosmo Bio Co., Ltd.] |
| 30 | neural cell adhesion molecule 1 (NCAM-1/CD56) [SCB: sc-71647/Cosmo Bio Co., Ltd.] |
| 31 | Fibronectin (H-300) [SCB: sc-9068/Cosmo Bio Co., Ltd.] |
| 32 | Galectin-3BP/MAC-2BP (MAC2BP) [RSD: AF2226/Cosmo Bio Co., Ltd.] |
| 33 | Cathepsin D [RSD: AF1014/Cosmo Bio Co., Ltd.] |
| 34 | Fibronectin (C-20) [SCB: sc-6952/Cosmo Bio Co., Ltd.] |
| 35 | neogenin homolog 1 (NGN) [SCB: SC-15337]/Cosmo Bio Co., Ltd.] |
| 36 | laminin alpha 5 [SCB: SC-20145/Cosmo Bio Co., Ltd.] |
| 37 | laminin, beta 1 precursor [SCB: sc-17763/Cosmo Bio Co., Ltd.] |
| 38 | phospholipid transfer protein isoform b precursor (PLTP) [RSD: AF5109/Cosmo Bio Co., Ltd.] |
| 39 | melanoma cell adhesion molecule (MCAM) [Millipore: MAB16985/] |
| 40 | L1 cell adhesion molecule isoform 2 precursor (L1CAM) [LSP: LS-C49042/Cosmo Bio Co., Ltd.] |
| 41 | biotinidase precursor (BTD) [ABV: H00000686-M01/Funakoshi Corp.] |
| 42 | ribonuclease T2 precursor (RNASET2) [ABV: H00008635-B01/Cosmo Bio Co., Ltd.] |
| 43 | tubulointerstitial nephritis antigen-like 1 (TINAGL1) [ABV: H00064129-B02P/Cosmo Bio Co., Ltd.] |
| 44 | v-kit Hardy-Zuckerman 4 feline sarcoma viral oncogene homolog isoform 2 precursor (KIT) [LSP: LS-C40873-100/Cosmo Bio Co., Ltd.] |
| 45 | secretogranin III (SgIII) [SCB: SC-50289] |
| 46 | secretogranin III (SgIII) [SIGMA: HPA-006880] |
| 47 | IGFBP-L1 [RSD: BAF3877/Cosmo Bio Co., Ltd.] |

(Results)

Figure 2:
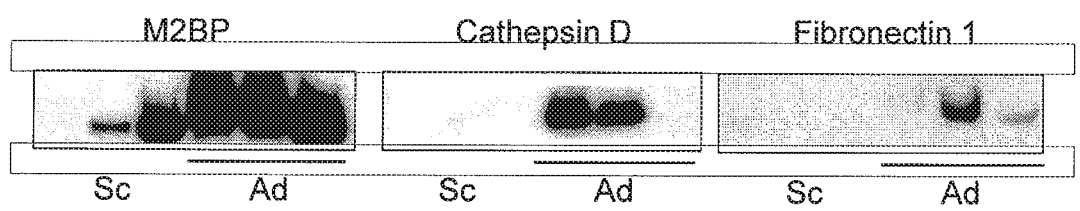
FIG. 2 is a Western blot image showing the expression of lung adenocarcinoma differential marker glycoproteins in the culture supernatants of cultured small cell lung cancer cells (Sc) and cultured lung adenocarcinoma cells (Ad).

The lung cancer differential marker glycoproteins obtained by the steps described above are shown in Table 1 and FIGS. 1 and 2.

4. Batch Fractionation of Culture Supernatant Using AAL Lectin

The culture supernatants were fractionated using AAL lectin. Specifically, an AAL-conjugated resin was washed five times with a 3-fold amount of PBS and then prepared into a 50% slurry solution. To 30 μL of the prepared AAL-conjugated resin, 30 μL of each culture supernatant was added, and the resin was shaken at 4° C. for 5 hours. After centrifugation (2,000 rpm, 2 min.), the supernatant was removed, and 50 μL of a wash buffer (0.1% SDS in PBST, and 0.1% Triton X-100) was then added to the resulting resin. After centrifugation (2,000 rpm, 2 min.) two times, 500 μL of a wash buffer was added thereto. The supernatant was removed by centrifugation (2,000 rpm, 2 min.), and the resin was washed. For elution from the washed resin, 15 μL of 0.2 M fucose in PBS containing 0.02% SDS was added thereto, and the resin was shaken at 4° C. for 5 hours. After centrifugation (2,000 rpm, 2 min.), the supernatant was recovered. 15 μL of an elution buffer was further added thereto, and the resin was centrifuged (2,000 rpm, 2 min.) to elute AAL-bound fractions. 10 μL each of the eluted fractions was developed by SDS-PAGE, and proteins were detected by Western blot. Similar procedures were performed using ConA lectin except that 0.5 M methylmannoside was used in elution.

(Results)

Figure 3:
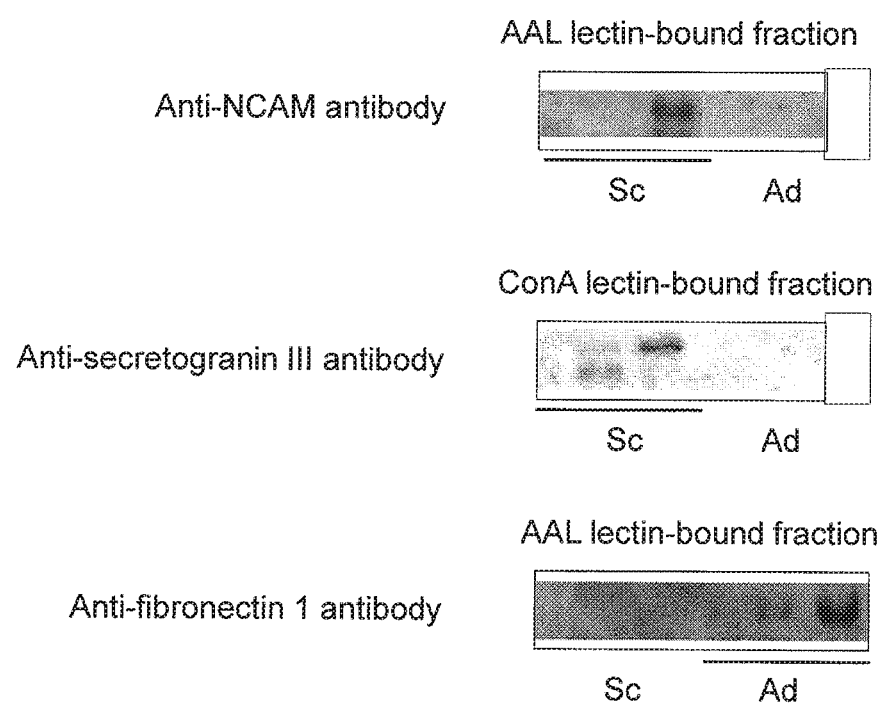
FIG. 3 is a Western blot image in which lung cancer differential marker glycoproteins in the culture supernatants of cultured small cell lung cancer cells (Sc) and cultured lung adenocarcinoma cells (Ad) fractionated with each lectin were detected with their respective anti-lung cancer differential marker protein antibodies.

The lung cancer differential marker glycoproteins obtained by the steps described above are shown in FIG. 3.

5. Fractionation by Immunoprecipitation

Antibodies against all the candidate glycoproteins shown in Table 1 were biotinylated, if unbiotinylated, using Biotin Labeling Kit-NH$_2$ (Dojindo Laboratories) according to the manual. 1 μg of the biotinylated antibodies was added to 100 μL of each culture supernatant and shaken at 1,400 rpm at 20° C. for 2 hours. For washing of magnetic beads (Invitrogen Corp.), 100 μL of TBSTx (50 mM Tris-HCl (pH 8.0), 150 mM NaCl, and 1% Triton X-100) was added to 20 μL of the magnetic beads and stirred, followed by supernatant removal three times by centrifugation (10,000 rpm, 3 sec.). The reacted culture supernatant and antibodies were transferred to the magnetic beads and shaken at 1,400 rpm at 20° C. for 1 hour. The antibodies bound with the magnetic beads were recovered using a magnetic stand. The recovered magnetic beads were washed three times with 1 mL of TBSTx. After addition of 20 ul of an elution buffer (0.2% SDS in TBS), the mixture was stirred and then heated two times at 98° C. or 60° C. for 5 minutes for elution. In order to remove the antibodies on the eluted sample, 40 μL of magnetic beads washed in the same way as above was added to the eluted sample and shaken at 1,400 rpm at 20° C. for 2 hours. The antibody-bound magnetic beads were removed using a magnetic stand, and the remaining portion was used as a sample. The prepared sample was developed by SDS-PAGE and then subjected to lectin blot.

(Results)

Figure 4:
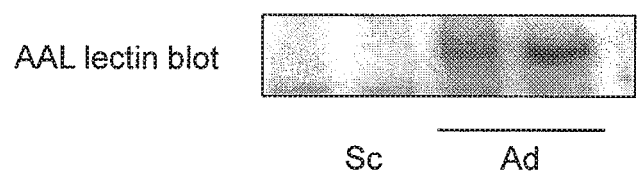
FIG. 4 is a blot image in which a lung cancer differential marker glycoprotein (fibronectin 1) in the culture supernatants of cultured small cell lung cancer cells (Sc) and cultured lung adenocarcinoma cells (Ad) fractionated with an antibody (anti-fibronectin 1 antibody) was detected with AAL lectin.

The lung cancer differential marker glycoproteins obtained by the steps described above are shown in FIG. 4.

6. Evaluation by Lectin Blot

10 μL of the immunoprecipitated sample was developed on a 10% gel by SDS-PAGE. After SDS-PAGE, the proteins were transferred to a PVDF membrane (GE Healthcare Japan Corp.). The PVDF membrane was blocked with 5% BSA at room temperature for 1 hour and then reacted with already biotinylated AAL lectin (Seikagaku Corp.) at room temperature for 1 hour. Then, the membrane was reacted with secondary antibody-HRP-conjugated streptavidin at room temperature for 1 hour. The proteins were detected using Western Lightning. PBS-T was used in the dilution of lectin.
(Results)

The lung cancer differential marker glycoproteins obtained by the steps described above are shown in FIG. 4.

7. Column Fractionation of Serum Using AAL Lectin

Serum was fractionated using AAL lectin. Specifically, a commercially available column was packed with 1 mL of an AAL-conjugated resin and washed with TBS in an amount of 10 times the amount of the resin, with 0.5 M NaCl in an amount of twice the amount of the resin, and with TBS in an amount of 10 times the amount of the resin to prepare an AAL column. Serum was added to the AAL column and then reacted for 1 hour in the resin. Then, the column was washed with TBS in an amount of 5 times the amount of the resin. For elution, 1 mL of 20 mM fucose was added thereto and reacted for 1 hour in the resin. Then, 4 mL of 20 mM fucose was further added thereto (a total of 5 mL) to elute the proteins.
(Results)

The lung cancer differential marker glycoproteins obtained by the steps described above are shown in FIG. 5.

8. Fractionation of Serum by Serial Chromatography

Serum was fractionated at a low temperature by serial chromatography using LCA agarose (J-Oil Mills, Inc.) and AAL agarose (J-Oil Mills, Inc.). Specifically, 100 µL of serum was diluted 4-fold with PBS. The serum sample was first applied to a column packed with 5 mL, of LCA agarose (0.7×13 cm). Next, the obtained unbound serum fractions were applied to a column packed with 2.5 mL of AAL agarose (0.7×5.5 cm). After sufficient washing with PBS, the proteins were eluted with PBS containing 0.2 M fucose. The eluted fractions were concentrated through Ultrafree Centrifugal Filter Device (cutoff: 30 kDa, Millipore Corp.). The candidate molecules in the obtained samples were analyzed by comparison by immunoblot in the same way as above.
(Results)

The lung cancer differential marker glycoproteins obtained by the steps described above are shown in FIG. 6.

9. Multisample Fractionation of Serum by Serial Chromatography

The multisample comparative analysis of sera requires fractionating a small amount of a serum sample in a short time. For this purpose, high-throughput serial chromatography was established. Sera were fractionated by serial chromatography using LCA agarose (J-Oil Mills, Inc.) and AAL agarose (Vector Laboratories, Inc.). 50 µL of a serum sample was applied to a tip column packed with 300 µL of LCA agarose (0.37×2.3 cm). Next, the obtained unbound serum fractions were applied to an open column packed with 250 µL of AAL agarose (0.8×0.5 cm). After sufficient washing with PBS, the proteins were eluted with PBS containing 0.02 M fucose. The eluted fractions were concentrated through Ultrafree Centrifugal Filter Device (cutoff: 30 kDa, Millipore Corp.). The candidate molecules in the obtained samples (corresponding to 10 µL of sera) were analyzed by comparison by immunoblot in the same way as above.
(Results)

The lung cancer differential marker glycoproteins obtained by the steps described above are shown in FIG. 8.

10. Antibody-Overlay Lectin Array

An appropriate amount of the glycoprotein solution obtained in the paragraph "5. Fractionation by immunoprecipitation" was adjusted to 60 µL with PBSTx (phosphate-buffered saline containing 1% Triton X-100) as a lectin array reaction buffer. This solution was added to each reaction vessel of a lectin array composed of 8 reaction vessels per a single glass plate, and reacted at 20° C. for 10 hours or longer. This lectin array substrate composed of 8 reaction vessels was prepared according to the approach of Uchiyama et al. (Proteomics 8, 3042-3050 (2008)). In this way, the binding reaction between the glycans on the glycoproteins and 43 types of lectins immobilized on the array substrate reaches an equilibrium state. In order to prevent noise from being generated by the binding of the glycans of antibodies for detection to unreacted lectins on the substrate, 2 µL of a human serum-derived IgG solution (manufactured by Sigma-Aldrich Corp.) was then added and reacted for 30 minutes. Each reaction vessel was washed three times with 60 µL of PBSTx. Then, 2 µL of a human serum-derived IgG solution was added thereto again and slightly stirred. Subsequently, biotinylated antibodies for detection against the glycoproteins were added in an amount corresponding to 100 ng and reacted at 20° C. for 1 hour. After this antigen-antibody reaction, each reaction vessel was washed three times with 60 µL of PBSTx. Then, the array was scanned with an array scanner GlycoStation manufactured by Moritex Corporation to compare fluorescence intensities on the lectin spots reacted in a lung cancer tissue-specific manner.
(Results)

The lung cancer differential marker glycoproteins obtained by the steps described above are shown in FIGS. 9 and 10.

The results of these experiments revealed that some lectins, such as PNA and PWM, other than AAL or ConA and lectins having specificity related to these ligands are effective for the differential diagnosis of lung cancer. This means that a plurality of lectin signals derived from glycoproteins may be combined in various ways to thereby more accurately determine the histological type of lung cancer.

Example 2

Histological staining of lung cancer cell using lung cancer differential marker

Histological staining with antibodies was tested using lung cancer differential markers.

First, paraffin that covered a formalin-fixed lung cancer tissue section (5 µm thick) was removed according to a standard method. The deparaffinized tissue section was washed with PBS, dried in air, and then dipped in a 10 mM citrate buffer. The intermolecular (intramolecular) bridges derived from formalin fixation were dissociated by autoclaving at 121° C. for 15 minutes. The section thus treated was left standing at room temperature for a while and then dipped three repetitive times in PBS for 5 minutes to wash the surface of the tissue. Subsequently, the section was treated with 0.3% $H_2O_2$-MeOH at room temperature for 10 minutes for the blocking reaction of endogenous peroxidase. After washing with PBS (5 min.×3), a primary antibody solution (R&D Systems, Inc.; anti-NPR antibody suspended at a concentration of 3 g/mL in PBS) was added onto the tissue section to cause binding reaction at 20° C. for 2 hours in a humidifying box. After washing with PBS (5 min.×3), chromogenic reaction was initiated using an anti-sheep FITC conjugate (Santa Cruz Biotechnology, Inc.) as a secondary antibody and an anti-FITC HRP conjugate (Takara Bio Inc.) as an enzymatically labeled antibody and terminated by dipping in Milli-Q water for 5 minutes three times. Finally, the nucleic acids were stained with hematoxylin at room temperature for 1 minute, followed by washing in running water.
(Results)

The lung cancer differential marker glycoproteins obtained by the steps described above are shown in FIG. 7. Staining specific only for small cell cancer was confirmed.

All publications, patents, and patent applications cited herein are incorporated herein by reference in their entirety.

We claim:

1. A method for determining whether a test subject afflicted with lung cancer is afflicted with adenocarcinoma comprising:
    (i) detecting a lung cancer differential marker glycoprotein glycosylated with a glycan at an asparagine residue or at least one fragment thereof in a sample obtained from the test subject, and
    (ii) determining whether the test subject is afflicted with adenocarcinoma by determining whether the glycoprotein or the fragment thereof is present in the sample; wherein the presence of the glycoprotein or fragment in the sample indicates that the test subject is afflicted with adenocarcinoma, and the absence of the glycoprotein or fragment in the sample indicates that the test subject is not afflicted with adenocarcinoma, and wherein:
    (a) the lung cancer differential marker glycoprotein is fibronectin 1, and the glycoprotein and the fragment thereof comprise the amino acid sequence;
    (b) the lung cancer differential marker glycoprotein or the fragment thereof is detected using at least one glycan probe that binds to a fucosylated glycan or β1,3-galactose wherein the glycan probe is PNA lectin; and
    (c) the sample is a body fluid, lung cancer tissue or a lung lavage.

2. The method of claim 1, wherein the body fluid is pleural effusion, lymph, a cell extract, sputum, or blood comprising serum, plasma and interstitial fluid.

3. A method of distinguishing between small cell lung cancer and lung adenocarcinoma in a test subject afflicted with small cell lung cancer or lung adenocarcinoma, the method comprising:
    (i) detecting binding of PNA lectin to a lung cancer differential marker glycoprotein or at least one fragment thereof in a sample obtained from the test subject by contacting the sample with the lectin, and
    (ii) determining that the lung cancer in the test subject is lung adenocarcinoma if the glycoprotein or fragment thereof in the sample acquired from the test subject binds to PNA, or that the lung cancer in the test subject is small cell lung cancer if the glycoprotein or fragment thereof in the sample acquired from the test subject does not bind to PNA,
    wherein the glycoprotein is fibronectin 1 and the glycoprotein and the fragment thereof comprise the amino acid sequence of SEQ ID NO: 19, wherein SEQ ID NO: 19 is glycosylated with a glycan at the asparagine residue at position 23;
    and wherein the sample is a body fluid, lung cancer tissue or a lung lavage.

4. The method of claim 3, wherein the body fluid is pleural effusion, lymph, a cell extract, sputum, or blood comprising serum, plasma and interstitial fluid.

* * * * *

UNITED STATES PATENT AND TRADEMARK OFFICE
CERTIFICATE OF CORRECTION

PATENT NO. : 10,539,576 B2
APPLICATION NO. : 15/620214
DATED : January 21, 2020
INVENTOR(S) : Hisashi Narimatsu et al.

Page 1 of 1

It is certified that error appears in the above-identified patent and that said Letters Patent is hereby corrected as shown below:

In the Claims

Claim 1
Column 207, Line 49, should read as follows:
    thereof comprise the amino acid sequence of SEQ ID NO: 19, wherein SEQ ID NO: 19 is glycosylated with a glycan at the asparagine residue at position 23;

Signed and Sealed this
Nineteenth Day of May, 2020

Andrei Iancu
*Director of the United States Patent and Trademark Office*